US012579242B2

(12) United States Patent
Shouldice et al.

(10) Patent No.: US 12,579,242 B2
(45) Date of Patent: Mar. 17, 2026

(54) SYSTEMS AND METHODS FOR DIGIT-BASED DIAGNOSTIC CHAIN OF CUSTODY MANAGEMENT

(71) Applicant: RESMED DIGITAL HEALTH INC., San Diego, CA (US)

(72) Inventors: Redmond Shouldice, Dublin (IE); Michael Scannell, Dublin (IE); Roxana Tiron, Dublin (IE); Ehsan Chah, Dublin (IE); Graeme Alexander Lyon, Dublin (IE)

(73) Assignee: RESMED DIGITAL HEALTH INC., San Diego, CA (US)

( * ) Notice: Subject to any disclaimer, the term of this patent is extended or adjusted under 35 U.S.C. 154(b) by 7 days.

(21) Appl. No.: 18/391,237

(22) Filed: Dec. 20, 2023

(65) Prior Publication Data

US 2024/0211566 A1      Jun. 27, 2024

Related U.S. Application Data

(60) Provisional application No. 63/434,413, filed on Dec. 21, 2022.

(51) Int. Cl.
*G06F 21/32* (2013.01)
*G16H 40/67* (2018.01)
*G06F 1/16* (2006.01)

(52) U.S. Cl.
CPC ............. *G06F 21/32* (2013.01); *G16H 40/67* (2018.01); *G06F 1/163* (2013.01)

(58) Field of Classification Search
CPC .......... G06F 21/32; G06F 1/163; G16H 40/67
See application file for complete search history.

(56) References Cited

U.S. PATENT DOCUMENTS 9,358,353 B2      6/2016   Armitstead et al.
10,281,953 B2 *   5/2019   von Badinski ...... A61B 5/6806
(Continued)

FOREIGN PATENT DOCUMENTS

WO      2008138040 A1    11/2008
WO      2012012835 A2     2/2012
(Continued)

OTHER PUBLICATIONS

Massie et al., "An Evaluation of the Night Owl Home Sleep Apnea Testing System", Journal of Clinical Sleep Medicine, vol. 14, No. 10, pp. 1791-1796, (Oct. 15, 2018).

*Primary Examiner* — Khoi V Le
(74) *Attorney, Agent, or Firm* — NIXON PEABODY LLP

(57) ABSTRACT

A method includes receiving sensor data from a device worn on one or more digits of a test subject. The method including determining physiological parameter(s) from at least a first portion of the sensor data acquired during a test session. The method including associating the determined physiological parameter(s) with the testing session. The method including authenticating the device by i) determining identification data using at least a second portion of the sensor data, the identification data including identifiable characteristic(s) of the one or more digits; ii) accessing authentication data that includes one or more authentication characteristics; and iii) comparing the identification data with the authentication data to determine a match to authenticate the device. The method including generating a chain of custody determination based at least in part on the authentication of the device. The method including associating the chain of custody determination with the testing session.

20 Claims, 13 Drawing Sheets

(56)     References Cited

U.S. PATENT DOCUMENTS

| | | | |
|---|---|---|---|
| 10,328,219 B2 | 6/2019 | Rao et al. | |
| 2014/0088373 A1 | 3/2014 | Phillips et al. | |
| 2017/0311879 A1 | 11/2017 | Armitstead et al. | |
| 2019/0130082 A1* | 5/2019 | Alameh | G06F 21/6218 |
| 2019/0303643 A1* | 10/2019 | Cao | H01H 13/52 |
| 2020/0015737 A1 | 1/2020 | Van Pee et al. | |
| 2020/0383580 A1 | 12/2020 | Shouldice et al. | |
| 2021/0073506 A1* | 3/2021 | Huang | G09G 3/32 |
| 2022/0007965 A1 | 1/2022 | Tiron et al. | |
| 2022/0211332 A1* | 7/2022 | Demmer | A61B 5/076 |

FOREIGN PATENT DOCUMENTS

| | | | |
|---|---|---|---|
| WO | 2014047310 A1 | 3/2014 | |
| WO | 2016061629 A1 | 4/2016 | |
| WO | 2017132726 A1 | 8/2017 | |
| WO | 2018050913 A1 | 3/2018 | |
| WO | 2019122413 A1 | 6/2019 | |
| WO | 2019122414 A1 | 6/2019 | |
| WO | 2020104465 A2 | 5/2020 | |
| WO | 2021260190 A1 | 12/2021 | |
| WO | 2021260192 A1 | 12/2021 | |

* cited by examiner

922

908

918

920

SYSTEMS AND METHODS FOR DIGIT-BASED DIAGNOSTIC CHAIN OF CUSTODY MANAGEMENT

CROSS REFERENCE TO RELATED APPLICATIONS

The present application claims the benefit of U.S. Provisional Application No. 63/434,413 filed Dec. 21, 2022 and entitled "SYSTEMS AND METHODS FOR DIGIT-BASED DIAGNOSTIC CHAIN OF CUSTODY MANAGEMENT," the disclosure of which is hereby incorporated by reference in its entirety.

TECHNICAL FIELD

The present disclosure relates generally to systems and methods for performing diagnostic tests, and more particularly, to systems and methods for establishing and managing chain of custody for diagnostic tests and testing devices.

BACKGROUND

Many individuals suffer from sleep-related and/or respiratory-related disorders such as, for example, Sleep Disordered Breathing (SDB), which can include Obstructive Sleep Apnea (OSA), Central Sleep Apnea (CSA), other types of apneas such as mixed apneas and hypopneas, Respiratory Effort Related Arousal (RERA), and snoring. In some cases, these disorders manifest, or manifest more pronouncedly, when the individual is in a particular lying/sleeping position. These individuals may also suffer from other health conditions (which may be referred to as comorbidities), such as insomnia (e.g., difficulty initiating sleep, frequent or prolonged awakenings after initially falling asleep, and/or an early awakening with an inability to return to sleep), Periodic Limb Movement Disorder (PLMD), Restless Leg Syndrome (RLS), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, and chest wall disorders.

These disorders are often treatable using a respiratory therapy system (e.g., a continuous positive airway pressure (CPAP) system), which delivers pressurized air to aid in preventing the individual's airway from narrowing or collapsing during sleep.

Individuals who may be suffering from sleep-related and/or respiratory-related disorders are often required to undergo substantial testing before a diagnosis can be made and before a treatment plan can be established and/or prescribed. Further, sleep testing can be required for certain professions, such as commercial truck drivers, pilots, law enforcement officers, and others.

Advances in sensor technology can permit the use of at-home testing equipment, however such equipment is susceptible to intentional and/or unintentional manipulation, such as if an at-home test provided for a first individual is intentionally and/or accidentally used by a second individual.

The present disclosure is directed to solving these and other problems.

SUMMARY

According to some implementations of the present disclosure, a method includes receiving, at a user device, first sensor data from one or more sensors coupled to the user device. The method also includes receiving identity enrollment information associated with a test subject engaging in a testing session. The method also includes establishing a communication link between the user device and a wearable diagnostic device. The method also includes associating the wearable diagnostic device with the testing session. Associating the wearable diagnostic device with the testing session includes determining that the wearable diagnostic device is being worn by the test subject at a first time based at least in part on the first sensor data. The method also includes receiving second sensor data from the wearable diagnostic device after the first time. The method also includes analyzing the second sensor data to identify an interference instance indicative that the wearable diagnostic device is no longer worn by the test subject at a second time. The method also includes generating a chain of custody determination based at least in part on the interference instance. The method also includes associating the chain of custody determination with the testing session.

According to some implementations of the present disclosure, a method includes receiving sensor data from a digit-wearable device worn on one or more digits of a test subject. The method also includes determining one or more physiological parameters from at least a first portion of the sensor data acquired during a test session. The method also includes associating the determined one or more physiological parameters with the testing session. The method also includes authenticating the digit-wearable device. Authenticating the digit-wearable device includes determining identification data based at least in part on at least a second portion of the sensor data. The identification data includes one or more identifiable characteristics of the one or more digits. Authenticating the digit-wearable device also includes accessing authentication data. The authentication data includes one or more authentication characteristics. Authenticating the digit-wearable device also includes comparing the identification data with the authentication data to determine a match. The digit-wearable device is authenticated when a match is determined. The method also includes generating a chain of custody determination based at least in part on the authentication of the digit-wearable device. The method also includes associating the chain of custody determination with the testing session.

According to some implementations of the present disclosure, a method includes providing a tag applied to an intended test subject. The tag has an anti-tamper authentication feature. The anti-tamper authentication feature is altered when the tag is removed from the test subject. The anti-tamper authentication feature, when altered, is rendered unsuitable for authentication. The method also includes providing a diagnostic wearable device applied to a test subject. The diagnostic wearable device interacts with the anti-tamper authentication feature of the tag. The method also includes authenticating the tag with the diagnostic wearable device based at least in part on the diagnostic wearable device's interaction with the anti-tamper authentication feature. Successful authentication is indicative that the test subject is the intended test subject. Unsuccessful authentication occurs when the anti-tamper authentication feature is altered. The method also includes collecting sensor data from the test subject via the diagnostic wearable device. The method also includes associating the collected sensor data with the intended test subject based at least in part on the authentication of the tag with the diagnostic wearable device.

According to some implementations of the present disclosure, a method includes providing a tag applied to an intended test subject. The tag has an anti-tamper authentication feature, The anti-tamper authentication feature is altered when the tag is removed from the test subject. Wherein the anti-tamper authentication feature, when altered, is rendered unsuitable for authentication. The method also includes providing a diagnostic wearable device applied to a test subject. The method also includes receiving, by a user device, first data from the anti-tamper authentication feature. The method also includes receiving, by the user device, second data from the diagnostic wearable device. The method also includes authenticating the tag with the diagnostic wearable device based at least in part on the first data and the second data. Successful authentication is indicative that the test subject is the intended test subject. Unsuccessful authentication occurs when the anti-tamper authentication feature is altered. The method also includes storing sensor data collected from the test subject via the diagnostic wearable device. The sensor data is included in the second data or in additional data received by the user device. The method also includes associating the sensor data with the intended test subject based at least in part on the authentication of the tag with the diagnostic wearable device.

According to some implementations of the present disclosure, a system includes an electronic interface, a memory, and a control system. The electronic interface is configured to receive data associated with a test subject. The memory stores machine-readable instructions. The control system includes one or more processors configured to execute the machine-readable instructions to perform the methods disclosed above.

The above summary is not intended to represent each implementation or every aspect of the present disclosure. Additional features and benefits of the present disclosure are apparent from the detailed description and figures set forth below.

Figure 1:
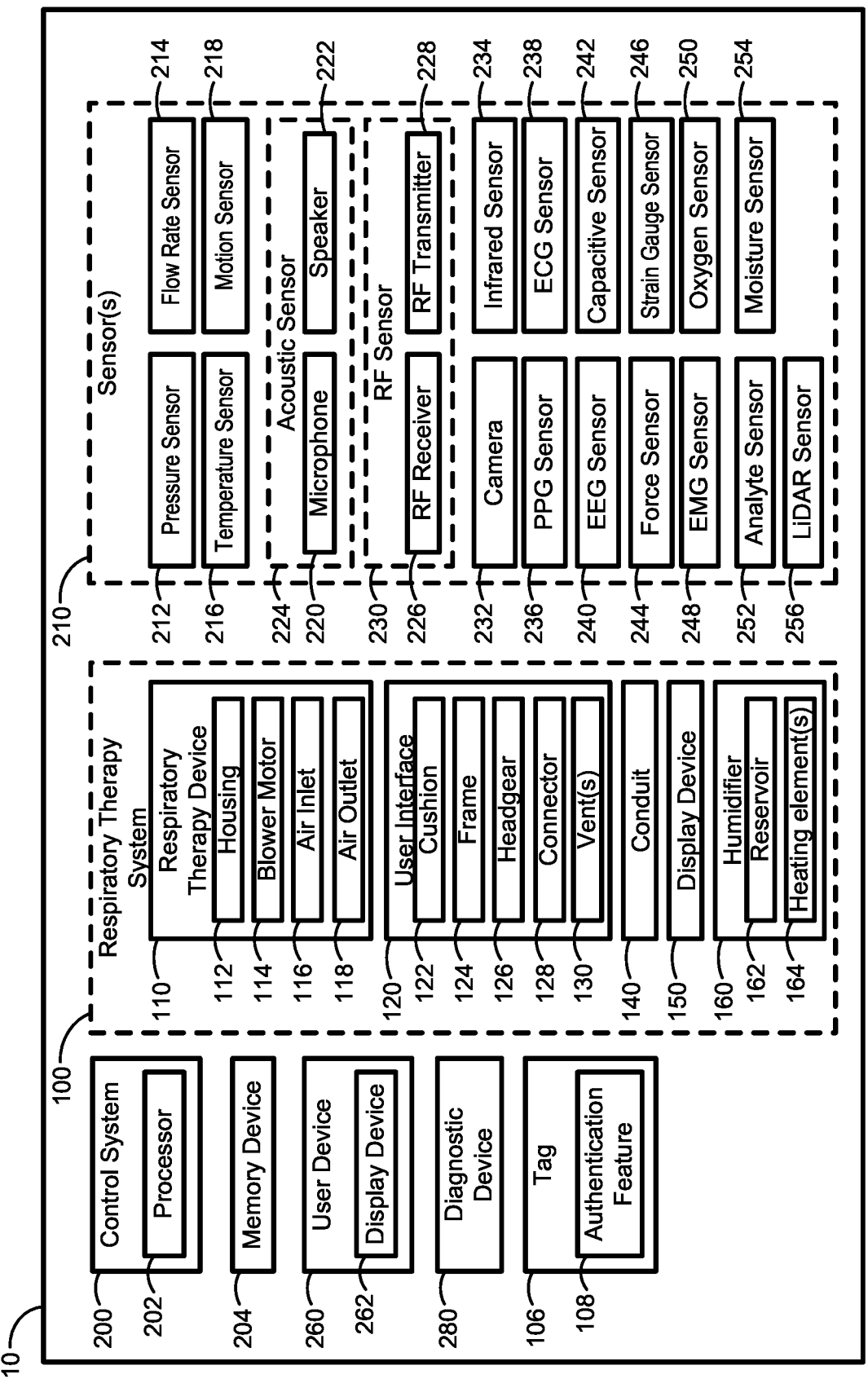
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer, knowingly or not, from sleep-related and/or respiratory disorders, such as Sleep Disordered Breathing (SDB) such as Obstructive Sleep Apnea (OSA), Central Sleep Apnea (CSA) and other types of apneas, Respiratory Effort Related Arousal (RERA), snoring, Cheyne-Stokes Respiration (CSR), respiratory insufficiency, Obesity Hyperventilation Syndrome (OHS), Chronic Obstructive Pulmonary Disease (COPD), Periodic Limb Movement Disorder (PLMD), Restless Leg Syndrome (RLS), Neuromuscular Disease (NMD), and chest wall disorders.

Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). CSA results when the brain temporarily stops sending signals to the muscles that control breathing. Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events fulfil the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., the disclosure of each of which is hereby incorporated by reference herein in their entireties.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. COPD encompasses a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 10, according to some implementations of the present disclosure, is illustrated. The system 10 includes a respiratory therapy system 100, a diagnostic device 280, a control system 200, one or more sensors 210, a user device 260, and a tag 106. The system 10 can include fewer or additional components, as well as multiple versions of any given component, such as described in further detail herein.

The respiratory therapy system 100 includes a respiratory pressure therapy (RPT) device 110 (referred to herein as respiratory therapy device 110), a user interface 120 (also referred to as a mask or a patient interface), a conduit 140 (also referred to as a tube or an air circuit), a display device 150, and a humidifier 160. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 100 is generally used to treat individuals suffering from one or more sleep-related respiratory disorders (e.g., obstructive sleep apnea, central sleep apnea, or mixed sleep apnea).

The respiratory therapy system 100 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

The respiratory therapy system 100 can be used to treat user. In an example, the user of the respiratory therapy system 100 and a bed partner are located in a bed and are laying on a mattress. The user interface 120 can be worn by the user during a sleep session. The respiratory therapy system 100 generally aids in increasing the air pressure in the throat of the user to aid in preventing the airway from closing and/or narrowing during sleep. The respiratory therapy device 110 can be positioned on a nightstand that is directly adjacent to the bed, or more generally, on any surface or structure that is generally adjacent to the bed and/or the user.

The respiratory therapy device 110 is generally used to generate pressurized air that is delivered to a user (e.g., using one or more motors that drive one or more compressors). In some implementations, the respiratory therapy device 110 generates continuous constant air pressure that is delivered to the user. In other implementations, the respiratory therapy device 110 generates two or more predetermined pressures (e.g., a first predetermined air pressure and a second predetermined air pressure). In still other implementations, the respiratory therapy device 110 generates a variety of different air pressures within a predetermined range. For example, the respiratory therapy device 110 can deliver at least about 6 cmH$_2$O, at least about 10 cmH$_2$O, at least about 20 cmH$_2$O, between about 6 cmH$_2$O and about 10 cmH$_2$O, between about 7 cmH$_2$O and about 12 cmH$_2$O, etc. The respiratory therapy device 110 can also deliver pressurized air at a predetermined flow rate between, for example, about −20 L/min and about 150 L/min, while maintaining a positive pressure (relative to the ambient pressure).

The respiratory therapy device 110 includes a housing 112, a blower motor 114, an air inlet 116, and an air outlet 118 (FIG. 1). The blower motor 114 is at least partially disposed or integrated within the housing 112. The blower motor 114 draws air from outside the housing 112 (e.g., atmosphere) via the air inlet 116 and causes pressurized air to flow through the humidifier 160, and through the air outlet 118. In some implementations, the air inlet 116 and/or the air outlet 118 include a cover that is moveable between a closed position and an open position (e.g., to prevent or inhibit air from flowing through the air inlet 116 or the air outlet 118). The housing 112 can include a vent to allow air to pass through the housing 112 to the air inlet 116. As described below, the conduit 140 is coupled to the air outlet 118 of the respiratory therapy device 110.

The user interface 120 engages a portion of the user's face and delivers pressurized air from the respiratory therapy device 110 to the user's airway to aid in preventing the airway from narrowing and/or collapsing during sleep. This may also increase the user's oxygen intake during sleep. Generally, the user interface 120 engages the user's face such that the pressurized air is delivered to the user's airway via the user's mouth, the user's nose, or both the user's mouth and nose. Together, the respiratory therapy device 110, the user interface 120, and the conduit 140 form an air pathway fluidly coupled with an airway of the user. The pressurized air also increases the user's oxygen intake during sleep. Depending upon the therapy to be applied, the user interface 120 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 $cmH_2O$.

The user interface 120 can include, for example, a cushion 122, a frame 124, a headgear 126, connector 128, and one or more vents 130. The cushion 122 and the frame 124 define a volume of space around the mouth and/or nose of the user. When the respiratory therapy system 100 is in use, this volume space receives pressurized air (e.g., from the respiratory therapy device 110 via the conduit 140) for passage into the airway(s) of the user. The headgear 126 is generally used to aid in positioning and/or stabilizing the user interface 120 on a portion of the user (e.g., the face), and along with the cushion 122 (which, for example, can comprise silicone, plastic, foam, etc.) aids in providing a substantially air-tight seal between the user interface 120 and the user. In some implementations the headgear 126 includes one or more straps (e.g., including hook and loop fasteners). The connector 128 is generally used to couple (e.g., connect and fluidly couple) the conduit 140 to the cushion 122 and/or frame 124. Alternatively, the conduit 140 can be directly coupled to the cushion 122 and/or frame 124 without the connector 128. The vent 130 can be used for permitting the escape of carbon dioxide and other gases exhaled by the user. The user interface 120 generally can include any suitable number of vents (e.g., one, two, five, ten, etc.).

In some implementations, the user interface 120 is a facial mask (e.g., a full face mask) that covers at least a portion of the nose and mouth of the user. Alternatively, the user interface 120 can be a nasal mask that provides air to the nose of the user or a nasal pillow mask that delivers air directly to the nostrils of the user. In other implementations, the user interface 120 includes a mouthpiece (e.g., a night guard mouthpiece molded to conform to the teeth of the user, a mandibular repositioning device, etc.).

In some implementations, a user interface 120 can include a cushion 122 and a frame 124 that define a volume of space around the mouth and/or nose of the user. When in use, the volume of space receives pressurized air for passage into the user's airways. In some implementations, the cushion 122 and frame 124 of the user interface 120 form a unitary component of the user interface. The user interface 120 can also include a headgear 126, which generally includes a strap assembly and optionally a connector 128. The headgear 126 is configured to be positioned generally about at least a portion of a user's head when the user wears the user interface 120. The headgear 126 can be coupled to the frame 124 and positioned on the user's head such that the user's head is positioned between the headgear 126 and the frame 124. The cushion 122 is positioned between the user's face and the frame 124 to form a seal on the user's face. The optional connector 128 is configured to couple to the frame 124 and/or cushion 122 at one end and to a conduit 140 of a respiratory therapy device 110. The pressurized air can flow directly from the conduit 140 of the respiratory therapy system 100 into the volume of space defined by the cushion 122 (or cushion 122 and frame 124) of the user interface 120 through the connector 128). From the user interface 120, the pressurized air reaches the user's airway through the user's mouth, nose, or both. Alternatively, where the user interface 120 does not include the connector 128, the conduit 140 of the respiratory therapy system 100 can connect directly to the cushion 122 and/or the frame 124.

In some implementations, the connector 128 may include one or more vents 130 (e.g., a plurality of vents) located on the main body of the connector 128 itself and/or one or a plurality of vents 130 ("diffuser vents") in proximity to the frame 124, for permitting the escape of carbon dioxide ($CO_2$) and other gases exhaled by the user. In some implementations, one or a plurality of vents may be located in the user interface 120, such as in frame 124, and/or in the conduit 140. In some implementations, the frame 124 includes at least one anti-asphyxia valve (AAV), which allows $CO_2$ and other gases exhaled by the user to escape in the event that the vent(s) 130 fail when the respiratory therapy device is active. In general, AAVs are present for full face masks (e.g., as a safety feature); however, the diffuser vents and vents located on the mask or connector (usually an array of orifices in the mask material itself or a mesh made of some sort of fabric, in many cases replaceable) are not necessarily both present (e.g., some masks might have only the diffuser vents, other masks might have only the plurality of vents on the connector itself).

In some implementations, a user interface 120 can be an indirect user interface. Such a user interface 120 includes a headgear 126 (e.g., as a strap assembly), a cushion 122, a frame 124, a connector 128, and a user interface conduit (often referred to as a minitube or a flexitube). The user interface 120 is an indirectly connected user interface because pressurized air is delivered from the conduit 140 of the respiratory therapy system to the cushion 122 and/or frame 124 through the user interface conduit, rather than directly from the conduit 140 of the respiratory therapy system 100.

In some implementations, the cushion 122 and frame 124 form a unitary component of the user interface 120. Generally, the user interface conduit is more flexible than the conduit 140 of the respiratory therapy system 100 described above and/or has a diameter smaller than the diameter of the than the than the conduit 140. The user interface conduit is typically shorter that conduit 140. The headgear 126 of such a user interface 120 can be configured to be positioned generally about at least a portion of a user's head when the user wears the user interface 120. The headgear 126 can be coupled to the frame 124 and positioned on the user's head such that the user's head is positioned between the headgear 126 and the frame 124. The cushion 122 is positioned between the user's face and the frame 124 to form a seal on the user's face. The connector 128 is configured to couple to the frame 124 and/or cushion 122 at one end and to the conduit of the user interface 120 at the other end. In other implementations, the user interface conduit may connect directly to frame 124 and/or cushion 122. The user interface conduit, at the opposite end relative to the frame 124 and cushion 122, is configured to connect to the conduit 140. The pressurized air can flow from the conduit 140 of the respiratory therapy system 100, through the user interface conduit, and the connector 128, and into a volume of space define by the cushion 122 (or cushion 122 and frame 124) of the user interface 120 against a user's face. From the volume of space, the pressurized air reaches the user's airway through the user's mouth, nose, or both.

In some implementations, the connector 128 includes a plurality of vents 130 for permitting the escape of carbon dioxide ($CO_2$) and other gases exhaled by the user when the respiratory therapy device is active. In such implementations, each of the plurality of vents is an opening that may be angled relative to the thickness of the connector wall through which the opening is formed. The angled openings can reduce noise of the $CO_2$ and other gases escaping to the atmosphere. Because of the reduced noise, acoustic signal associated with the plurality of vents may be more apparent to an internal microphone, as opposed to an external microphone. Thus, an internal microphone may be located within, or otherwise physically integrated with, the respiratory therapy system and in acoustic communication with the flow of air which, in operation, is generated by the flow generator of the respiratory therapy device, and passes through the conduit and to the user interface 120.

In some implementations, the connector 128 optionally includes at least one valve for permitting the escape of $CO_2$ and other gases exhaled by the user when the respiratory therapy device is inactive. In some implementations, the valve (an example of an anti-asphyxia valve) includes a silicone (or other suitable material) flap that is a failsafe component, which allows $CO_2$ and other gases exhaled by the user to escape in the event that the vents 130 fail when the respiratory therapy device is active. In such implementations, when the silicone flap is open, the valve opening is much greater than each vent opening, and therefore less likely to be blocked by occlusion materials.

In some implementations, the user interface 120 can be another form of indirect user interface. The indirect headgear user interface includes headgear 126, a cushion 122, and a connector 128. The headgear 126 includes strap and a headgear conduit. The headgear 126 is configured to be positioned generally about at least a portion of a user's head when the user wears the user interface 120. The headgear 126 includes a strap that can be coupled to the headgear conduit and positioned on the user's head such that the user's head is positioned between the strap and the headgear conduit. The cushion 122 is positioned between the user's face and the headgear conduit to form a seal on the user's face.

In such implementations, the connector 128 is configured to couple to the headgear 126 at one end and a conduit of the respiratory therapy system at the other end (e.g., conduit 140). In some cases, the connector 128 is not included and the headgear 126 can alternatively connect directly to conduit of the respiratory therapy system. The headgear conduit can be configured to deliver pressurized air from the conduit of the respiratory therapy system to the cushion 122, or more specifically, to the volume of space around the mouth and/or nose of the user and enclosed by the user cushion 122. The headgear conduit is hollow to provide a passageway for the pressurized air. Both sides of the headgear conduit can be hollow to provide two passageways for the pressurized air. Alternatively, only one side of the headgear conduit can be hollow to provide a single passageway. In some cases, a headgear conduit comprises two passageways which, in use, are positioned at either side of a user's head/face. Alternatively, only one passageway of the headgear conduit can be hollow to provide a single passageway. The pressurized air can flow from the conduit 140 of the respiratory therapy system, through the connector 128 and the headgear conduit, and into the volume of space between the cushion 122 and the user's face. From the volume of space between the cushion 122 and the user's face, the pressurized air reaches the user's airway through the user's mouth, nose, or both.

In some implementations, the cushion 122 includes a plurality of vents 130 on the cushion 122 itself. Additionally or alternatively, in some implementations, the connector 128 includes a plurality of vents 130 ("diffuser vents") in proximity to the headgear 126, for permitting the escape of carbon dioxide ($CO_2$) and other gases exhaled by the user when the respiratory therapy device is active. In some implementations, the headgear 126 may include at least one plus anti-asphyxia valve (AAV) in proximity to the cushion 122, which allows $CO_2$ and other gases exhaled by the user to escape in the event that the vent(s) 130 fail when the respiratory therapy device is active.

The conduit 140 (also referred to as an air circuit or tube) allows the flow of air between components of the respiratory therapy system 100, such as between the respiratory therapy device 110 and the user interface 120. In some implementations, there can be separate limbs of the conduit for inhalation and exhalation. In other implementations, a single limb conduit is used for both inhalation and exhalation.

In some cases, the conduit 140 includes a first end that is coupled to the air outlet 118 of the respiratory therapy device 110. The first end can be coupled to the air outlet 118 of the respiratory therapy device 110 using a variety of techniques (e.g., a press fit connection, a snap fit connection, a threaded connection, etc.). In some implementations, the conduit 140 includes one or more heating elements that heat the pressurized air flowing through the conduit 140 (e.g., heat the air to a predetermined temperature or within a range of predetermined temperatures). Such heating elements can be coupled to and/or imbedded in the conduit 140. In such implementations, the first end can include an electrical contact that is electrically coupled to the respiratory therapy device 110 to power the one or more heating elements of the conduit 140. For example, the electrical contact can be electrically coupled to an electrical contact of the air outlet 118 of the respiratory therapy device 110. In this example, electrical contact of the conduit 140 can be a male connector and the electrical contact of the air outlet 118 can be female connector, or, alternatively, the opposite configuration can be used.

The display device 150 is generally used to display image(s) including still images, video images, or both and/or information regarding the respiratory therapy device 110. For example, the display device 150 can provide information regarding the status of the respiratory therapy device 110 (e.g., whether the respiratory therapy device 110 is on/off, the pressure of the air being delivered by the respiratory therapy device 110, the temperature of the air being delivered by the respiratory therapy device 110, etc.) and/or other information (e.g., a sleep score and/or a therapy score, also referred to as a my Air™ score, such as described in WO 2016/061629 and U.S. Patent Pub. No. 2017/0311879, which are hereby incorporated by reference herein in their entireties, the current date/time, personal information for the user 20, etc.). In some implementations, the display device 150 acts as a human-machine interface (HMI) that includes a graphic user interface (GUI) configured to display the image(s) as an input interface. The display device 150 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 110.

The humidifier 160 is coupled to or integrated in the respiratory therapy device 110 and includes a reservoir 162 for storing water that can be used to humidify the pressurized air delivered from the respiratory therapy device 110. The humidifier 160 includes a one or more heating elements 164 to heat the water in the reservoir to generate water vapor. The humidifier 160 can be fluidly coupled to a water vapor inlet of the air pathway between the blower motor 114 and the air outlet 118, or can be formed in-line with the air pathway between the blower motor 114 and the air outlet 118. For example, air flow from the air inlet 116 through the blower motor 114, and then through the humidifier 160 before exiting the respiratory therapy device 110 via the air outlet 118.

While the respiratory therapy system 100 has been described herein as including each of the respiratory therapy device 110, the user interface 120, the conduit 140, the display device 150, and the humidifier 160, more or fewer components can be included in a respiratory therapy system according to implementations of the present disclosure. For example, a first alternative respiratory therapy system includes the respiratory therapy device 110, the user interface 120, and the conduit 140. As another example, a second alternative system includes the respiratory therapy device 110, the user interface 120, and the conduit 140, and the display device 150. Thus, various respiratory therapy systems can be formed using any portion or portions of the components shown and described herein and/or in combination with one or more other components.

The control system 200 includes one or more processors 202 (hereinafter, processor 202). The control system 200 is generally used to control (e.g., actuate) the various components of the system 10 and/or analyze data obtained and/or generated by the components of the system 10. The processor 202 can be a general or special purpose processor or microprocessor. While one processor 202 is illustrated in FIG. 1, the control system 200 can include any number of processors (e.g., one processor, two processors, five processors, ten processors, etc.) that can be in a single housing, or located remotely from each other. The control system 200 (or any other control system) or a portion of the control system 200 such as the processor 202 (or any other processor(s) or portion(s) of any other control system), can be used to carry out one or more steps of any of the methods described and/or claimed herein. The control system 200 can be coupled to and/or positioned within, for example, a housing of the user device 260, a housing of the diagnostic device 280, a housing of the tag 106, and/or within a housing of one or more of the sensors 210. The control system 200 can be centralized (within one such housing) or decentralized (within two or more of such housings, which are physically distinct). In such implementations including two or more housings containing the control system 200, the housings can be located proximately and/or remotely from each other.

The memory device 204 stores machine-readable instructions that are executable by the processor 202 of the control system 200. The memory device 204 can be any suitable computer readable storage device or media, such as, for example, a random or serial access memory device, a hard drive, a solid state drive, a flash memory device, etc. While one memory device 204 is shown in FIG. 1, the system 10 can include any suitable number of memory devices 204 (e.g., one memory device, two memory devices, five memory devices, ten memory devices, etc.). The memory device 204 can be coupled to and/or positioned within a housing of the user device 260, within a housing of the diagnostic device 280, within a housing of the tag 106, within a housing of one or more of the sensors 210, or any combination thereof. Like the control system 200, the memory device 204 can be centralized (within one such housing) or decentralized (within two or more of such housings, which are physically distinct).

In some implementations, the memory device 204 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), past testing data, or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

As described herein, the processor 202 and/or memory device 204 can receive data (e.g., physiological data and/or audio data) from the one or more sensors 210 such that the data for storage in the memory device 204 and/or for analysis by the processor 202. The processor 202 and/or memory device 204 can communicate with the one or more sensors 210 using a wired connection or a wireless connection (e.g., using an RF communication protocol, a Wi-Fi communication protocol, a Bluetooth communication protocol, over a cellular network, an optical communication protocol, an auditory communication protocol, etc.). In some implementations, the system 10 can include an antenna, a receiver (e.g., an RF receiver, an optical receiver, an auditory receiver, etc.), a transmitter (e.g., an RF transmitter, an optical transmitter, an auditory transmitter, etc.), a transceiver, or any combination thereof. Such components can be coupled to or integrated a housing of the control system 200

(e.g., in the same housing as the processor 202 and/or memory device 204), or the user device 260.

Referring to back to FIG. 1, the one or more sensors 210 include a pressure sensor 212, a flow rate sensor 214, temperature sensor 216, a motion sensor 218, a microphone 220, a speaker 222, a radio-frequency (RF) receiver 226, a RF transmitter 228, a camera 232, an infrared sensor 234, a photoplethysmogram (PPG) sensor 236, an electrocardiogram (ECG) sensor 238, an electroencephalography (EEG) sensor 240, a capacitive sensor 242, a force sensor 244, a strain gauge sensor 246, an electromyography (EMG) sensor 248, an oxygen sensor 250, an analyte sensor 252, a moisture sensor 254, a LiDAR sensor 256, or any combination thereof. Generally, each of the one or more sensors 210 are configured to output sensor data that is received and stored in the memory device 204 or one or more other memory devices.

While the one or more sensors 210 are shown and described as including each of the pressure sensor 212, the flow rate sensor 214, the temperature sensor 216, the motion sensor 218, the microphone 220, the speaker 222, the RF receiver 226, the RF transmitter 228, the camera 232, the infrared sensor 234, the photoplethysmogram (PPG) sensor 236, the electrocardiogram (ECG) sensor 238, the electroencephalography (EEG) sensor 240, the capacitive sensor 242, the force sensor 244, the strain gauge sensor 246, the electromyography (EMG) sensor 248, the oxygen sensor 250, the analyte sensor 252, the moisture sensor 254, and the LiDAR sensor 256, more generally, the one or more sensors 210 can include any combination and any number of each of the sensors described and/or shown herein.

As described herein, the system 10 generally can be used to generate physiological data associated with a user (e.g., a test subject associated with diagnostic device 280), such as during a sleep session. The physiological data can be analyzed to generate one or more sleep-related parameters, which can include any parameter, measurement, etc. related to the user during the sleep session. The one or more sleep-related parameters that can be determined for the user during the sleep session include, for example, an Apnea-Hypopnea Index (AHI) score, a sleep score, a respiration signal, a respiration rate, an inspiration amplitude, an expiration amplitude, an inspiration-expiration ratio, a number of events per hour, a pattern of events, a stage, a heart rate, a heart rate variability, movement of the user, temperature, EEG activity, EMG activity, arousal, snoring, choking, coughing, whistling, wheezing, blood oxygen saturation level, or any combination thereof.

The one or more sensors 210 can be used to generate, for example, physiological data, audio data, or both. Physiological data generated by one or more of the sensors 210 can be used by the control system 200 to determine a sleep-wake signal associated with the user during the sleep session and one or more sleep-related parameters. The sleep-wake signal can be indicative of one or more sleep states, including wakefulness, relaxed wakefulness, micro-awakenings, or distinct sleep stages such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 210, are described in, for example, WO 2014/047310, U.S. Patent Pub. No. 2014/0088373, WO 2017/132726, WO 2019/122413, WO 2019/122414, and U.S. Patent Pub. No. 2020/0383580 each of which is hereby incorporated by reference herein in its entirety.

In some implementations, the sleep-wake signal described herein can be timestamped to indicate a time that the user enters the bed, a time that the user exits the bed, a time that the user attempts to fall asleep, etc. The sleep-wake signal can be measured by the one or more sensors 210 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, or any combination thereof during the sleep session. The event(s) can include snoring, apneas, central apneas, obstructive apneas, mixed apneas, hypopneas, a mask leak (e.g., for individuals wearing a user interface of a respiratory therapy system), a restless leg, a sleeping disorder, choking, an increased heart rate, decreased blood oxygen saturation level, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more sleep-related scores.

Physiological data and/or audio data generated by the one or more sensors 210 can also be used to determine a respiration signal associated with a user during a sleep session. The respiration signal is generally indicative of respiration or breathing of the user during the sleep session. The respiration signal can be indicative of and/or analyzed to determine (e.g., using the control system 200) one or more sleep-related parameters, such as, for example, a respiration rate, a respiration rate variability, an inspiration amplitude, an expiration amplitude, an inspiration-expiration ratio, an occurrence of one or more events, a number of events per hour, a pattern of events, a sleep state, a sleet stage, an apnea-hypopnea index (AHI), or any combination thereof. The one or more events can include snoring, apneas, central apneas, obstructive apneas, mixed apneas, hypopneas, a mask leak (e.g., for individuals wearing a user interface of a respiratory therapy system), a cough, a restless leg, a sleeping disorder, choking, an increased heart rate, a decreased blood oxygen saturation level, labored breathing, an asthma attack, an epileptic episode, a seizure, increased blood pressure, or any combination thereof. Many of the described sleep-related parameters are physiological parameters, although some of the sleep-related parameters can be considered to be non-physiological parameters. Other types of physiological and/or non-physiological parameters can also be determined, either from the data from the one or more sensors 210, or from other types of data.

The pressure sensor 212 outputs pressure data that can be stored in the memory device 204 and/or analyzed by the processor 202 of the control system 200. In some implementations, the pressure sensor 212 is used to determine pressure of a flow of pressurized air from a respiratory therapy device being used by a user, pressure of a flow of pressurized air through a conduit of a respiratory therapy system, pressure of a flow of pressurized air through a user interface of a respiratory therapy system, or any combination thereof. In some implementations, the pressure sensor 212 is an air pressure sensor (e.g., barometric pressure sensor) that generates sensor data indicative of the respiration (e.g., inhaling and/or exhaling) of the user and/or ambient pressure. The pressure sensor 212 can be, for example, a capacitive sensor, an electromagnetic sensor, a piezoelectric sensor, a strain-gauge sensor, an optical sensor, a potentiometric sensor, or any combination thereof.

The flow rate sensor 214 outputs flow rate data that can be stored in the memory device 204 and/or analyzed by the processor 202 of the control system 200. Examples of flow rate sensors (such as, for example, the flow rate sensor 214) are described in International Publication No. WO 2012/012835 and U.S. Pat. No. 10,328,219, both of which are hereby incorporated by reference herein in their entireties. In some implementations, the flow rate sensor 214 is used to determine an air flow rate from a respiratory therapy device being used by a user, an air flow rate through a conduit of a respiratory therapy system, an air flow rate through a user interface of a respiratory therapy system, or any combination thereof. The flow rate sensor 214 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate data can be analyzed to determine cardiogenic oscillations of the user. In some examples, the pressure sensor 212 can be used to determine a blood pressure of a user.

The temperature sensor 216 outputs temperature data that can be stored in the memory device 204 and/or analyzed by the processor 202 of the control system 200. In some implementations, the temperature sensor 216 generates temperatures data indicative of a core body temperature of the user, a skin temperature of the user, a temperature of the diagnostic device 280, a temperature associated with the tag 106, an ambient temperature, or any combination thereof. The temperature sensor 216 can be, for example, a thermocouple sensor, a thermistor sensor, a silicon band gap temperature sensor or semiconductor-based sensor, a resistance temperature detector, or any combination thereof.

The motion sensor 218 outputs motion data that can be stored in the memory device 204 and/or analyzed by the processor 202 of the control system 200. The motion sensor 218 can be used to detect movement of the user (e.g., during the sleep session), detect movement of the diagnostic device 280, detect movement of the tag 106, detect movement of the user device 260, or any combination thereof. The motion sensor 218 can include one or more inertial sensors, such as accelerometers, gyroscopes, and magnetometers. In some implementations, the motion sensor 218 alternatively or additionally generates one or more signals representing bodily movement of the user, from which may be obtained a signal representing a sleep state of the user; for example, via a respiratory movement of the user. In some implementations, the motion data from the motion sensor 218 can be used in conjunction with additional data from another one of the sensors 210 to determine the sleep state of the user.

The microphone 220 outputs sound and/or audio data that can be stored in the memory device 204 and/or analyzed by the processor 202 of the control system 200. The audio data generated by the microphone 220 is reproducible as one or more sound(s) during a sleep session (e.g., sounds from the user). The audio data form the microphone 220 can also be used to identify (e.g., using the control system 200) an event experienced by the user during the sleep session, as described in further detail herein. The microphone 220 can be coupled to or integrated in the diagnostic device 280, the tag 106, the user device 260, or any combination thereof. In some implementations, the system 10 includes a plurality of microphones (e.g., two or more microphones and/or an array of microphones with beamforming) such that sound data generated by each of the plurality of microphones can be used to discriminate the sound data generated by another of the plurality of microphones The speaker 222 outputs sound waves. In some cases, sound waves are audible to a user of the system 10, although that need not always be the case (e.g., when speaker 222 is used for non-audible auditory communication protocols). The speaker 222 can be used, for example, as an alarm clock or to play an alert or message to the user (e.g., in response to an event). In some implementations, the speaker 222 can be used to communicate the audio data generated by the microphone 220 to the user. The speaker 222 can be coupled to or integrated in the diagnostic device 280, the tag 106, the user device 260, or any combination thereof.

The microphone 220 and the speaker 222 can be used as separate devices. In some implementations, the microphone 220 and the speaker 222 can be combined into an acoustic sensor 224 (e.g., a SONAR sensor), as described in, for example, WO 2018/050913, WO 2020/104465, U.S. Pat. App. Pub. No. 2022/0007965, each of which is hereby incorporated by reference herein in its entirety. In such implementations, the speaker 222 generates or emits sound waves at a predetermined interval and the microphone 220 detects the reflections of the emitted sound waves from the speaker 222. The sound waves generated or emitted by the speaker 222 have a frequency that is not audible to the human ear (e.g., below 20 Hz or above around 18 kHz) so as not to disturb the sleep of the user or a bed partner. Based at least in part on the data from the microphone 220 and/or the speaker 222, the control system 200 can determine a location of the user and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, a sleep stage, or any combination thereof. In such a context, a sonar sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air.

In some implementations, the sensors 210 include (i) a first microphone that is the same as, or similar to, the microphone 220, and is integrated in the acoustic sensor 224 and (ii) a second microphone that is the same as, or similar to, the microphone 220, but is separate and distinct from the first microphone that is integrated in the acoustic sensor 224.

The RF transmitter 228 generates and/or emits radio waves having a predetermined frequency and/or a predetermined amplitude (e.g., within a high frequency band, within a low frequency band, long wave signals, short wave signals, etc.). The RF receiver 226 detects the reflections of the radio waves emitted from the RF transmitter 228, and this data can be analyzed by the control system 200 to determine a location of the user and/or one or more of the sleep-related parameters described herein. An RF receiver (either the RF receiver 226 and the RF transmitter 228 or another RF pair) can also be used for wireless communication between the control system 200, the user device 260, the diagnostic device 280, the tag 106, the one or more sensors 210, or any combination thereof. While the RF receiver 226 and RF transmitter 228 are shown as being separate and distinct elements in FIG. 1, in some implementations, the RF receiver 226 and RF transmitter 228 are combined as a part of an RF sensor 230 (e.g. a RADAR sensor). In some such implementations, the RF sensor 230 includes a control circuit. The format of the RF communication can be Wi-Fi, Bluetooth, or the like.

In some implementations, the RF sensor 230 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 230. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof. In some cases, this motion data can be used for enrollment or authentication purposes, as disclosed in further detail herein.

The camera 232 outputs image data reproducible as one or more images (e.g., still images, video images, thermal images, or any combination thereof) that can be stored in the memory device 204. The image data from the camera 232 can be used by the control system 200 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 232 can be used to, for example, identify a location of the user, to determine chest movement of the user, to determine air flow of the mouth and/or nose of the user, to determine a time when the user enters the bed, and to determine a time when the user exits the bed. In some implementations, the camera 232 includes a wide angle lens or a fish eye lens. In some cases, image data from the camera can be used for enrollment or authentication purposes, as disclosed in further detail herein.

The infrared (IR) sensor 234 outputs infrared image data reproducible as one or more infrared images (e.g., still images, video images, or both) that can be stored in the memory device 204. The infrared data from the IR sensor 234 can be used to determine one or more sleep-related parameters during a sleep session, including a temperature of the user and/or movement of the user. The IR sensor 234 can also be used in conjunction with the camera 232 when measuring the presence, location, and/or movement of the user. The IR sensor 234 can detect infrared light having a wavelength between about 700 nm and about 1 mm, for example, while the camera 232 can detect visible light having a wavelength between about 380 nm and about 740 nm.

The PPG sensor 236 outputs physiological data associated with the user that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), a blood oxygen saturation level, or any combination thereof. The PPG sensor 236 can be worn by the user, embedded in clothing and/or fabric that is worn by the user, embedded in and/or coupled to the user device 260, or the like. In some cases, PPG sensor 236 is embedded in and/or coupled to the diagnostic device 280. Such diagnostic devices can be used in Home Sleep Apnea Testing (HSAT) and based on peripheral arterial tonometry (PAT), a technique which has rapidly gained popularity and currently comprise the most widely deployed category of HSAT. Peripheral arterial tonometry-based HSATs obtain most of their sensing modalities from finger photoplethysmography (PPG, which may be the same or similar to PPG sensor 236), from which it derives the blood oxygen saturation (SpO2), pulse rate (PR), and peripheral arterial tonometry. Peripheral arterial tonometry-based HSATs allow for minimally invasive multi-night testing and are available in a fully disposable format. An example of such a system is called NightOwl™, which was described by Massie et al. ("An evaluation of the Night Owl home sleep apnea testing system," Journal of Clinical Sleep Medicine, vol. 14, no. 10, pp. 1791-1796, October 2018, doi: 10.5664/jcsm.7398). It includes a finger probe of the size of a fingertip that senses peripheral arterial tone, together with actigraphy and oximetry, and works with cloud-based analysis software. The analysis determines respiratory-related information, including occurrence of respiratory events (such as obstructive and central apnea events). The device and analyses are described in US2020/0015737A1, WO2021260190A1, and WO2021260192A1, each of which is incorporated herein in its entirety.

The ECG sensor 238 outputs physiological data associated with electrical activity of the heart of the user. In some implementations, the ECG sensor 238 includes one or more electrodes that are positioned on or around a portion of the user during the sleep session. The physiological data from the ECG sensor 238 can be used, for example, to determine one or more of the sleep-related parameters described herein.

The EEG sensor 240 outputs physiological data associated with electrical activity of the brain of the user. In some implementations, the EEG sensor 240 includes one or more electrodes that are positioned on or around the scalp of the user 20 during the sleep session. The physiological data from the EEG sensor 240 can be used, for example, to determine a sleep state and/or a sleep stage of the user at any given time during the sleep session. In some implementations, the EEG sensor 240 can be integrated in the user device 260, the diagnostic device 280, the tag 106, or any combination thereof.

The capacitive sensor 242, the force sensor 244, and the strain gauge sensor 246 output data that can be stored in the memory device 204 and used/analyzed by the control system 200 to determine, for example, one or more of the sleep-related parameters described herein. The EMG sensor 248 outputs physiological data associated with electrical activity produced by one or more muscles. The oxygen sensor 250 outputs oxygen data indicative of an oxygen concentration of gas (e.g., in the conduit 140 or at the user interface 120). The oxygen sensor 250 can be, for example, an ultrasonic oxygen sensor, an electrical oxygen sensor, a chemical oxygen sensor, an optical oxygen sensor, a pulse oximeter (e.g., $SpO_2$ sensor), or any combination thereof.

The analyte sensor 252 can be used to detect the presence of an analyte in the exhaled breath of the user. The data output by the analyte sensor 252 can be stored in the memory device 204 and used by the control system 200 to determine the identity and concentration of any analytes in the breath of the user. In some implementations, the analyte sensor 174 is positioned near a mouth of the user to detect analytes in breath exhaled from the user's mouth. In some implementations, the analyte sensor 252 is a volatile organic compound (VOC) sensor that can be used to detect carbon-based chemicals or compounds. In some implementations, the analyte sensor 174 can also be used to detect whether the user is breathing through their nose or mouth. For example, if the data output by an analyte sensor 252 positioned near the mouth of the user detects the presence of an analyte, the control system 200 can use this data as an indication that the user is breathing through their mouth.

The moisture sensor 254 outputs data that can be stored in the memory device 204 and used by the control system 200. The moisture sensor 254 can be used to detect moisture in various areas surrounding the user (e.g., on or near the diagnostic device 280, between the diagnostic device 280 and the user, on or near the tag 106, between the tag 106 and the user, near the user's face, near and/or within components of a respiratory therapy system, etc.). The moisture sensor 254 can be placed near any area where moisture levels need to be monitored. The moisture sensor 254 can also be used to monitor the humidity of the ambient environment surrounding the user, for example, the air inside the bedroom.

The Light Detection and Ranging (LiDAR) sensor 256 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 256 can measure and map an area extending five meters or more away from the sensor. The LiDAR data can be fused with point cloud data estimated by an electromagnetic RADAR sensor, for example. The LiDAR sensor(s) 256 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 210 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, a non-camera based light sensor, or any combination thereof.

While shown separately in FIG. 1, any combination of the one or more sensors 210 can be integrated in and/or coupled to any one or more of the components of the system 10, including the control system 200, the user device 260, the diagnostic device 280, the tag 106, or any combination thereof. For example, the microphone 220 and the speaker 222 can be integrated in and/or coupled to the user device 260 and the PPG sensor 236 can be integrated in and/or coupled to the diagnostic device 280. In some implementations, at least one of the one or more sensors 210 is not coupled to the diagnostic device 280, the control system 200, the tag 106, or the user device 260, and is positioned generally adjacent to the user during the sleep session (e.g., positioned on or in contact with a portion of the user, worn by the user, coupled to or positioned on the nightstand, coupled to the mattress, coupled to the ceiling, etc.).

The data from the one or more sensors 210 can be analyzed (e.g., by the control system 200) to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), a blood oxygen saturation level, or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, a decreased blood oxygen saturation level, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 210, or from other types of data.

The user device 260 (FIG. 1) includes a display device 262. The user device 260 can be, for example, a mobile device such as a smartphone, a tablet, a gaming console, a smart watch, a laptop, or the like. Alternatively, the user device 260 can be an external sensing system, a television (e.g., a smart television) or another smart home device (e.g., a smart speaker(s) such as Google Home™, Amazon Echo™, Alexa™, etc.). In some implementations, the user device is a wearable device (e.g., a smart watch). The display device 262 is generally used to display image(s) including still images, video images, or both. In some implementations, the display device 262 acts as a human-machine interface (HMI) that includes a graphic user interface (GUI) configured to display the image(s) and an input interface. The display device 262 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 260. In some implementations, one or more user devices can be used by and/or included in the system 10.

In some implementations, the system 10 also includes a diagnostic device 280. As used herein, the term "diagnostic device" is intended to include a device that is capable of collecting sensor data from one or more sensors (e.g., sensor(s) 210), which sensor data can be used for diagnostic purposes. A diagnostic device 280 need not be capable of performing a full diagnosis on its own and may, for example, be suitable for screening, monitoring, or otherwise assessing a physiological condition(s).

In some cases, a diagnostic device 280 can be a device intended for and/or capable of administering and/or controlling therapy. In an example, a diagnostic device 280 can be communicatively coupled to a respiratory therapy system 100 to transmit sensor data or instructions to the respiratory therapy system to facilitate the administration of and/or control of respiratory therapy. In an example, the diagnostic device 280 can be used to identify apnea events, which information can be used by the respiratory therapy system 100 to make an adjustment to the therapy being delivered to the user.

In some cases, the diagnostic device 280 is a wearable diagnostic device, which can be worn (e.g., removably worn) by the user. A wearable diagnostic device can be secured to the user with the aid of components of the wearable diagnostic device (e.g., adhesives and/or bands), with the aid of clothing or accessories, and/or the like, such as described in further detail herein. In some cases, a wearable diagnostic device is a digit-wearable diagnostic device, which is a wearable diagnostic device configured to be worn on a digit (e.g., finger, thumb, toe, etc.) of a user.

While diagnostic devices described herein are often described with reference to being a wearable diagnostic device that is coupled or otherwise attached to a user, that need not always be the case. In some cases, where appropriate, a diagnostic device described herein as being a wearable diagnostic device coupled or otherwise attached to, or directed or otherwise dedicated to, a test subject can be implemented as a non-contact diagnostic device positioned with respect to a test subject.

The diagnostic device 280 is generally used to aid in generating physiological data associated with the user. The diagnostic device 280 can include one or more of the sensors 210 described herein, such as, for example, the motion sensor 138 (e.g., one or more accelerometers and/or gyroscopes), the PPG sensor 154, and/or the ECG sensor 156. The physiological data from the diagnostic device 280 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum he respiration art rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the diagnostic device 280 is coupled or couplable (e.g., electronically or physically) to the user device 260.

In some implementations, the diagnostic device 280 is a wearable device that can be worn by the user, such as a smartwatch, a wristband, a ring, a patch, or a digit probe (e.g., finger probe). The diagnostic device 280 can also be coupled to or integrated a garment or clothing that is worn by the user. Alternatively still, the diagnostic device 280 can also be coupled to or integrated in (e.g., within the same housing) the user device 260. More generally, the diagnostic device 280 can be communicatively coupled with, or physically integrated in (e.g., within a housing), the control system 200, the memory device 204, the tag 106, and/or the user device 260.

In some implementations, the diagnostic device 280 can include a blood pressure device. The blood pressure device is generally used to aid in generating cardiovascular data for determining one or more blood pressure measurements associated with the user. The blood pressure device can include at least one of the one or more sensors 210 to measure, for example, a systolic blood pressure component and/or a diastolic blood pressure component. In some implementations, the blood pressure device is a sphygmomanometer including an inflatable cuff that can be worn by the user and a pressure sensor (e.g., the pressure sensor 212 described herein). For example, the blood pressure device can be worn on an upper arm of the user. In such implementations where the blood pressure device is a sphygmomanometer, the blood pressure device also includes a pump (e.g., a manually operated bulb) for inflating the cuff. In other implementations, the blood pressure device is an ambulatory blood pressure monitor. An ambulatory blood pressure monitor includes a portable recording device attached to a belt or strap worn by the user and an inflatable cuff attached to the portable recording device and worn around an arm of the user. The ambulatory blood pressure monitor is configured to measure blood pressure between about every fifteen minutes to about thirty minutes over a 24-hour or a 48-hour period. The ambulatory blood pressure monitor may measure heart rate of the user at the same time. These multiple readings are averaged over the 24-hour period. The ambulatory blood pressure monitor determines any changes in the measured blood pressure and heart rate of the user, as well as any distribution and/or trending patterns of the blood pressure and heart rate data during a sleeping period and an awakened period of the user. The blood pressure device is generally used to aid in generating physiological data for determining one or more blood pressure measurements associated with a user, for example, a systolic blood pressure component and/or a diastolic blood pressure component. In some implementations, the blood pressure device is an invasive device which can continuously monitor arterial blood pressure of the user and take an arterial blood sample on demand for analyzing gas of the arterial blood. In some other implementations, the blood pressure device is a continuous blood pressure monitor, using a radio frequency sensor and capable of measuring blood pressure of the user once very few seconds (e.g., every 3 seconds, every 5 seconds, every 7 seconds, etc.) The radio frequency sensor may use continuous wave, frequency-modulated continuous wave (FMCW with ramp chirp, triangle, sinewave), other schemes such as PSK, FSK etc., pulsed continuous wave, and/or spread in ultra wideband ranges (which may include spreading, PRN codes or impulse systems).

System 10 can include a tag 106. The tag 106 is an element that includes an authentication feature 108. The authentication feature 108 can be an anti-tamper authentication feature designed to provide authentication that the individual to whom the tag 106 is applied is indeed the intended test subject. The authentication feature 108 can be any feature that is discernable by the user device 260 and/or the diagnostic device 280. The anti-tamper feature(s) of the authentication feature 108 can cause the authentication feature 108 to no longer be suitable for authentication, such as by i) destroying some or all of the authentication feature 108; ii) rendering the authentication feature 108 non-discernable (e.g., not optically visible, not RF detectable, not mechanically distinguishable, etc.); iii) altering the authentication feature 108 to provide a non-authentication signal (e.g., a signal indicative of tampering); or iv) any combination of i-iii.

In some cases, examples of authentication features 108 include i) a mechanical code having a frangible section that irreparably breaks upon removal; ii) an optical code printed on anti-tamper tape that becomes unreadable upon removal; iii) an electrical circuit (or radiofrequency tag) having a frangible section that breaks and disables the circuit (or antenna) upon removal; iv) a key encoded in some form readable by electric contacts or RF signals that is erased or destroyed upon removal or after a certain amount of time has elapsed; v) an optical key printed onto skin of the user that naturally degrades as skin sloughs off; or vi) any combination of i-v.

In some cases, tag 106 can be a transmitting tag. A transmitting tag can include a transmitter (e.g., an RF transmitter, a light emitting diode, a speaker, etc.) capable of transmitting a signal (e.g., an authentication signal). The signal can be an encoded signal, although that need not always be the case. The transmitted signal, when received, can be indicative of authentication. In such cases, an electronic or physical feature of the tag 106 can cause the transmitter to cease functioning, to cease transmitting the correct signal, or to transmit a non-authentication signal in response to removal of the tag 106 from the user. A transmitting tag can be implemented in any suitable housing, such as a wristband, a pendant, a collar, a watch, an article of clothing, an adhesive sticker, or the like. In some cases, a transmitting tag can include its own power source, such as a battery. In some cases, however, a transmitting tag can receive power from a nearby transmitter, such as a transmitter in a user device 260 or diagnostic device 280. In some cases, the transmitting tag can transmit its signal by altering a received signal when reflecting the received signal.

In an example of a transmitting tag, an RF transmitter can be integrated into a wristband which can be secured around a wrist of an intended test subject. The wristband can be configured such that removal of the wristband can only be accomplished by breaking the wristband, which in turn breaks a portion of the RF transmitter, causing the wristband to cease transmitting the authentication signal. Thus, when the wristband is applied to an intended test subject by a trusted individual, it can be assumed that the wristband is still applied to that intended test subject as long as it continues transmitting its authentication signal.

In some cases, a tag 106 can be a non-transmitting tag. A non-transmitting tag can include an authentication feature 108 in the form of an authentication signal encoded on the tag 106 itself, such as in the form of a barcode, text, a mechanically encoded structure (e.g., a keyway that takes on a particular shape indicative of authentication), or the like. In some cases, a tag 106 can be implemented as an imprint (e.g., a henna tattoo) applied to a user's skin, as a sticker (e.g., a sticker with a barcode attached to the user's skin), or the like. Anti-tamper feature(s) of the authentication feature 108 can cause the authentication signal to become destroyed or otherwise undiscernible upon removal of the tag 106 from the user to which it was applied. For example, intentional weak points in a sticker can act as failure points such that attempts to remove the sticker from the user's skin would cause the sticker to split into multiple pieces, thus destroying the authentication signal.

In some cases, tag 106 can be a smart tag. A smart tag includes a control system (e.g., control system 200) for determining whether or not to issue an authentication signal. For example, a smart tag can include one or more sensors designed to determine the identity of the user to which it is attached, such as described in further detail with reference to the diagnostic device. If the determined identity matches the intended test subject, the smart tag can issue an authentication signal. In some cases, if a smart tag detects that the tag 106 is no longer coupled to the intended user (e.g., by detecting unexpected signals in the one or more sensors, such as unexpected light at a sensor secured against the user's skin), it can cease issuing an authentication signal and/or issue a non-authentication signal.

As used herein, an authentication signal can include an authentication key. An authentication key can include i) a non-unique identifier; ii) a unique identifier; iii) an encryption key; or iv) any combination if i-iii. In some cases, an authentication key of a tag 106 can be matched with an enrollment authentication key (e.g., an authentication key acquired during enrollment of a test subject as disclosed in further detail herein). In such cases, successfully authenticating the tag with a diagnostic wearable device includes matching the authentication key with the enrollment authentication key. Matching an authentication key with an enrollment authentication key includes i) determining that the keys have the same value; or ii) determining that the keys are complementary to one another (e.g., one key can decode a message cryptographically encoded with the other key).

In some cases, tag 106 can be used to physically facilitate securing the diagnostic device 280 to a user. For example, a tag 106 in the form of a band can be used to physically hold a diagnostic device 280 against skin of a user.

In some tag 106 example cases, removing the tag 106 could destroy a critical piece of an RF circuit (e.g., an antenna, an oscillator, a modulator, an encoder, an amplifier, a demodulator, a phase locked loop, a mixer, a data converter (e.g., analog-to-digital converter or digital-to-analog converter), an integrated circuit, an application-specific-integrated-circuit, a power source, or the like). In such cases, a lack of a signal identifies the tampering. In some cases, the signal, a handshake, a beacon, or the like, changes some aspect of the transmission or bidirectional communication (e.g., rolls a cryptographic key, changes a frequency, changes a modulation, etc.) if a tampering is detected. In some cases, tampering could be indicated by a change in resistance (e.g., including an open or short circuit), a change in inductance, a change in capacitance, or the like, from an expected or reference value. In some cases, a RFID tag can be read by a reader in the diagnostic device. In some cases, both a tag and a diagnostic device could contain pseudo random number generators that are synchronized, and rolling/hopping codes can be used to associate the tag with the diagnostic device.

While the control system 200 and the memory device 204 are described and shown in FIG. 1 as being a separate and distinct component of the system 10, in some implementations, the control system 200 and/or the memory device 204 are integrated in the user device 260, the diagnostic device 280, the tag 106, or any combination thereof. Alternatively, in some implementations, the control system 200 or a portion thereof (e.g., the processor 202) can be located in a cloud (e.g., integrated in a server, integrated in an Internet of Things (IOT) device, connected to the cloud, be subject to edge cloud processing, etc.), located in one or more servers (e.g., remote servers, local servers, etc.), located in a separate component (e.g., a respiratory therapy system), or any combination thereof (including in combinations with any of the user device 260, the diagnostic device 280, and the tag 106).

While system 10 is shown as including all of the components described above, more or fewer components can be included in a system according to implementations of the present disclosure. For example, a first alternative system includes the control system 200, the memory device 204, and at least one of the one or more sensors 210 and does not include the tag 106. As another example, a second alternative system includes the control system 200, the memory device 204, at least one of the one or more sensors 210, the user device 260, and the diagnostic device 280. As yet another example, a third alternative system includes the control system 200, the memory device 204, the diagnostic device 280, at least one of the one or more sensors 210, and the tag 106. Thus, various systems can be formed using any portion or portions of the components shown and described herein and/or in combination with one or more other components.

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes up and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smartphone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 262 of the user device 260 to manually initiate or terminate the sleep session.

Generally, the sleep session includes any point in time after the user has laid or sat down in bed (or another area or object on which they intend to sleep), and has turned on or otherwise initiated data collection from the diagnostic device 280. The sleep session can thus include time periods (i) when the user is using the diagnostic device 280, but before the user attempts to fall asleep (for example when the user lays in the bed reading a book); (ii) when the user begins trying to fall asleep but is still awake; (iii) when the user is in a light sleep (also referred to as stage 1 and stage 2 of non-rapid eye movement (NREM) sleep); (iv) when the user is in a deep sleep (also referred to as slow-wave sleep, SWS, or stage 3 of NREM sleep); (v) when the user is in rapid eye movement (REM) sleep; (vi) when the user is periodically awake between light sleep, deep sleep, or REM sleep; or (vii) when the user wakes up and does not fall back asleep.

The sleep session is generally defined as ending once the user removes or otherwise ceases data collection via the diagnostic device 280 and gets out of bed, although that need not always be the case. In some implementations, the sleep session can include additional periods of time, or can be limited to only some of the above-disclosed time periods. For example, the sleep session can be defined to encompass a period of time beginning when the diagnostic device 280 begins collecting sensor data, ending when the diagnostic device 280 ceases to collect sensor data or when a determination is made that disauthentication event has occurred (e.g., the diagnostic device 280 was removed from the user), and including some or all of the time points in between, when the user is asleep or awake.

A testing session can be defined as a period of time during which sensor data is being collected by the diagnostic device 280. In some cases, a testing session can begin and end at the same time as the sleep session or based on (e.g., at the same time as or offset from) the start and/or ending times of a sleep session, or based on any other named times associated with the sleep session. In some cases, a testing session can be manually started and/or stopped. In some cases, a testing session can be automatically started in response to authenticating of the diagnostic device 280 with the testing subject (e.g., the user wearing the diagnostic device). In some cases, a testing session can be automatically paused, and/or ended in response to detection of a disauthentication event (e.g., the user removes the diagnostic device 280).

Figure 2:
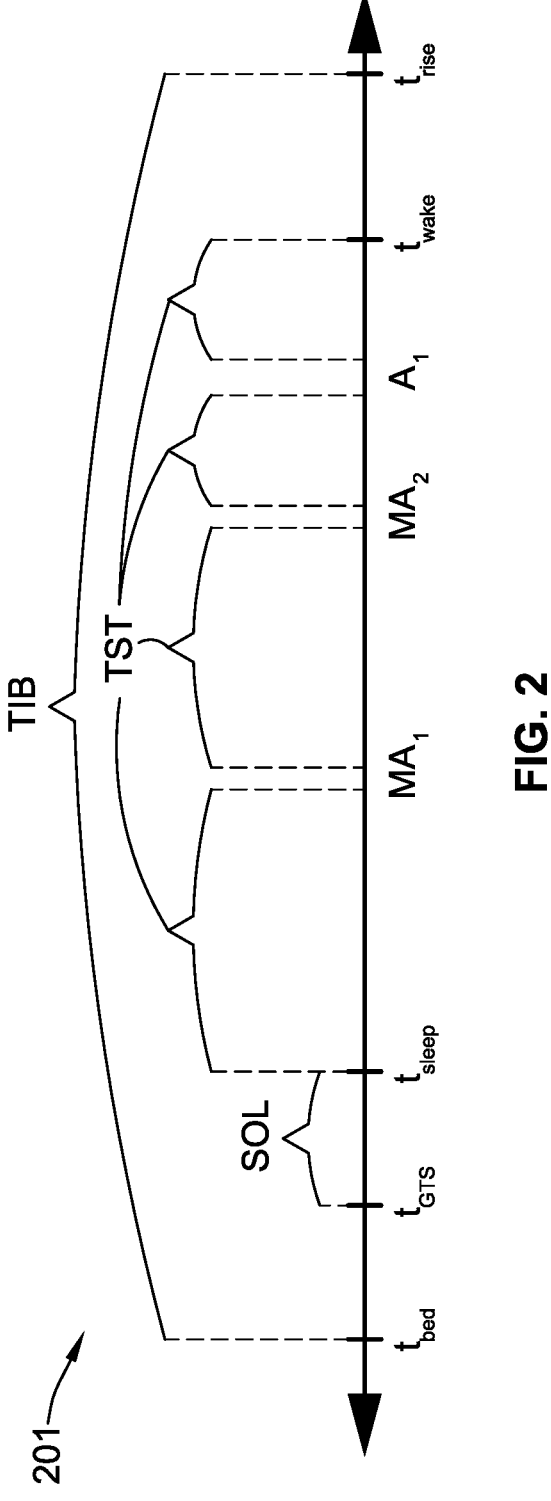
FIG. 2 illustrates an exemplary timeline for a sleep session, according to some implementations of the present disclosure.

Referring to the timeline 201 in FIG. 2 the enter bed time $t_{bed}$ is associated with the time that the user initially enters the bed prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 260, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 201 of FIG. 2, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 3:
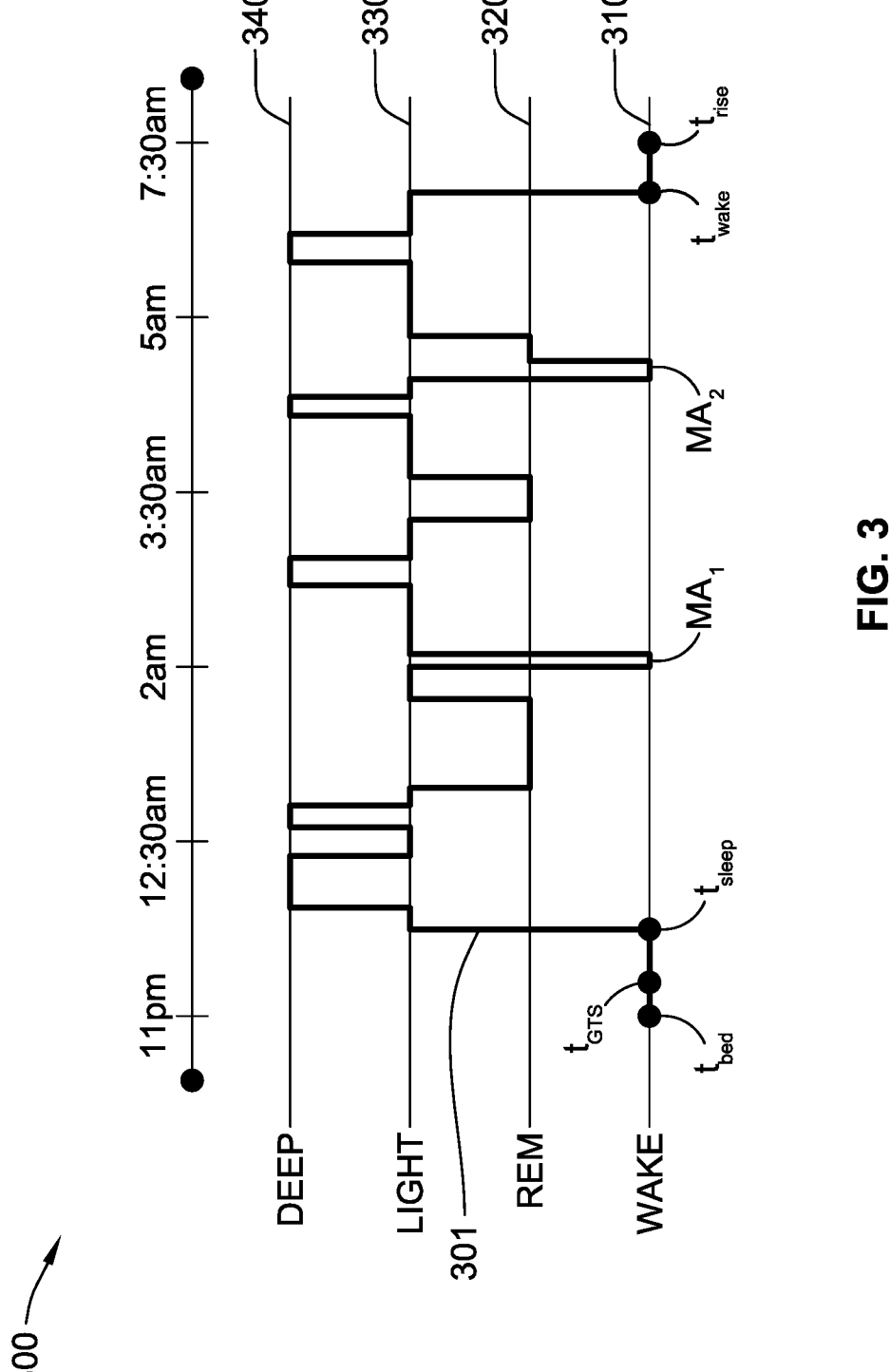
FIG. 3 illustrates an exemplary hypnogram associated with the sleep session of FIG. 7, according to some implementations of the present disclosure.

Referring to FIG. 3, an exemplary hypnogram 300 corresponding to the timeline 201 (FIG. 2), according to some implementations, is illustrated. As shown, the hypnogram 300 includes a sleep-wake signal 301, a wakefulness stage axis 310, a REM stage axis 320, a light sleep stage axis 330, and a deep sleep stage axis 340. The intersection between the sleep-wake signal 301 and one of the axes 310-340 is indicative of the sleep stage at any given time during the sleep session.

The sleep-wake signal 301 can be generated based on physiological data associated with the user (e.g., generated by one or more of the sensors 210 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 300 is shown in FIG. 3 as including the light sleep stage axis 330 and the deep sleep stage axis 340, in some implementations, the hypnogram 300 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 204.

The hypnogram 300 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 2), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 2), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 210 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 218, the microphone 220, the camera 232, or any combination thereof. The go-to-sleep time can be determined based on, for example, data from the motion sensor 218 (e.g., data indicative of no movement by the user), data from the camera 232 (e.g., data indicative of no movement by the user and/or that the user has turned off the lights) data from the microphone 220 (e.g., data indicative of the user turning off a TV), data from the user device 260 (e.g., data indicative of the user no longer using the user device 260), data from the diagnostic device 280, data from the tag 106, or any combination thereof.

Figure 4:
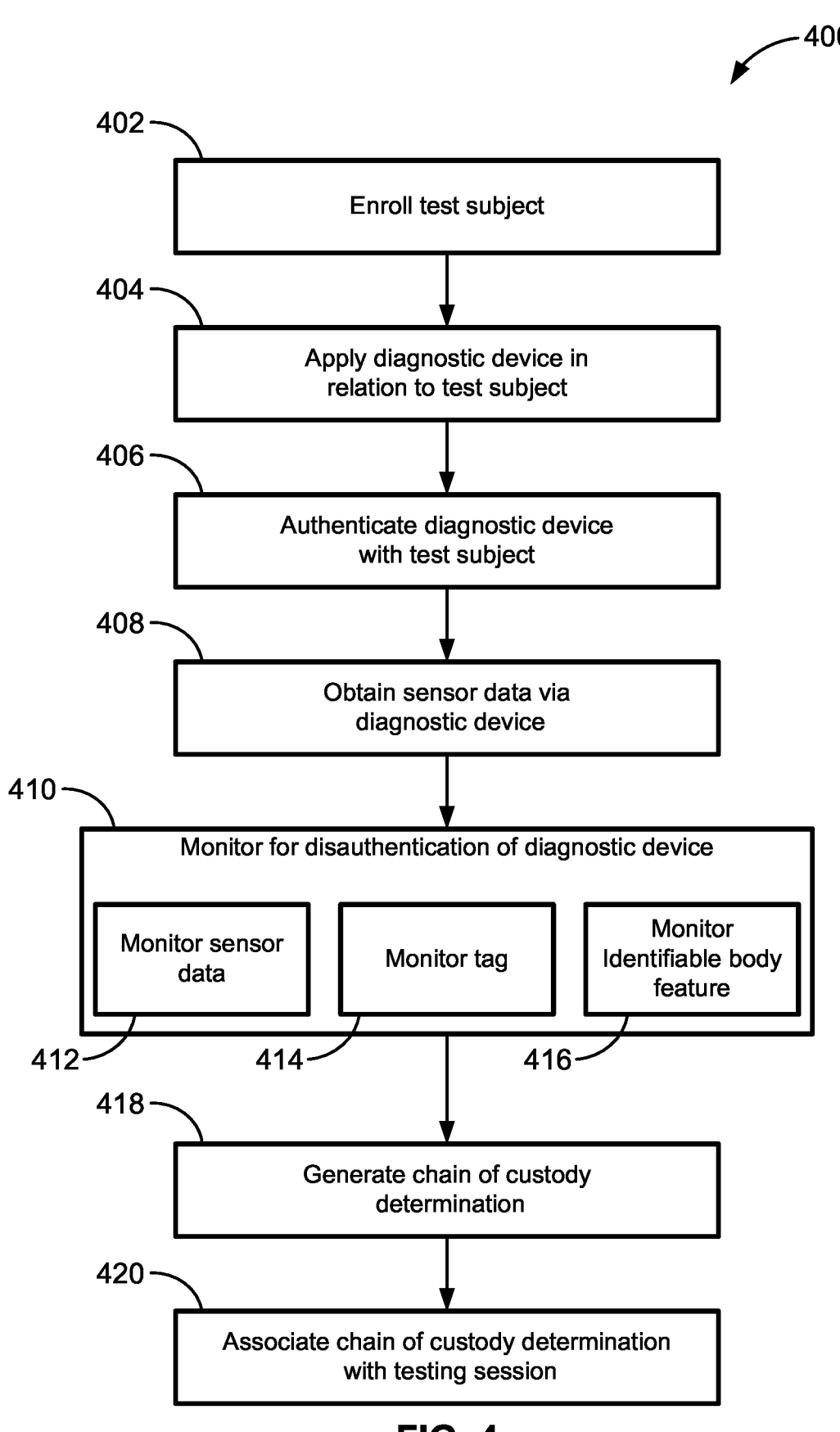
FIG. 4 is a flowchart depicting a process for managing a digital chain of custody, according to certain aspects of the present disclosure.

FIG. 4 is a flowchart depicting a process 400 for managing a digital chain of custody, according to certain aspects of the present disclosure. Process 400 can be implemented on system 10 of FIG. 1.

At block 402, a test subject is enrolled. Enrolling a test subject can include associating a test subject with a testing session. Enrolling the test subject can include identifying the test subject as an intended test subject. In some cases, identifying the test subject as the intended test subject can include collecting sensor information (e.g., image data from a camera) of the individual and comparing it with known information (e.g., an image of the intended test subject as accessed from a database) or acquired information (e.g., an image of the given test subject's identification, such as a government-issued identification card, which also includes information associated with the intended test subject, such as name, address, and/or date of birth).

In some cases, enrolling a test subject occurs in a trusted location and/or with a trusted individual. For example, a test subject can be enrolled at a doctor's office by a physician. The physician can positively confirm that the test subject is indeed the intended test subject. In some cases, the trusted individual can apply a tag to the test subject, which can be further used to confirm chain of custody as long as the tag remains applied to the test subject, even after the test subject leaves the presence of the trusted individual and/or leaves the trusted location. In some cases, a test subject can be enrolled under observation by a trusted individual, such as via a video chat with a trusted individual. The trusted individual can confirm that the test subject is the intended test subject over the video chat.

In some cases, enrolling a test subject occurs at the test subject's home or other personal location. In such cases, an app on a user device can guide the test subject through the enrollment process. In an example, a user installs an app on their smartphone and begins the enrollment process. The app may ask the user to take a photograph of, or otherwise scan, their driver's license or other identification. The app may then ask the user to take a photograph of their own face. The app can then compare the photograph on the driver's license with that of the test subject's own face to confirm that the given test subject is indeed the intended test subject. Further comparison of other details on the driver's license can further confirm that the given test subject is indeed the intended test subject.

At block 404, a diagnostic device is applied in relation to the test subject. In some cases, a diagnostic device is applied to the test subject, such as a wearable device (e.g., a finger-worn device). In some cases, however, the diagnostic device can be placed spaced apart from the test subject, but positioned to nevertheless collect sensor data associated with the test subject (e.g., a non-contact sensor, such as a microphone or LIDAR sensor). In some cases, applying a diagnostic device to a test subject includes applying the diagnostic device to a digit of the test subject, such as a toe, finger, or thumb of the test subject. Other body parts can also be used (e.g., earlobe).

In some cases, applying the diagnostic device to a test subject can occur at the same time as enrolling the test subject at block 402. In some cases, applying the diagnostic device to the test subject can occur in the presence of a trusted individual, such as a doctor confirming the identity of the test subject and applying the diagnostic device to the test subject at that time. In such cases, removal of the diagnostic device after it has been applied may be indicative of a possible break in the chain of custody.

At block 406, the diagnostic device is authenticated with the test subject. Authenticating the diagnostic device can include making a determination that the diagnostic device is collecting sensor data from (e.g., is worn by) the test subject and not another individual. In some cases, authenticating the diagnostic device includes establishing a communication link between the diagnostic device and another device, such as a user device.

Authenticating the diagnostic device can include acquiring sensor data from the diagnostic device and comparing it with sensor data acquired from another device (e.g., a user device). In an example, a user may place the diagnostic device on their finger prior to enrolling. In such an example, the process of enrolling may include obtaining image data of the test subject's face. In this example, the diagnostic device can be authenticated at the same time by obtaining continuous image data of the test subject's face and body parts connecting the test subject's face to the diagnostic device. For example, if the diagnostic device is worn on the first finger of the left hand, this continuous image data may include a single photo showing the test subject's face, neck, upper torso, shoulder, upper left arm, lower left arm, left hand, first finger on the left hand, and the diagnostic device. In some cases, continuous image data can include a first image depicting the test subject's face and sequential image data (e.g., video data) panning down the test subject's neck, along the upper torso and shoulder, along the left arm and hand, and along the finger up to the diagnostic device.

In some cases, authenticating the diagnostic device can include determining an approximate distance to the diagnostic device. When the approximate distance is within a threshold value, a determination can be made that the diagnostic device is likely worn by the test subject. Determining a distance to the diagnostic device can be based on sensor data from the diagnostic device, sensor data from a user device, and/or other sensor data. In some cases, a distance can be determined via LIDAR, RADAR, an RF signal strength (e.g., a WiFi received signal strength), or the like.

In some cases, the diagnostic device can output a signal (e.g., an encoded light signal or an encoded auditory signal) that can be sensed by another device (e.g., the user device). In such cases, when the diagnostic device's output signal is detected by the other device, a determination can be made that the correct diagnostic device is the one associated with the intended test subject. For example, when a diagnostic device is authenticated by video data, a unique output signal can be output by the diagnostic device (e.g., as an infrared flash pattern) and detected by the camera of the user device. The system can use that output signal to associate the correct diagnostic device with the test subject appearing in the video data. Thus, when multiple diagnostic devices are available, whichever diagnostic device is placed on the test subject's finger can be identified by the system, via e.g., a readable code on or emitted by the diagnostic device and detected by the user device (e.g., smart phone) as described further herein, ensuring that sensor data from the other diagnostic device is not inadvertently associated with the test subject.

In another example, physiological parameters associated with the test subject can be acquired via multiple routes including at least the diagnostic device. In such an example, the test subject's smart phone may acquire breathing information (e.g., respiration rate) and a heart rate by analyzing the image data of the test subject's face by methods known in the art. Separately, the system can acquire breathing information and heart rate from one or more sensors of the diagnostic device. Then, by comparing the physiological parameters from the smart phone with those from the diagnostic device, a determination can be made such that when the physiological parameters sufficiently match (e.g., match exactly or within a threshold margin of error), it is indicative that the individual depicted in the image data (e.g., which may have been used during enrollment at block 402) is the same individual as the one wearing the diagnostic device.

In another example, sensor data (e.g., movement data) from the diagnostic device can be compared with expected sensor data (e.g., expected movement data). The expected sensor data can come from one or more separate sensors (e.g., expected movement data can be extracted from live camera data of the test subject making movements) or can be predetermined (e.g., expected movement data can be based on an instruction by the app for the test subject to make a certain movement). In an example, an app may instruct the test subject to wave in a discernable fashion using the same hand to which the diagnostic device is connected. Movement data detected by the diagnostic device can then be used to make a determination that the individual making the movements is the same individual wearing the diagnostic device. In such an example, if the expected movement data is extracted from image data of the enrolled test subject or during enrollment of the test subject, it can be determined that the individual wearing the diagnostic device is indeed the intended test subject.

In some cases, authenticating the diagnostic device with the test subject can include identifying the test subject by comparing sensor data acquired via the diagnostic device with known data. For example, the diagnostic device can acquire sensor data indicative of the test subject's fingerprint, which can then be compared with a known fingerprint of the intended test subject (e.g., as acquired from a previously established database). In another example, the diagnostic device can determine one or more physiological parameters (e.g., heart rate, respiration rate, blood oxygen saturation, and movement data over time) which can be compared with known physiological parameters already associated with the intended test subject. For example, physiological parameters for an intended test subject can be collected over time and used to train a machine learning model. Thereafter, current physiological parameters acquired from the diagnostic device can be fed into the machine learning model to make a determination as to whether or not the current physiological parameters are likely from the intended test subject. Thus, an intended test subject's own physiological "fingerprint" (e.g., how one or more physiological parameters change over time and/or change in relation to one another) can be used to confirm that the diagnostic device is indeed collecting sensor data from that intended test subject.

In some cases, authenticating a diagnostic device at block 406 can include interacting the diagnostic device with a tag (e.g., tag 106 of FIG. 1). The diagnostic device can read or otherwise receive the authentication signal from the tag, thus confirming that the diagnostic device is being associated with the intended test subject. For example, the tag may be a sticker placed on a finger pad of the user, and the diagnostic device may be placed over that finger pad such that the diagnostic device can optically read a barcode on the tag while also obtain sensor data from the test subject. The barcode read by the diagnostic device can now be associated with the tag, which is associated with the intended test subject.

In another example, a tag can take the form of a mechanical device coupled to a finger of the user. The mechanical device can include a mechanically encoded structure that interacts with the diagnostic device (e.g., a set of detents that match a set of pins of the diagnostic device). When the diagnostic device detects the correct mechanically encoded structure, an inference can be made that the diagnostic device can be associated with the tag, which is associated with the intended test subject. In some cases, such an inference can be used to enable the diagnostic device (e.g., power to circuits of the diagnostic device is prohibited until the diagnostic device interfaces with the mechanically encoded structure), to enable sensing by the diagnostic device (e.g., sensing is disabled until the diagnostic device interfaces with the mechanically encoded structure), or the like.

In some cases, authenticating a diagnostic device at block 406 can include scanning (e.g., via a camera of a user device) a quick reference (QR) code or other discernable feature of the diagnostic device to identify the diagnostic device (e.g., when multiple diagnostic devices are in range).

At block 408, sensor data can be obtained via the diagnostic device. In some cases, sensor data can also or alternatively be obtained as part of blocks 402, 404, 406, and/or otherwise. Obtaining sensor data can include collecting sensor data from one or more sensors of the diagnostic device. In some cases, collecting sensor data at block 408 can be based at least in part on authenticating the diagnostic device at block 406. In some cases, collecting sensor data can be disabled or otherwise prohibited until the diagnostic device has been authenticated at block 406. In some cases, sensing can begin in response to authentication of the diagnostic device. In some cases, sensor data acquired at block 408 can be marked as valid and/or can be associated with the intended test subject and/or a testing session only after authentication of the diagnostic device.

Acquired sensor data can be stored and/or processed by the diagnostic device and/or can be transmitted for storage and/or processing by another device (e.g., a user device).

At block 410, the system can monitor for disauthentication of the diagnostic device. Disauthentication of the diagnostic device is an indication of a potential break in the diagnostic chain of custody. Disauthentication of the diagnostic device indicates that the diagnostic device has or may have been removed from the test subject and/or otherwise collecting sensor data from someone other than the intended test subject. In some cases, monitoring for disauthentication can be referred to as monitoring to identify an interference instance. An interference instance can be any event that is indicative that the diagnostic device may no longer be collecting sensor data from the intended test subject (e.g., the diagnostic device was removed from the intended test subject and coupled to another individual).

Monitoring for disauthentication can include monitoring sensor data at block 412, monitoring a tag at block 414, monitoring an identifiable body feature at block 416, or the like. In some cases, an action that is used to authenticate the diagnostic device at block 406 can be used to disauthentication the diagnostic device. For example, if authentication of the diagnostic device is based on image data depicting the diagnostic device on the body of the intended test subject, disauthentication can be identified based on image data depicting the diagnostic device no longer on the body of the intended test subject (e.g., on another individual's body).

In some cases, monitoring for disauthentication of the diagnostic device includes monitoring sensor data at block 412. Monitoring sensor data includes monitoring the raw sensor data or physiological parameters derived from the raw sensor data. In some cases, monitoring the sensor data can include monitoring the sensor data for a gap. For example, the diagnostic device may normally acquire a blood oxygen saturation level two hundred times a second (e.g., 200 Hz), but the system may detect a five second gap where blood oxygen saturation levels could not be obtained. Detection of this gap may be indicative that the diagnostic device is no longer on the same test subject. In some cases, detection of a gap at the same time as a drop in connectivity (e.g., a drop in the wireless connection between the diagnostic device and the user device) may be instead indicative of a drop in connectivity, in which case a disauthentication determination may be not made or may be made only with additional support.

In some cases, monitoring the sensor data can include monitoring the sensor data for a substantial change in the raw sensor data or the derived physiological parameters. For example, a test subject's blood pressure may be monitored periodically, and may generally remain within the range of 135-145 over 80-90. If the system starts detecting blood pressures that are generally in the range of 110-120 over 65-75, it may be indicative that the diagnostic device is no longer on the same test subject.

In some cases, monitoring the sensor data can include monitoring the sensor data to identify the individual associated with the sensor data based on known data. For example, physiological parameters derived from the sensor data can be passed into a machine learning model that has been trained on the intended test subject's historical physiological parameters, and a determination can be made as to whether or not the source of the sensor data is the intended test subject. If the determination is that the source of the sensor data is not the intended test subject, a disauthentication inference can be made.

In some cases, monitoring for disauthentication can occur by monitoring a tag at block 414. Monitoring a tag at block 414 can include acquiring sensor data of the tag, such as via the diagnostic device or via a user device. Acquiring sensor data of the tag can include receiving an authentication signal (e.g., an actively transmitted RF signal or a passively read barcode) from the tag. In some cases, when the authentication signal is detected, an inference can be made that the chain of custody has not been broken. In some cases, when the authentication signal is no longer detected or when a disauthentication signal is detected, an inference can be made that disauthentication has occurred. For example, if a test subject attempts to remove a tag in the form of a wristband, removal of the wristband may disable the authentication feature, thus causing the wristband to no longer transmit its authentication signal. Upon detecting continued absence of the authentication signal, a determination can be made that the diagnostic device may no longer be on the intended test subject and/or the test can be otherwise considered invalid, at least as of the time the determination is made.

In some cases, monitoring for disauthentication can include monitoring an identifiable body feature at block 416. Any suitable identifiable body feature can be identified, such as a fingerprint or portion thereof, a digitprint (e.g., a pattern of loops and whorls on a toe, finger, or thumb) or portion thereof, a pattern of skin on the body (e.g., at or near a finger), or any other uniquely identifiable feature of the intended test subject. Monitoring an identifiable body feature can include acquiring sensor data (e.g., from the diagnostic device or from another device such as a user device) of the identifiable body feature and comparing it with known data of the identifiable body feature. Known data can include data acquired from a prepopulated database (e.g., a database of known fingerprints or a database of fingerprints previously collected at a trusted location). In some cases, known data can include data acquired from the diagnostic device or other device (e.g., user device) during enrollment of the test subject at block 402 and/or authentication of the diagnostic device at block 406.

In some cases, monitoring for disauthenticaiton can occur continuously or regularly (e.g., every five minutes). In some cases, monitoring for disauthentication can occur at predetermined times, such as at the end of a testing session. A testing session and/or associated test data can be considered valid (e.g., the diagnostic chain of custody is continuous) between when both the test subject was enrolled and the diagnostic device was authenticated (e.g., a first time) and when the disauthentication was detected (e.g., a second time). When continuous monitoring is used, the disauthentication event can be detected immediately. When regular monitoring is used, a disauthentication event may have occurred sometime between the previous regular interval and the current regular interval in which disauthentication was detected. When monitoring only occurs at preset times, a disauthentication event may have occurred anytime between the previous monitoring time and the current monitoring time in which disauthentication was detected. In cases where disauthentication is only monitored at the end of the testing session, detection of disauthentication at that time may be cause to invalidate the entire testing session.ad In some cases, communications between different devices (e.g., diagnostic device and user device, diagnostic device and respiratory therapy system, or the like) can be protected from bad actors, such as through the use of cryptographic keys and the like. Use of cryptographic keys can ensure communications between the diagnostic device and the user device are not forged, modified, or otherwise interfered with. In some cases, actions taken or sensor data acquired during enrollment at block 402 and/or authentication at block 406 can be used to establish cryptographic keys on one or more devices, such as on each device.

At block 418, a chain of custody determination can be generated. Generating the chain of custody determination can be based on the identification of any disauthentication events (e.g., interference instances) at block 410. If no disauthentication events were detected, the chain of custody determination can be indicative that the entire testing session was valid. If a disauthentication event was detected, the chain of custody determination can indicate the disauthentication event. In some cases, if a disauthentication event was detected, the chain of custody determination can indicate that the testing session was valid from the start of the testing session up until the disauthentication event was detected.

In some cases, a chain of custody determination can indicate a confidence value associated with a period of time or a set of sensor data. The confidence value can be an indication as to how confident the system is that the sensor data is associated with the intended test subject. For example, if no disauthentication event is detected, the confidence value can be 100% for the entire testing session. If a disauthentication event is detected, the confidence value for the period of time from the start of the testing session up to the disauthentication event may be 100%, whereas the confidence value for the period of time after the disauthentication event up to the end of the testing session may be 30%. The confidence value can be based on the determination of the disauthentication event at block 410. For example, if sensor data is monitored and it is determined that the sensor data is not likely from the intended test subject, the confidence interval may be moderate (e.g., 50%). However, if an identifiable body feature being monitored is no longer detected at all, the confidence interval may be lower (e.g., 20%), as the lack of the identifiable body feature may be a more likely indication that the diagnostic device is no longer on the intended test subject than a change in sensor data.

In some cases, the confidence value can be used to apply a weighting value to the sensor data when analyzing the sensor data at a later time, such as when analyzing the sensor data to determine a diagnosis. For example, sensor data associated with a low confidence value may have a relatively low weighting as compared to sensor data associated with a high confidence value.

Generating the chain of custody determination can occur dynamically (e.g., in realtime) or at a predetermined time (e.g., after the end of a testing session). For example, if determined in realtime, a chain of custody determination can be used to present a warning message or notification to the test subject and/or a caretaker (e.g., a physician who ordered the test or a parent conducting the test on a child). For example, upon identifying a disauthentication event, a notification can be presented that indicates that the test is currently noncompliant because the diagnostic chain of custody is no longer continuous. In some cases, in response to such a notification, a test subject can reauthenticate the diagnostic device using a procedure similar to or the same as initially authenticating the diagnostic device at block 406.

In some cases, identifying a disauthentication event at block 410 and/or generating a chain of custody determination at block 418 can be based at least in part on a physiological parameter, such as AHI. For example, when the sensor data indicates that a user's AHI is especially high, an assumption can be made that the user is likely not attempting to cheat the system since the result is worse than average, and thus identification of a disauthentication event may require a more substantial showing and/or confidence values may be adjusted accordingly.

At block 420, the chain of custody determination can be associated with the testing session. In some cases, associating the chain of custody determination with the testing session can include associating the chain of custody determination with sensor data collected at block 408. In some cases, if the chain of custody determination generated at block 418 is indicative that only certain periods of time within the testing session are considered valid, associating the chain of custody determination with the testing session and/or the sensor data can occur for only those periods of time considered valid.

In some cases, a data associated with a testing session can include i) enrollment data associated with enrollment of the intended test subject; ii) authentication data associated with authentication of the diagnostic device; iii) sensor data collected via the diagnostic device; iv) additional sensor data collected via a device other than the diagnostic device; v) disauthentication data (e.g., information about identified disauthentication events); vi) chain of custody data (e.g., chain of custody determination(s)); or vii) any combination of i-vi.

While process 400 is depicted with certain blocks in a certain order, process 400 can be implemented with fewer, additional, or different blocks, and in different orders. For example, in some cases, enrolling the test subject and authenticating the diagnostic device occur simultaneously. In another example, authenticating the diagnostic device occurs prior to enrolling the test subject. In another example, sensor data obtained via the diagnostic device occurs prior to authenticating the diagnostic device, and/or before enrolling the test subject. In such an example, a test subject may wear the diagnostic device from the start of a testing session to an end time, at which point the test subject may the perform enrollment for the first time and/or authentication of the diagnostic device for the first time. As long as the system can confirm that the diagnostic device was continuously collecting sensor data from the same individual, once the system identifies the individual as the intended test subject (even if that identification occurs after sensor data is collected), a chain of custody determination can be made concluding that the testing session was valid (e.g., chain of custody was continuous and the original test subject for whom sensor data was being collected is indeed the intended test subject).

In some cases, in addition to chain of custody determinations, a determination can be made about whether or not the test subject sufficiently engaged in a sleep session during the testing session. For example, if physiological parameters indicate that the test subject was in an awake sleep state throughout the testing session, the testing session can be flagged or otherwise indicated as non-valid for purposes of identifying sleep-related disorders.

In some cases, a diagnostic device (e.g., diagnostic device 280 of FIG. 1) can be used by a user of a respiratory therapy system (e.g., respiratory therapy system 100 of FIG. 1). In such cases, the diagnostic device can collect sensor data usable to determine how the user is sleeping when on respiratory therapy and/or when not on respiratory therapy. In some cases, such sensor data can be used to demonstrate to a user that the individual's sleep disorder breathing (e.g., obstructive sleep apnea) is suitable controlled and/or managed by the respiratory therapy. In these types of cases, maintaining a provable chain of custody (e.g., as described with reference to process 400) can be used to ensure that the sensor data associated with the diagnostic device is indeed from the same individual partaking in respiratory therapy. In some cases, sensor data from the respiratory therapy system (e.g., respiratory therapy system 100 of FIG. 1) can be compared with that of the diagnostic device to ensure the diagnostic device is indeed collecting data from the same individual partaking in the respiratory therapy.

In some cases, proving compliance with respiratory therapy and/or proving therapy efficacy can be important for certain individuals. For example, a safety critical individual may be required to make use of respiratory therapy when sleeping as part of their job duties, especially if that individual has diagnosed SDB. In such cases, the chain of custody determination generated at block 418 can be used to confirm that the individual made use of respiratory therapy and/or that the individual's use of respiratory therapy was effective (e.g., when the sensor data from the diagnostic device show the user experienced fewer than a threshold number of events, such as apnea events, during a sleep session). Thus, the chain of custody determination can benefit both the diagnostic phase (e.g., home sleep testing to diagnose SDB) and subsequent therapy (e.g., respiratory therapy). In some cases, the chain-of-custody-proven sensor data from the diagnostic device can ensure a user's sleep-related parameters are within desired thresholds (e.g., a residual AHI below a threshold, a total sleep time above a threshold, a total time spent in a particular sleep stage above a threshold, and the like) to approve that user for work.

In some cases, when used with a respiratory therapy device, process 400 can include authenticating the respiratory therapy system with the test subject. Authenticating the respiratory therapy system with the test subject can occur similarly to authenticating the diagnostic device at block 406. In some cases, a user can be prompted to put on a user interface (e.g., user interface 120 of FIG. 1) and make certain movements that can be detected by another device (e.g., a user device) to authenticate the respiratory therapy system. Other techniques as disclosed herein with reference to authenticating a diagnostic device can be used with a respiratory therapy system (e.g., authenticating via a tag, via wireless signals, etc.).

Likewise, in some cases process 400 can include monitoring for disauthentication of the respiratory therapy system, which can occur similarly to monitoring for disauthentication of the diagnostic device described with reference to block 410. For example, sensor data acquired by the respiratory therapy system can be monitored to identify a likely mask-off event. In some cases, a disauthentication event, such as a mask-off event, can result in a determination that the chain of custody is broken at that time, and/or can result in a prompt for the user to re-authenticate the respiratory therapy system. Other techniques as disclosed herein with reference to monitoring a diagnostic device for disauthentication can be used with a respiratory therapy system.

Figure 5:
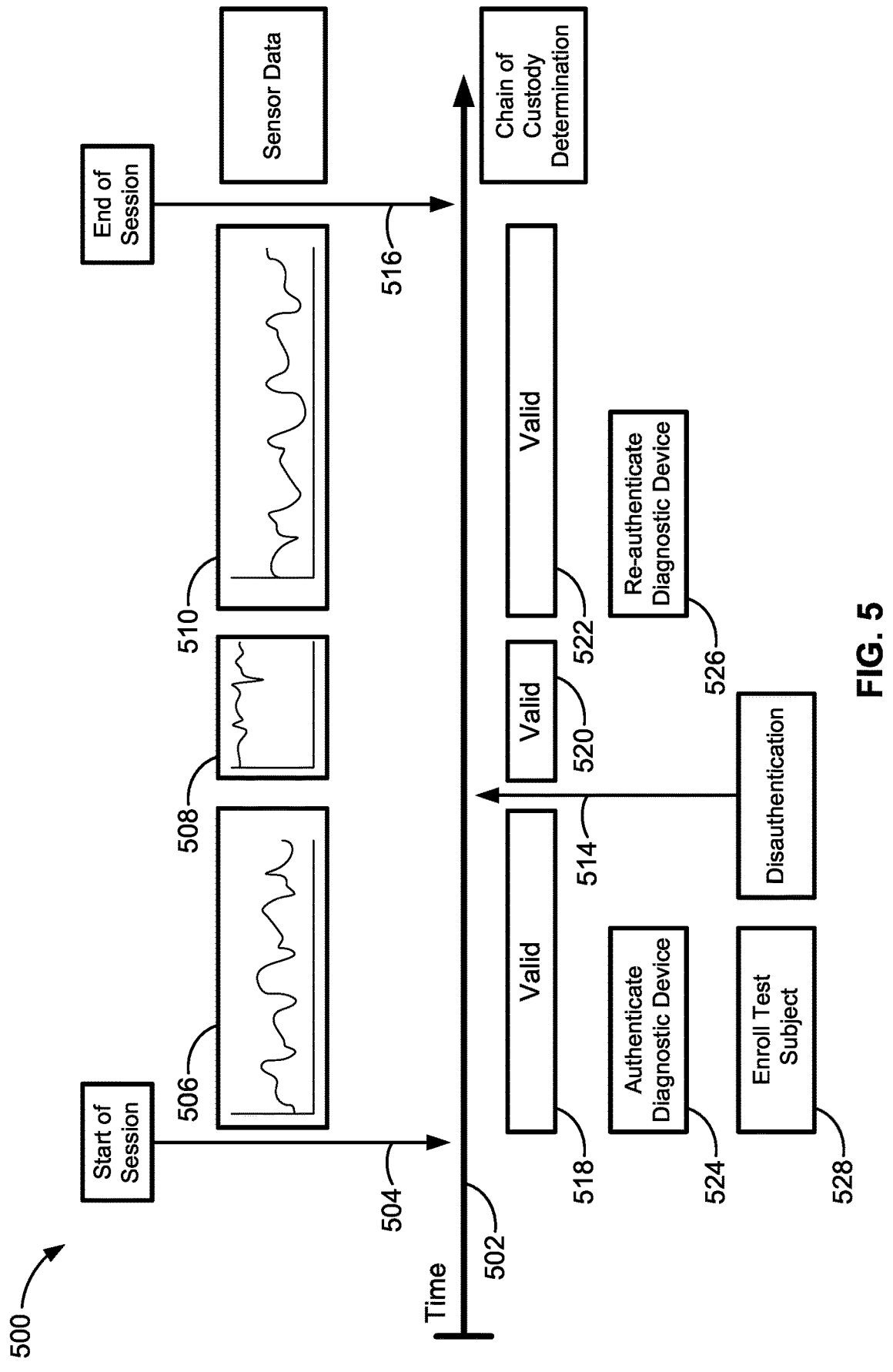
FIG. 5 is a combination chat depicting a testing session according to certain aspects of the present disclosure.

FIG. 5 is a combination chat 500 depicting a testing session according to certain aspects of the present disclosure. Chart 500 includes a timeline 502. A testing session begins at a first time 504 and continues until a second time 516.

At the first time 504, the test subject can be enrolled, as indicated by block 528 (e.g., enrolling as described with reference to block 402 of FIG. 4) and the diagnostic device can be authenticated, as indicated by block 524 (e.g., authenticating as described with reference to block 406 of FIG. 4). Once the test subject has been enrolled (e.g., the identity of the test subject has been confirmed as the identity of the intended test subject) and the diagnostic device has been authenticated (e.g., a determination is made that the diagnostic device is acquiring sensor data of the test subject), a chain of custody determination can be made to indicate the sensor data being acquired as valid, as indicated by block 518.

Chart 500 includes an indicator of sensor data collected by the diagnostic device. Sensor data is broken out into three sensor data segments (e.g., sensor data segments 506, 508, and 510) due to gaps in the received sensor data. Gaps in the received sensor data can occur for various reasons, such as if connectivity between the diagnostic device and the user device fails (e.g., and the sensor data cannot be sufficiently buffered), if the test subject inadvertently bumps or removes the diagnostic device briefly, or if the diagnostic device is removed from the test subject and placed on another individual. These sensor data segments 506, 508, 510 can be representative of raw sensor data and/or derived physiological parameter(s).

As seen in FIG. 5, the pattern of sensor data segment 506 is different from the pattern of sensor data segment 508. In some cases, system can determine that the pattern of sensor data segment 506 is associated with the intended test subject, whereas the pattern of sensor data segment 508 is likely associated with another individual, thus indicative of a disauthentication event. The disauthentication event can occur at a third time 514 between the first time 504 and the second time 516. In response to detection of the disauthentication event, the system can generate a chain of custody determination that the sensor data is invalid, as indicated by block 520. In some cases, instead of or in addition to determining that a pattern of sensor data segment 506 differs from a pattern of sensor data segment 508, a determination can be made that a physiological parameter represented by sensor data segment 506 deviates from that of sensor data segment 508 by an out-of-threshold amount (e.g., an out-of-threshold deviation, such as a deviation of more than a threshold value). In some cases, the out-of-threshold amount can be based on other physiological parameters (e.g., the amount of allowable deviation for a first physiological parameter can be based on the value(s) of one or more other physiological parameters).

In some cases, after a disauthentication event has been detected, the system can prompt the test subject to re-authenticate the diagnostic device. Re-authentication of the diagnostic device can occur similarly to or the same as initial authentication of the diagnostic device. As depicted along timeline 502, once the user re-authenticates the diagnostic device, as indicated by block 526, the system can generate a chain of custody determination that the sensor data being collected is once again valid, as indicated by block 522. Thus, while sensor data may be collected for the entire testing session, only those periods of time where the chain of custody determination is valid (e.g., blocks 518 and 522) would be used for a diagnosis. In some cases, reauthentication of the diagnostic device can include determining that the pattern of sensor data segment 510 is sufficiently similar to the pattern of sensor data segment 506.

Figure 6:
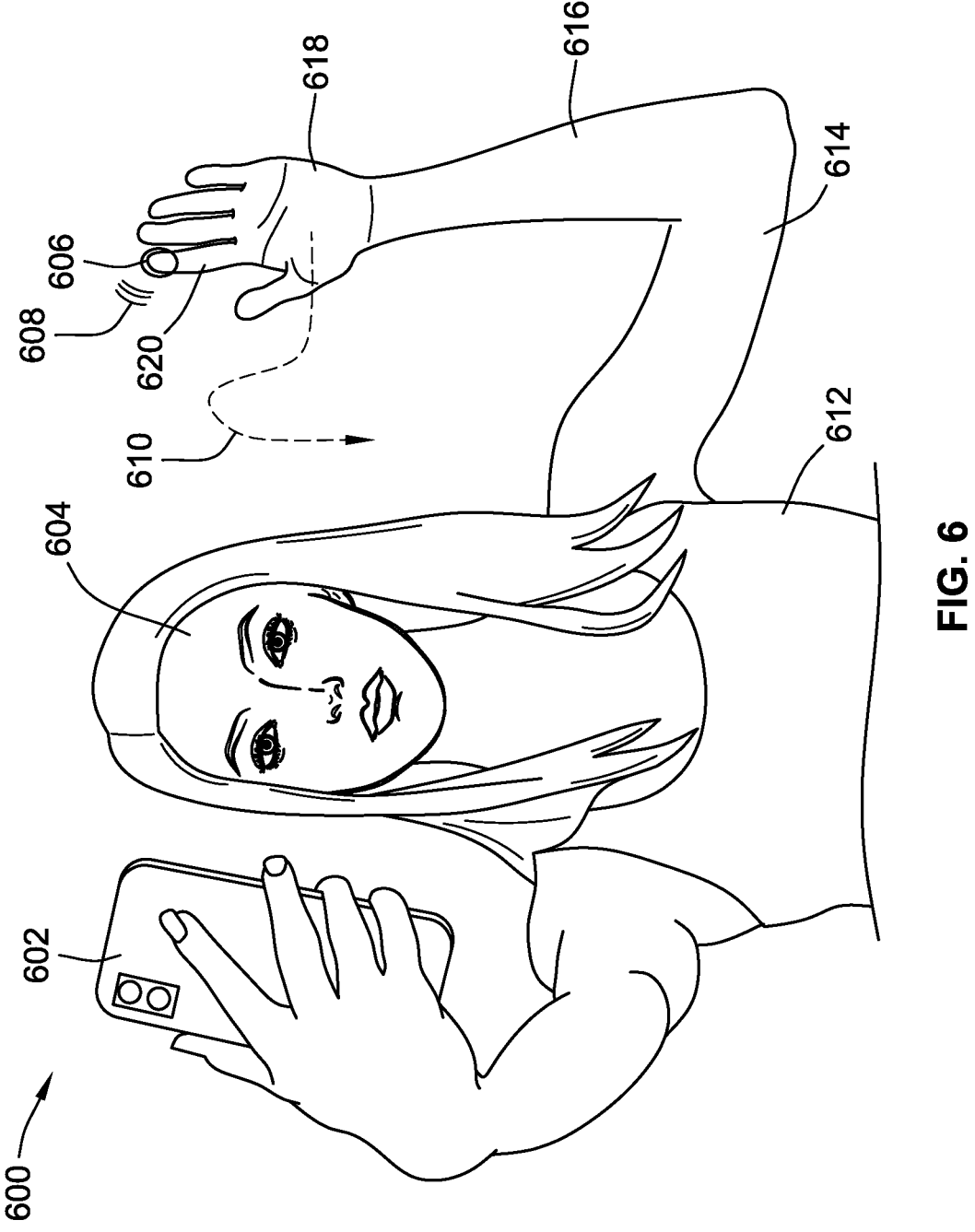
FIG. 6 is a representation of a user engaging in an enrollment and/or authentication action according to certain aspects of the present disclosure.

FIG. 6 is a representation of a user 600 engaging in an enrollment and/or authentication action according to certain aspects of the present disclosure. The user 600 can initiate and complete the enrollment and/or authentication action via a user device 602 (e.g., a smartphone). In the example of FIG. 6, enrollment can occur by capturing an image of the user's face 604 and comparing it to a known image (e.g., a previously capture image of the user's driver's license or other identification card). In some cases, enrollment can occur by capturing other recognizable features of the user, such as capturing speech of the user via a microphone to identify vocal biomarkers associated with the user.

In some cases, authentication can occur by comparing a detected movement pattern with an expected movement pattern. Movement patterns can be one-dimensional, two-dimensional, or three-dimensional. In some cases, movement patterns can include a timing component, such that the same three-dimensional movement conducted at different speeds or with different timings can be considered different movement patterns. As the user 600 moves their hand 619 in the pattern 610, the diagnostic device 606 worn by the user 600 on a finger 620 can collect sensor data (e.g., movement data) associated with movement in that pattern 610. This sensor data can be compared to an expected movement pattern. In some cases, the expected movement pattern can be a preset movement pattern that was provided to the user 600 as an instruction (e.g., an instructed movement pattern whereby the system can prompt the user 600 to move their hand 618 in the expected movement pattern). In some cases, the expected movement pattern can be a movement pattern detected by one or more sensors of a device other than the diagnostic device 606, such as by a camera of user device 602. In such an example, authenticating the diagnostic device can include determining that the pattern 610 indicated by the sensor data collected by the diagnostic device is sufficiently similar to the pattern indicated by the camera data collected by the user device 602. In some cases, the system can instruct the user 600 generally to perform a movement with their hand 618, without necessarily instructing the user 600 exactly what movement to perform. In some cases, the system can instruct the user 600 to write a word or sign their name, thus invoking a movement with their hand 618. In at least one or more of these ways, the system can determine that the diagnostic device 606 is indeed on the hand 618 of the user 600.

In some cases, authentication can include determining a matching score based on the detected movement pattern and the expected movement pattern. The matching score can indicate how closely the detected movement pattern from the diagnostic device matches the expected movement pattern. If the matching score is above a threshold value, authentication can be considered successful. In some cases, if the matching score is below a threshold value and/or within a threshold range, the system can prompt the user to continue authentication, such as by repeating the movement pattern or attempting a different movement pattern. In some cases, the expected movement pattern can be randomized (e.g., random or pseudorandom) to avoid replay attacks by video.

In some cases, authentication can further include confirming that the feature used to enroll the user 600 is bodily connected to the diagnostic device 606. As seen in FIG. 6, the feature used to enroll the user 600 is the user's face 604, which is continuously connected to the diagnostic device 606 (e.g., the diagnostic device for which the pattern was detected) via the user's torso 612, the user's upper (e.g., proximal) arm 614, the user's lower (e.g., distal) arm 616, the user's hand 618, and the user's finger 620. This confirmation can occur in any suitable technique such as by capturing in a single image frame or in a continuous set of sequential images, the user's face 604, the user's torso 612, the user's upper (e.g., proximal) arm 614, the user's lower (e.g., distal) arm 616, the user's hand 618, the user's finger 620, and the diagnostic device 606.

In some cases, authentication can include detecting an output signal 608 being transmitted by the diagnostic device 606. The output signal 608 can be any suitable signal that is discernable by another device, such as user device 602. For example, the output signal 608 may be an optical signal (e.g., an infrared pulse) detected by a camera of the user device 602 or an auditory signal (e.g., an ultrasonic sound) detected by a microphone of the user device 602. In some cases, the output signal 608 can be a random or pseudorandom signal that is output for detection by the user device 602. In some cases, the output signal 608 can be temporally based (e.g., can be a timecode or based on a current time). In some cases, the output signal 608 can be a preset code or an encoded identifier associated with the diagnostic device 606 (e.g., a unique identifier).

In some cases, detection of the output signal 608 by the user device 602 is indicative that the diagnostic device 606 is being worn by the user 600. In some cases, authentication of the diagnostic device via a movement pattern can include detecting a movement pattern associated with the output signal 608 (e.g., a pattern of movement of emitted light from the diagnostic device 606). In some cases, one or more sensors of the user device 602 is able to detect an actual movement pattern of the diagnostic device 606 by detecting movement of the output signal 608 (e.g., via camera data for an optical signal or echolocation for an auditory signal).

While described with reference to movement of a hand 618, enrollment and/or authentication can be performed with any suitable body part associated with a diagnostic device 606.

Figure 7:
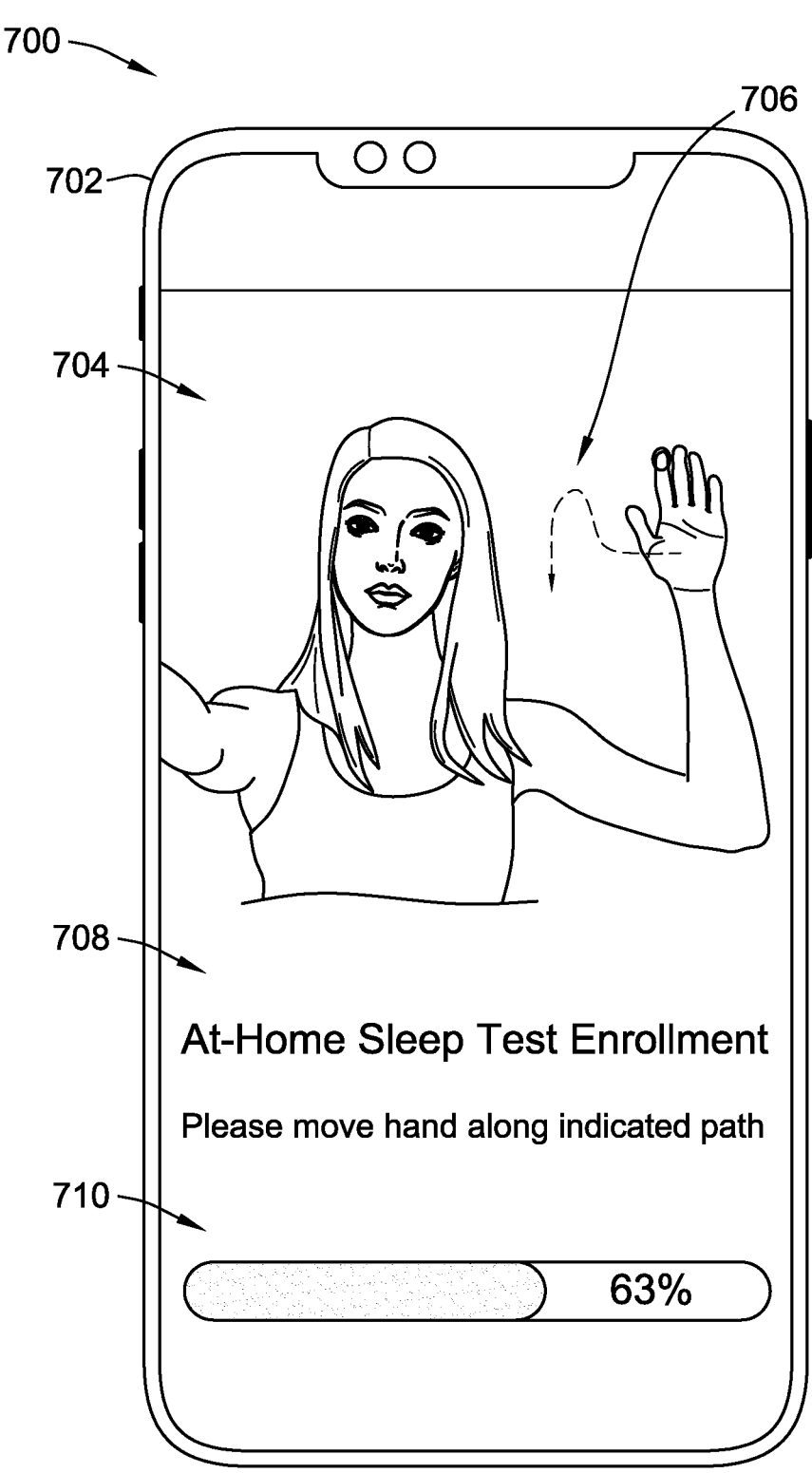
FIG. 7 is a schematic diagram depicting a graphical user interface on a user device, according to certain aspects of the present disclosure.

FIG. 7 is a schematic diagram depicting a graphical user interface 702 on a user device 700, according to certain aspects of the present disclosure. The user device 700 can be any suitable user device (e.g., user device 260 of FIG. 1). In some cases, user device 700 is user device 602 of FIG. 6 while the user is attempting authentication.

The graphical user interface (GUI) 702 can be presented on a display of the user device 700. The GUI 702 can include an image of the user 704 performing the authentication procedure, such as described with reference to FIG. 6. In some cases, the image 704 (e.g., a feedback image) of the user is a live image, although that need not always be the case. The GUI 702 can include a textual instruction 708 and/or a visual instruction 706 indicating how the user is to move their hand (or other body part). In some cases, such as when the image 704 is a live image, the visual instruction 706 can be an augmented reality overlay on the live image. This augmented reality overlay can be presented to facilitate the user moving their hand in the correct pattern. In some cases, the GUI 702 can include a progress bar 710 indicating the user's progress in completing authentication.

In some cases, the image 704 is a live image, delayed image, or still image acquired from a camera, such as from a camera of the user device 700. In some cases, however, image 704 is a simulated image of the user generated from other sensor data, such as LIDAR data from the user device 700 or movement data acquired by the diagnostic device. For example, a simulated image of the user's arm moving in a pattern can be generated based on the movement data sensed by the diagnostic device. In some cases, image 704 can include both a live image acquired by one or more sensors of the user device 700 and a simulated image generated by one or more sensors of the diagnostic device.

Figure 8:
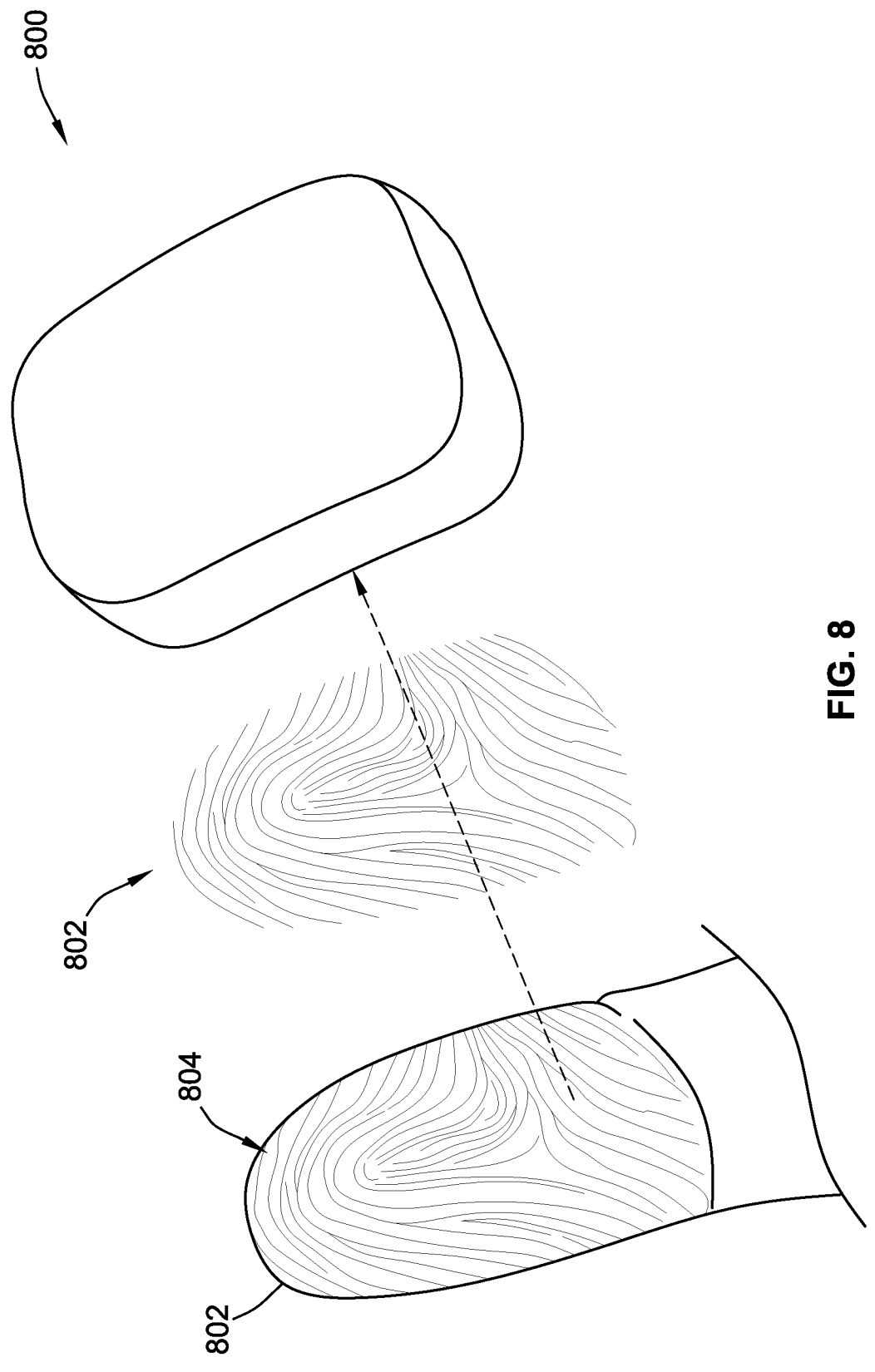
FIG. 8 is a schematic diagram of a diagnostic device for placement on a finger of a user, according to certain aspects of the present disclosure.

FIG. 8 is a schematic diagram of a diagnostic device 800 for placement on a finger 802 of a user, according to certain aspects of the present disclosure. Diagnostic device 800 can be any suitable diagnostic device, such as diagnostic device 280 of FIG. 1. In some cases, diagnostic device 800 can include a PPG sensor. Diagnostic device 800 can be designed to fit over a fingerprint 804 of a user's finger 802.

In some cases, when the diagnostic device 800 has been placed on the user's finger 802, one or more sensors of the diagnostic device 800 can detect identifiable features of the user's finger 802, such as portions of the user's fingerprint 804 or other identifiable portions of the user's finger 802. Detection of one or more identifiable features of the user's finger 802 can be used to authenticate the diagnostic device 800, as described in further detail herein. In some cases, even a vague detection of a fingerprint 804 can be sufficient to identify when the diagnostic device 800 has been removed from the user's finger 802, and possibly placed on another individual's finger.

Detection of a user's fingerprint 804 can be performed by any suitable technique, such as via ultrasonic, optical (e.g., a camera), capacitive, or other such techniques known in the art, such as those utilized in smart phones (e.g., to unlock screens, access banking apps, etc.), dedicated fingerprint scanners, and the like. Ridges can be detected and fingerprint minutiae (e.g., ridge endings, bifurcations, and the like) can be captured. The pattern of these features can be accessed, stored, and processed in a fingerprint database.

In some cases, the fingerprint 804 or other identifiable feature detected by the diagnostic device 800 can be compared with known data, such as known data previously acquired by a prior use of the diagnostic device 800, known data accessed from a database of existing identifiable feature data (e.g., a fingerprint registry), known data acquired by another device, such as a separate fingerprint reader and/or the user device (e.g., a camera of the user device capturing the fingerprint 804 during enrollment of the test subject, prior to authentication of the diagnostic device 800). In some cases, another device (e.g., a separate fingerprint reader and/or a user device) can acquire identifiable feature data (e.g., a fingerprint scan) of another finger of the user or an alternate portion of finger 802, which may nevertheless be comparable to the fingerprint 804 (or other identifiable feature) of finger 820.

In some cases, the diagnostic device 800 can collect sensor data from finger 802 while another device (e.g., a separate fingerprint reader and/or a user device, optionally coupled to or integrated with the diagnostic device) can acquire identifiable feature data (e.g., a fingerprint scan) of another finger of the user or an alternate portion of finger 802, which may be compared with known data, as described above, to determine that the diagnostic device 800 is collecting sensor data from the identified individual.

In some cases, diagnostic device 800 can detect the user's fingerprint 804 continuously, at a regular interval, at a predetermined time (e.g., at the end of a testing session), or in response to a trigger signal. Any suitable trigger signal can be used, such as a dropout in a signal or sensor data, an above-threshold value for raw sensor data or a derived physiological parameter, or the like.

In some cases, when a fingerprint 804 is used to authenticate the diagnostic device 800, enrollment of the test subject can be automatically performed by matching the detected fingerprint 804 to a known fingerprint to identify the individual associated with the fingerprint 804 (e.g., identify them as the intended test subject).

In some cases, the diagnostic device 800 can not only detect the fingerprint 804, but can also determine that the finger 802 to which it is attached is a living finger (e.g., made of live tissue). This determination can be made in any suitable way, such as via sensor data (e.g., blood oxygen saturation levels and heart rate).

FIGS. 9A-9D are schematic diagrams depicting progression of a tag 904 used in association with a diagnostic device 916, according to certain aspects of the present disclosure. Tag 904 can be any suitable tag, such as tag 106 of FIG. 1. Diagnostic device 916 can be any suitable diagnostic device, such as diagnostic device 280 of FIG. 1.

Figure 9B:
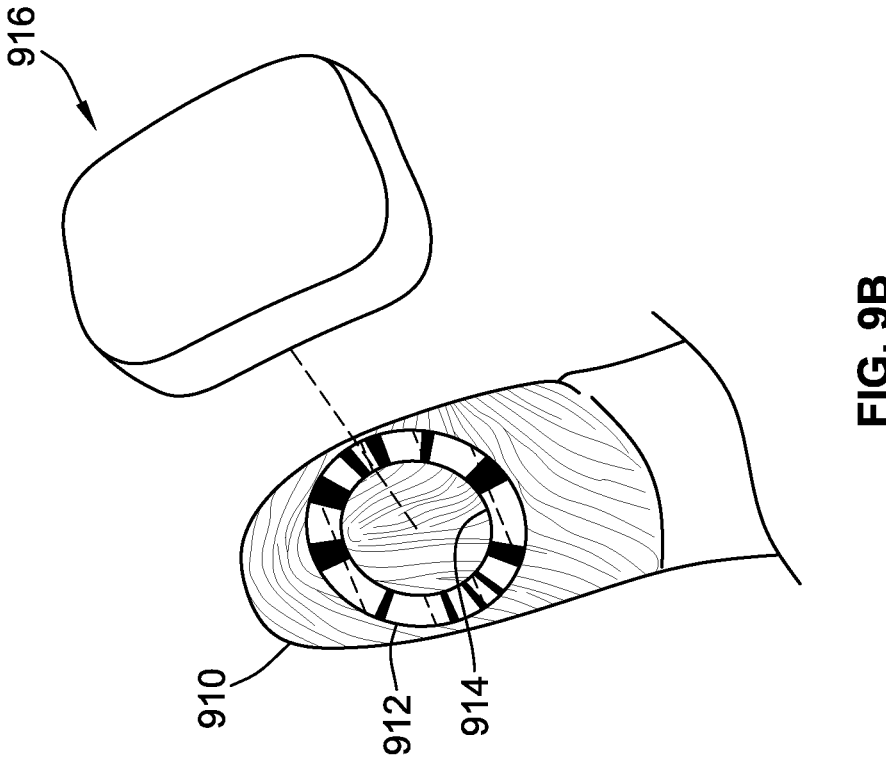
FIGS. 9A-9D are schematic diagrams depicting progression of a tag used in association with a diagnostic device, according to certain aspects of the present disclosure.
Figure 9A:
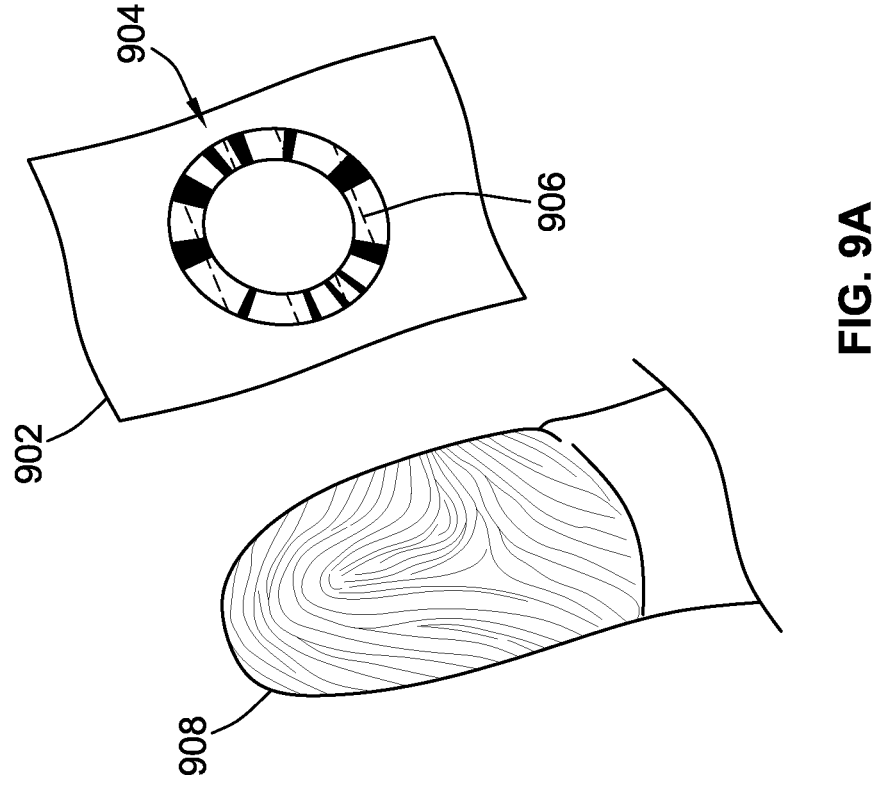
Figure 9D:
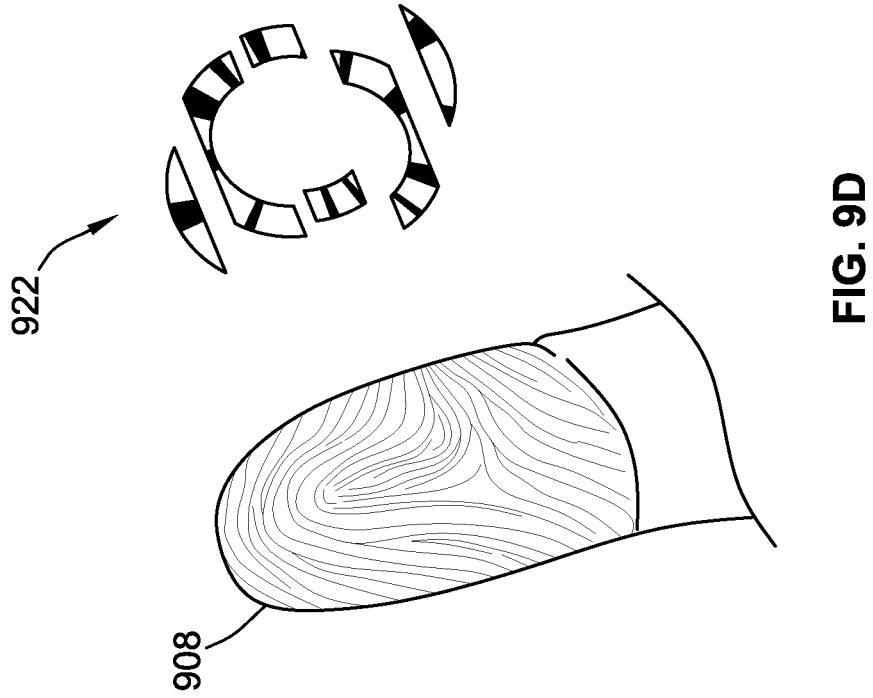
Figure 9C:
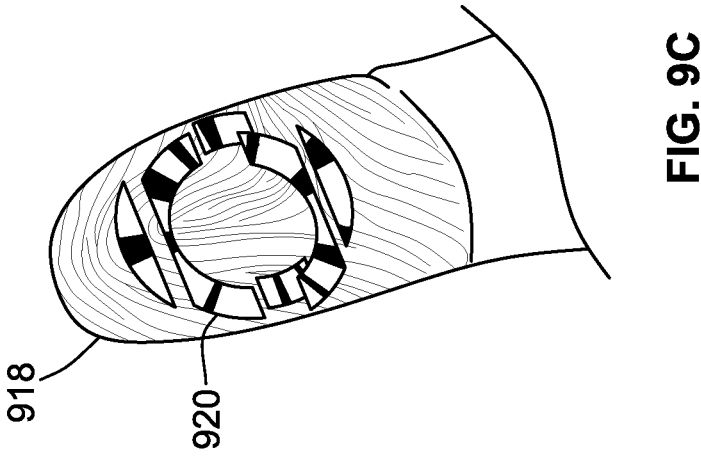

In FIG. 9A, the tag 904 is not yet placed on finger 908. In FIG. 9B, the tag 912 has been placed on the user's finger 910 and a diagnostic device 916 can be placed on top. In FIG. 9C, the tag 920 is being removed from the user's finger 918. In FIG. 9D, the tag 922 has been removed from the user's finger 908.

As depicted in FIG. 9A, tag 904 can be a small, round sticker with an inner window. The tag 904 can have other suitable shapes and sizes, and is generally formed of or comprises an adhesive material. Tag 904 can include an authentication feature in the form of a barcode (e.g., a circular barcode) printed thereon, although other authentication features can be used. In some cases, tag 904 can include failure points 906 as an anti-tamper feature. Failure points 906 can be designed to break during attempts to remove the tag 904 from skin of a user, thus destroying the authentication feature.

Tag 904 can be initially removed from a protective sheet 902. Protective sheet 902 can protect an adhesive layer of the tag 904 and can be configured to be easily removed, thus avoiding premature breaking of the failure points 906. The tag 904 can be applied to a user's finger 908. In some cases, tag 904 can be applied to a user's finger 908 by a trusted professional (e.g., a healthcare provider), although that need not always be the case. In some cases, the tag 904 can be applied to the user's finger 908 and the tag 904 can be authenticated as being attached to the intended test subject through other means, such as disclosed herein with reference to a enrolling a test subject and authenticating a diagnostic device.

As depicted in FIG. 9B, finger 910 can be finger 908 of FIG. 9A after attachment of tag 904. The tag 912 can be seen adhesively coupled to finger 910. A window 914 in the tag 912 can permit one or more sensors of the diagnostic device 916 to access the finger 910 directly, such as to obtain blood oxygen saturation data and/or cardiac data, such as heart rate data. When the diagnostic device 916 is applied to the finger 910 having a tag 912 thereon, the diagnostic device 916 can detect the authentication feature (e.g., circular barcode), such as via one or more sensors (e.g., light sensors or cameras). When the diagnostic device 916 is acquiring sensor data of the test subject via finger 910, it can be determined that the chain of custody remains unbroken as long as the diagnostic device 916 is able to detect the authentication feature of the tag 912.

As depicted in FIG. 9C, finger 918 is finger 910 of FIG. 9B during removal of tag 920. As depicted, attempts to remove tag 920 from skin of the user cause the tag 920 to break at the failure points (e.g., failure points 906). As a result, the authentication feature of the tag 920 can become sufficiently disfigured to render it unsuitable for authentication (e.g., unable to be used to authenticate and/or indicative of disauthentication).

As depicted in FIG. 9D, tag 922 is tag 920 of FIG. 9C after removal from finger 918. Tag 922 is shown broken into pieces. While six pieces are shown, any number of pieces in any shapes can be used to discourage and/or detect attempts to recreate the authentication feature. While disclosed as a sticker with a visual authentication feature, other tags can be used.

Figures 10A, 10B, 10C:
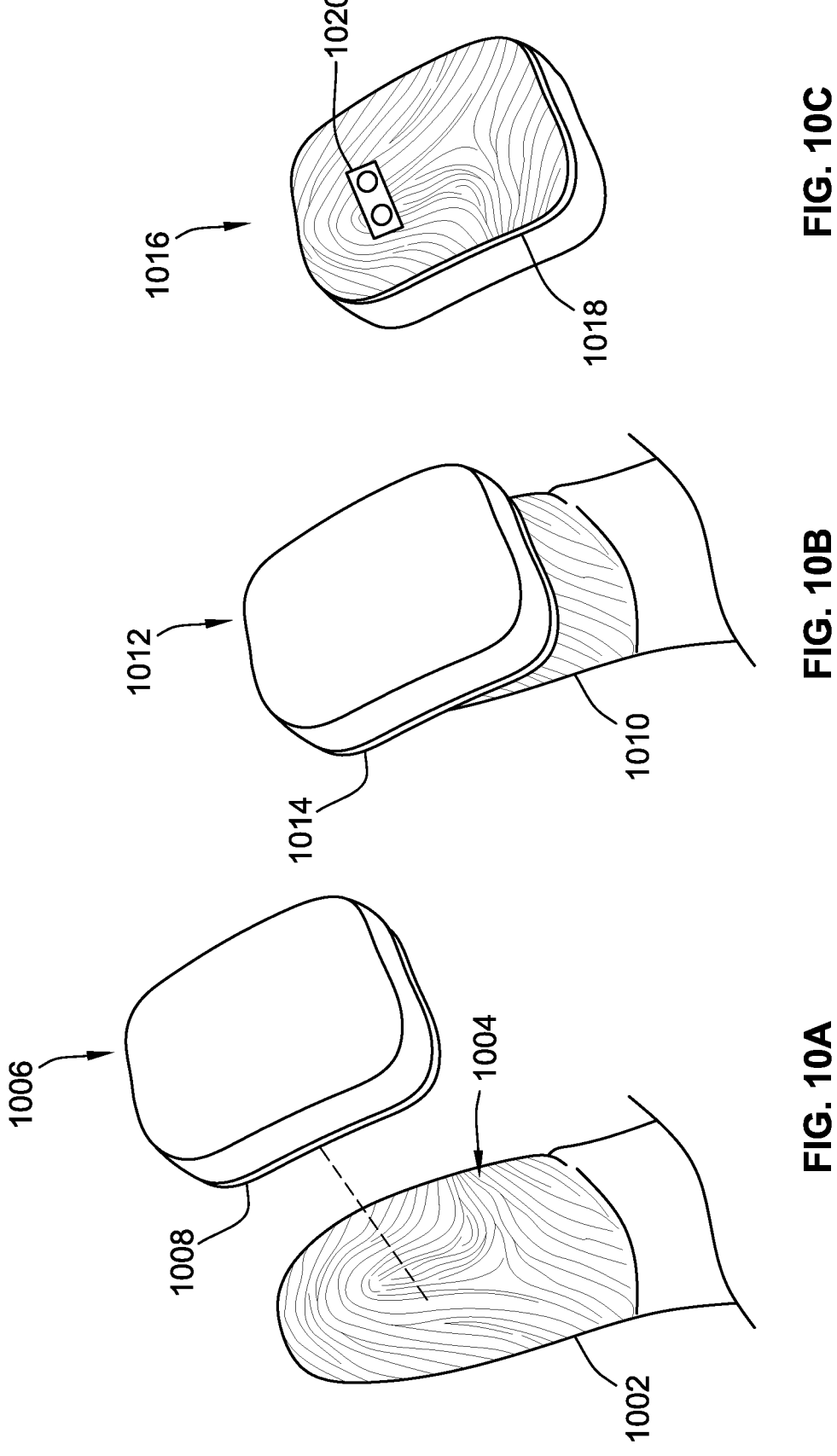
FIGS. 10A-10C are schematic diagrams depicting progression of a diagnostic device capable of acquiring fingerprints, according to certain aspects of the present disclosure.

FIGS. 10A-10C are schematic diagrams depicting progression of a diagnostic device 1006 capable of acquiring fingerprints 1004, according to certain aspects of the present disclosure. Diagnostic device 1006 can be any suitable diagnostic device, such as diagnostic device 280 of FIG. 1.

As depicted in FIG. 10A, diagnostic device 1006 can include an imprint layer 1008. In some cases, a removable protective layer can be placed over imprint layer 1008 until it is time to apply the diagnostic device 1006 to a finger 1002. Diagnostic device 1006 can be applied to a finger 1002 having a fingerprint 1004, although any other body part and/or identifiable feature can be used.

As depicted in FIG. 10B, finger 1010 is finger 1002 of FIG. 10A after diagnostic device 1006 has been placed thereon. Diagnostic device 1012 is seen placed over the fingerprint of finger 1010. The imprint layer 1014 is contacting the fingerprint. While in this configuration, the diagnostic device 1012 can collect sensor data. After the testing session is complete, the diagnostic device 1012 can be removed from finger 1010.

FIG. 10C shows a bottom view of the diagnostic device 1016, showing the side of the imprint layer 1018 that had been pressed against the finger 1010 of FIG. 10B. As depicted in FIG. 10C, after removal from a finger, diagnostic device 1016 can be imprinted with the user's fingerprint (or other identifiable feature). The user's fingerprint is seen in the imprint layer 1018. In some cases, imprint layer 1018 can include a sensor window 1020 through which one or more sensors of the diagnostic device 1016 can collect sensor data from the finger.

The fingerprint that has been imprinted on the imprint layer 1018 can be scanned or otherwise imaged to be compared with a known fingerprint of the intended test subject (e.g., a previously or subsequently acquired fingerprint of the intended test subject). If the imprinted fingerprint sufficiently matches the known fingerprint of the intended test subject, a determination can be made that the diagnostic device 1016 was indeed collecting sensor data from the intended test subject, and thus the chain of custody was unbroken for the testing session. In some cases, detection of multiple fingerprints or an incorrect fingerprint can be indicative of a disauthentication event.

The imprint layer 1018 can be any suitable material capable of retaining an imprint of the user's fingerprint. In some cases, the imprint layer 1018 is an adhesive layer. In some cases, the imprint on the imprint layer 1018 can be in the form of skin oils retained on the adhesive of the imprint later 1018, although other techniques can be used. In some cases, a protective cover (e.g., a protective film) can be provided with the diagnostic device 1016 such that a test subject can place the protective cover over the imprint layer 1018 after completion of a testing session, protecting the imprinted fingerprint from alteration before it can be verified.

While described with reference to a fingerprint of a finger, other identifiable features can be used. An imprint layer 1018 can be specifically located on the diagnostic device 1016 in a location that must be pressed against skin of the user for the diagnostic device 1016 to properly function.

Figure 11:
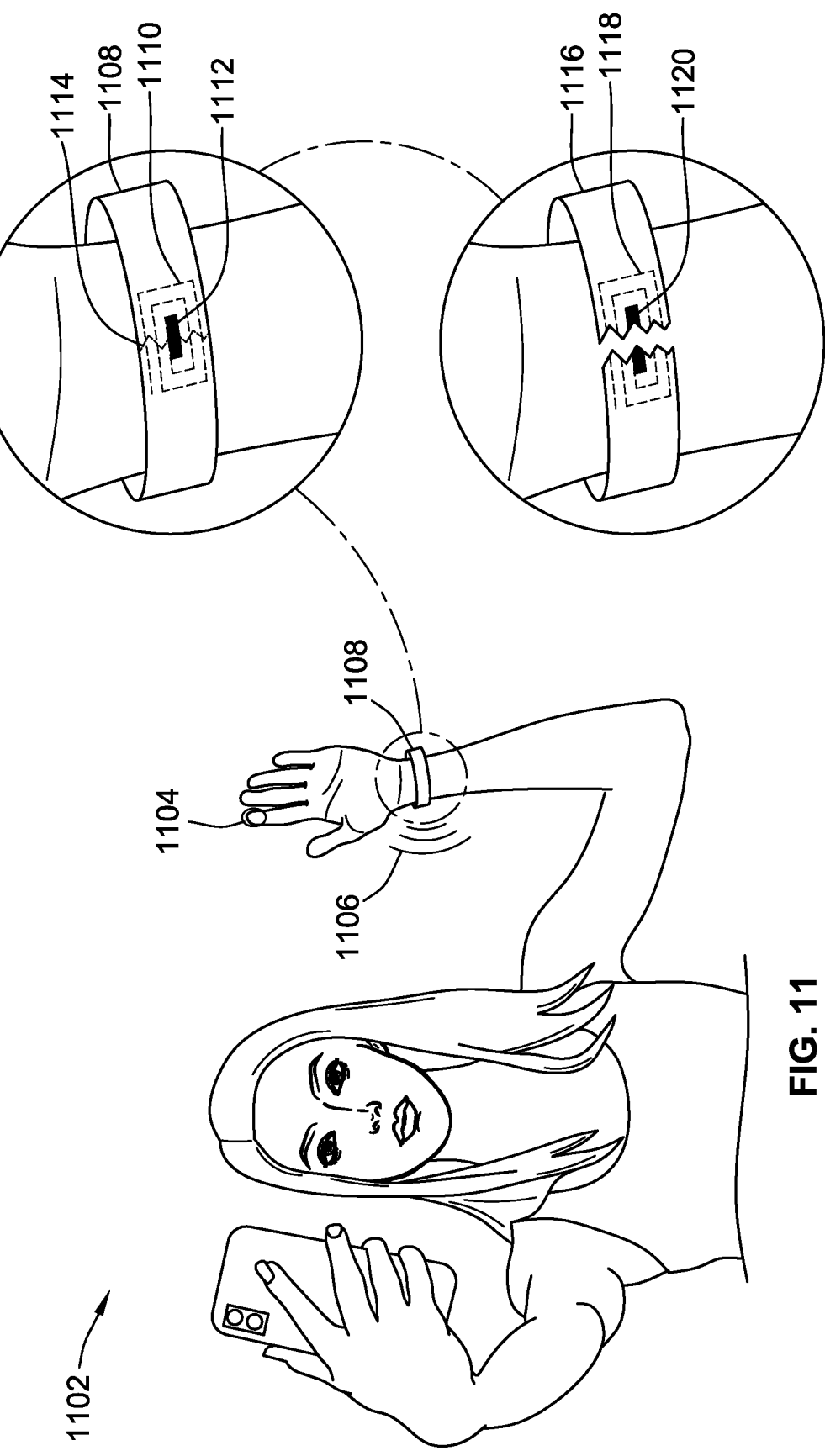
FIG. 11 is a schematic diagram depicting progression of a tag being used with a diagnostic device, according to certain aspects of the present disclosure.

FIG. 11 is a schematic diagram depicting progression of a tag 1108 being used with a diagnostic device 1104, according to certain aspects of the present disclosure. Tag 1108 can be any suitable tag, such as tag 106 of FIG. 1. Diagnostic device 1104 can be any suitable diagnostic device, such as diagnostic device 280 of FIG. 1.

Tag 1108 can be placed on the user 1102 by a trusted individual or can be otherwise enrolled and/or authenticated with the user 1102 such that a determination can be made that the tag 1108 is indeed on a wrist of the intended test subject. Tag 1108 can be secured to the user's wrist through any suitable technique, such as via adhesives (e.g., a portion of the tag's band adhering to another portion of the tag's band) or mechanical means (e.g., a one-way fastener, such as a zip-tie fastener or a non-removable button). Tag 1108 can include an authentication feature in the form of a RF transmitter. The RF transmitter can include an integrated circuit 1112 and an antenna 1110. In some cases, the RF transmitter is a passive transmitter designed to transmit an authentication signal 1106 in the presence of an interrogation signal. The interrogation signal can provide power to the integrated circuit 1112 to generate and transmit the authentication signal 1106.

In some cases, authentication can be accomplished by the diagnostic device 1104 detecting the authentication signal 1106, optionally with a signal strength above a threshold value, thus indicating that the diagnostic device 1104 is likely attached to the same individual to whom the tag 1108 is attached. In some cases, authentication can be accomplished by a separate device (e.g., a user device) detecting the authentication signal 1106 and detecting the diagnostic device 1104, optionally with signal strengths above threshold values and/or optionally with signal parameters behaving the same or similarly (e.g., being attenuated at the same rate due to movement of the user device).

Tag 1108 can include an anti-tamper feature in the form of a failure point 1114. The failure point 1114 can be designed to pass through the antenna 1110 and/or the integrated circuit 1112. The failure point 1114 can be designed to fail before other portions of the tag 1108 (e.g., before failure of a fastener used to secure the tag 1108 to the wrist of the user).

As depicted in progression in FIG. 11, tag 1116 is tag 1108 after attempted removal from the user 1102. Attempted removal resulted in failure at failure point 1114, which severed antenna 1118 and integrated circuit 1120. As a result, the RF transmitter of tag 1116 is destroyed and unable to transmit its authentication signal.

While described with reference to a tag 1108 attached around a wrist of a user, any suitable tag coupled to the user in any suitable fashion can be used. In some cases, the anti-tamper feature can include a conductor necessary for the authentication feature to function being formed throughout the loop of the tag's band such that the tag, once attached to a user 1102, can only be removed by cutting through the necessary conductor, thus rendering the authentication feature unsuitable for authentication.

Figure 12:
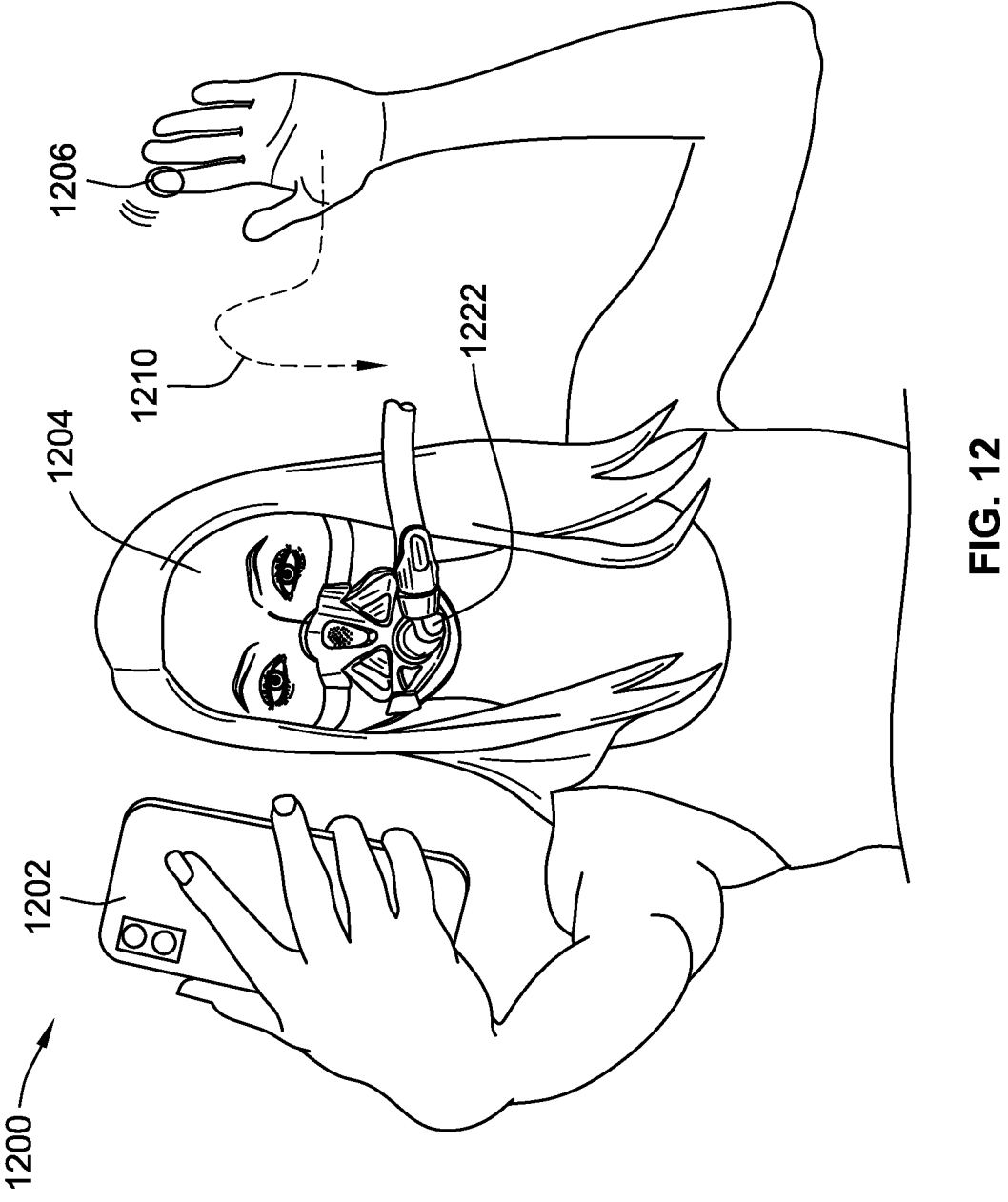
FIG. 12 is a representation of a user wearing a user interface and engaging in an enrollment and/or authentication action according to certain aspects of the present disclosure.

FIG. 12 is a representation of a user 1200 wearing a user interface 1222 and engaging in an enrollment and/or authentication action according to certain aspects of the present disclosure. User 1200 can be similar to user 600 of FIG. 6, although while wearing a user interface 1222. In some cases, while the user 1200 is engaging in an enrollment and/or authentication action as described with reference to FIG. 6, the system can also authenticate the user interface 1222 and/or its associated respiratory therapy system with the user 1200.

For example, the user device 1202 may prompt the user to engage in pattern 1210. Cameras or other sensors on user device 1202 can identify movement of the diagnostic device 1206 and can determine that the user's face 1204 is in the same frame as the diagnostic device 1206. At the same time, the system can identify that a particular user interface 1222 of a respiratory therapy device is being worn by the user 1200. In some cases, sensor data from the respiratory therapy system can be used to confirm that the respiratory therapy system communicatively coupled to the user device 1202 and/or diagnostic device 1206 is the same as that being used by the user 1200. For example, sensor data from the respiratory therapy device can be used to determine the user's respiration rate. This respiration rate can be checked against a respiration rate determined by sensors on the user device 1202 (e.g., cameras or depth sensors detecting breathing motion to derive respiration rate) and/or the diagnostic device 1206 (e.g., respiration rate derived from pulse oximetry data or the like). If the respiration rates match or are within a threshold deviation, it can be determined that the respiratory therapy device is in use by the user 1200.

One or more elements or aspects or steps, or any portion(s) thereof, from one or more of any of the claims below can be combined with one or more elements or aspects or steps, or any portion(s) thereof, from one or more of any of the other claims below or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

As used below, any reference to a series of examples is to be understood as a reference to each of those examples disjunctively (e.g., "Examples 1-4" is to be understood as "Examples 1, 2, 3, or 4").

Example 1 is a method comprising: receiving, at a user device, first sensor data from one or more sensors coupled to the user device; receiving identity enrollment information associated with a test subject engaging in a testing session; establishing a communication link between the user device and a wearable diagnostic device; associating the wearable diagnostic device with the testing session, wherein associating the wearable diagnostic device with the testing session includes determining that the wearable diagnostic device is being worn by the test subject at a first time based at least in part on the first sensor data; receiving second sensor data from the wearable diagnostic device after the first time; analyzing the second sensor data to identify an interference instance indicative that the wearable diagnostic device is no longer worn by the test subject at a second time; generating a chain of custody determination based at least in part on the interference instance; and associating the chain of custody determination with the testing session.

Example 2 is the method of example(s) 1, further comprising generating one or more test results associated with the testing session based at least in part on the received second sensor data used to identify the interference instance.

Example 3 is the method of example(s) 1 or example 2, wherein receiving identity enrollment information includes i) receiving identification card image data; ii) receiving facial image data of the test subject; iii) receiving image data of an identifiable physical feature of the test subject; iv) receiving a machine readable identification script; v) receiving image data of a barcode; v) receiving identification information from a radiofrequency tag; vi) receiving a biometric passport parameter; vii) receiving electronic identification information from an identification chip; or viii) any combination of i-vii.

Example 4 is the method of any one of example(s)s 1 to 3, wherein associating the wearable diagnostic device with the testing session includes: analyzing the second sensor data to detect a movement pattern of the wearable diagnostic device; comparing the detected movement pattern with an expected movement pattern; and confirming that the wearable diagnostic device is being worn by the test subject based on the comparison of the detected movement pattern with the expected movement pattern.

Example 5 is the method of example(s) 4, further comprising storing, in association with the testing session, a portion of the second sensor data used to detect the movement pattern of the wearable diagnostic device.

Example 6 is the method of example(s) 4 or example 5, associating the wearable diagnostic device with the testing session further includes analyzing the first sensor data to identify an expected movement pattern for the wearable device.

Example 7 is the method of any one of example(s)s 4 to 6, associating the wearable diagnostic device with the testing session further includes presenting an instruction for the test subject to engage in an instructed movement pattern.

Example 8 is the method of example(s) 7, wherein presenting the instruction for the test subject to engage in the instructed movement pattern includes: generating a feedback image indicative of the test subject engaging in the instructed movement pattern, wherein generating the feedback image is based at least in part on i) the first sensor data, ii) the second sensor data, or iii) a combination of the first sensor data and the second sensor data; and presenting the feedback image in association with the presented instruction.

Example 9 is the method of example(s) 8, wherein the feedback image is a live image of the test subject engaging in the instructed movement pattern, and wherein the presented instruction is overlaid on the live image.

Example 10 is the method of any one of example(s)s 1 to 9, wherein the first sensor data includes image data.

Example 11 is the method of any one of example(s)s 1 to 10, wherein associating the wearable diagnostic device with the testing session further includes i) receiving a unique identifier associated with the wearable diagnostic device over the communication link; ii) detecting a unique identifier associated with the wearable diagnostic device based at least in part on the first sensor data; iii) receiving user input indicative of a unique identifier associated with the wearable diagnostic device; or iv) any combination of i-iii.

Example 12 is the method of any one of example(s)s 1 to 11, wherein associating the wearable diagnostic device with the testing session further includes: presenting an instruction to perform an action with the wearable diagnostic device, wherein the wearable device transmits a signal in response to performance of the action; receiving the signal from the wearable device via the communication link; detecting performance of the instructed action in response to receiving the signal.

Example 13 is the method of example(s) 12, wherein the action includes pressing a button on the wearable device.

Example 14 is the method of any one of example(s)s 1 to 13, wherein associating the wearable diagnostic device with the testing session further includes determining an approximate distance to the wearable diagnostic device based at least in part on i) the first sensor data; ii) the second sensor data; iii) additional sensor data from a distance sensor; iv) a parameter of the communication link; or v) any combination of i-iv.

Example 15 is the method of any one of example(s)s 1 to 14, wherein analyzing the second sensor data to identify the interference instance further includes: determining an approximate distance to the wearable diagnostic device; determining an approximate distance to the test subject based at least in part on the first sensor data; and determining that the approximate distance to the wearable diagnostic device and the approximate distance to the test subject differ by a threshold amount; and identifying the interference instance in response to determining that the approximate distance to the wearable diagnostic device and the approximate distance to the test subject differ by the threshold amount.

Example 16 is the method of any one of example(s)s 1 to 15, wherein analyzing the second sensor data to identify the interference instance includes identifying a dropout in the second sensor data at the second time.

Example 17 is the method of example(s) 16, wherein analyzing the second sensor data to identify the interference instance further includes identifying no dropout in the communication link at the second time.

Example 18 is the method of example(s) 16 or 17, wherein analyzing the second sensor data to identify the interference instance further includes: determining one or more pre-dropout physiological parameters based at least in part on the second sensor data between the first time and the second time; continuing, at a third time, to receive the second sensor data after the second time; determining one or more post-dropout physiological parameters based at least in part on the second sensor data after the third time; and comparing the one or more pre-dropout physiological parameters with the one or more post-dropout physiological parameters to determine that the identified dropout is indicative that the wearable diagnostic device is no longer worn by the test subject.

Example 19 is the method of any one of example(s)s 1 to 18, wherein analyzing the second sensor data to identify the interference instance includes: determining one or more physiological parameters based at least in part on the second sensor data; identifying an out-of-threshold change in the one or more physiological parameters.

Example 20 is the method of example(s) 19, further comprising: accessing one or more historical physiological parameters of the test subject; analyzing the one or more historical physiological parameters of the test subject to establish a threshold value for the out-of-threshold change.

Example 21 is the method of any one of example(s)s 1 to 20, wherein analyzing the second sensor data to identify the interference instance includes: determining one or more physiological parameters based at least in part on the second sensor data; applying the one or more physiological parameters to a trained machine learning algorithm to identify the interference instance, wherein the trained machine learning algorithm is trained based at least in part on one or more historical physiological parameters of the test subject.

Example 22 is the method of example(s) 21, wherein the one or more physiological parameters includes i) blood oxygen saturation; ii) heart rate; iii) heart rate variability; iv) a temperature of the test subject; v) a skin tone of the test subject; vi) a peripheral arterial tone; vii) a blood oxygen saturation curve shape; viii) blood pressure; ix) electroencephalogram data; x) electrooculography data; xi) electromyography data; xii) micromovement data; xiii) respiration rate; xiv) a breathing curve; or xv) any combination of i-xiv.

Example 23 is the method of any one of example(s)s 1 to 22, wherein the chain of custody determination is indicative that the received second sensor data acquired between the first time and the second time is valid.

Example 24 is the method of any one of example(s)s 1 to 23, further comprising re-associating, after the second time, the wearable diagnostic device by determining that the wearable diagnostic device is being worn by the test subject at a third time after the second time, wherein generating the chain of custody determination is indicative that i) the second sensor data between the first time and the second time is valid; and ii) that the second sensor data between the third time and a subsequent time is valid.

Example 25 is the method of example(s) 24, further comprising presenting, in response to identifying the interference instance, an instruction to re-associate the wearable diagnostic device.

Example 26 is the method of any one of example(s)s 1 to 25, wherein receiving identity enrollment information further includes: accessing a database of enrollment information; and authenticating the test subject based at least in part on the identity enrollment information and the database of enrolment information.

Example 27 is the method of any one of example(s)s 1 to 26, further comprising transmitting the first sensor data and the identity enrollment information to a remote computing device, wherein determining that the wearable diagnostic device is being worn by the test subject at the first time includes receiving, in response to transmitting the first sensor data and the identity enrollment information, a confirmation from the remote computing device that the wearable diagnostic device is being worn by the test subject.

Example 28 is the method of any one of example(s)s 1 to 27, wherein the wearable diagnostic device is a home sleep test device.

Example 29 is the method of any one of example(s)s 1 to 28, wherein the wearable diagnostic device is wearable on a body extremity of the test subject.

Example 30 is the method of any one of example(s)s 1 to 29, wherein the wearable diagnostic device includes a photoplethysmography sensor, and wherein the second sensor data includes photoplethysmography data.

Example 31 is the method of any one of example(s)s 1 to 30, further comprising receiving third sensor data from an additional wearable diagnostic device, wherein analyzing the second sensor data to identify the interference instance includes comparing the second sensor data with the third sensor data.

Example 32 is the method of any one of example(s)s 1 to 31, wherein determining that the wearable diagnostic device is being worn by the test subject includes: determining one or more physiological parameters from the first sensor data; determining one or more physiological parameters from the second sensor data; comparing the one or more physiological parameters from the first sensor data with the one or more physiological parameters from the second sensor data.

Example 33 is the method of example(s) 32, wherein the first sensor data includes image data, wherein the one or more physiological parameters from the first sensor data is derived from the image data, and wherein the one or more physiological parameters from the first sensor data and the one or more physiological parameters from the second sensor data are representative of i) a heart rate; ii) a breathing shape; iii) a respiration rate; iv) a movement pattern; v) or any combination of i-iv.

Example 34 is the method of any one of example(s)s 1 to 33, further comprising: determining one or more physiological parameters from the second sensor data; and storing the one or more physiological parameters in association with the testing session.

Example 35 is the method of example(s) 34, wherein analyzing the second sensor data to identify the interference instance includes identifying a confidence value, wherein the confidence value is indicative of a level of confidence that the wearable diagnostic device is no longer worn by the test subject, and wherein the chain of custody determination i) is indicative that the second sensor data between the first time and the second time is valid; and ii) includes the confidence interval in association with the second sensor data between the second time and a subsequent time.

Example 36 is the method of example(s) 1 to 35, further comprising: establishing a communication link between a respiratory therapy system and at least one of the user device and the wearable diagnostic device; associating the respiratory therapy device with the testing session, wherein associating the respiratory therapy device with the testing session includes determining that the respiratory therapy device is being used by the test subject based at least in part on the first sensor data; and identifying a respiratory therapy interference instance indicative that the respiratory therapy device is no longer used by the test subject, wherein generating the chain of custody determination is further based at least in part on the respiratory therapy interference instance.

Example 37 is a system comprising: a control system comprising one or more processors; and a memory having stored thereon machine readable instructions; wherein the control system is coupled to the memory, and the method of any one of example(s)s 1 to 36 is implemented when the machine executable instructions in the memory are executed by at least one of the one or more processors of the control system.

Example 38 is a system for monitoring a diagnostic chain of custody, the system comprising a control system configured to implement the method of any one of example(s)s 1 to 36

Example 39 is a computer program product comprising instructions which, when executed by a computer, cause the computer to carry out the method of any one of example(s)s 1 to 36

Example 40 is the computer program product of example (s) 39, wherein the computer program product is a non-transitory computer readable medium.

Example 41 is a system comprising: a user device having one or more sensors, one or more processors, and a memory having stored thereon machine readable instructions which, when executed by the one or more processors cause the user device to perform operations including: receiving, at the user device, first sensor data from the one or more sensors; receiving identity enrollment information associated with a test subject engaging in a testing session; establishing a communication link between the user device and a wearable diagnostic device; associating the wearable diagnostic device with the testing session, wherein associating the wearable diagnostic device with the testing session includes determining that the wearable diagnostic device is being worn by the test subject at a first time based at least in part on the first sensor data; receiving second sensor data from the wearable diagnostic device after the first time; analyzing the second sensor data to identify an interference instance indicative that the wearable diagnostic device is no longer worn by the test subject at a second time; generating a chain of custody determination based at least in part on the interference instance; and associating the chain of custody determination with the testing session.

Example 42 is the system of example(s) 41, wherein the operations further comprise generating one or more test results associated with the testing session based at least in part on the received second sensor data used to identify the interference instance.

Example 43 is the system of example(s) 41 or example 42, wherein receiving identity enrollment information includes i) receiving identification card image data; ii) receiving facial image data of the test subject; iii) receiving image data of an identifiable physical feature of the test subject; iv) receiving a machine readable identification script; v) receiving image data of a barcode; v) receiving identification information from a radiofrequency tag; vi) receiving a biometric passport parameter; vii) receiving electronic identification information from an identification chip; or viii) any combination of i-vii.

Example 44 is the system of any one of example(s)s 41 to 43, wherein associating the wearable diagnostic device with the testing session includes: analyzing the second sensor data to detect a movement pattern of the wearable diagnostic device; comparing the detected movement pattern with an expected movement pattern; and confirming that the wearable diagnostic device is being worn by the test subject based on the comparison of the detected movement pattern with the expected movement pattern.

Example 45 is the system of example(s) 44, wherein the operations further comprise storing, in association with the testing session, a portion of the second sensor data used to detect the movement pattern of the wearable diagnostic device.

Example 46 is the system of example(s) 44 or example 45, associating the wearable diagnostic device with the testing session further includes analyzing the first sensor data to identify an expected movement pattern for the wearable device.

Example 47 is the system of any one of example(s)s 44 to 46, associating the wearable diagnostic device with the testing session further includes presenting an instruction for the test subject to engage in an instructed movement pattern.

Example 48 is the system of example(s) 47, wherein presenting the instruction for the test subject to engage in the instructed movement pattern includes: generating a feedback image indicative of the test subject engaging in the instructed movement pattern, wherein generating the feedback image is based at least in part on i) the first sensor data, ii) the second sensor data, or iii) a combination of the first sensor data and the second sensor data; and presenting the feedback image in association with the presented instruction.

Example 49 is the system of example(s) 48, wherein the feedback image is a live image of the test subject engaging in the instructed movement pattern, and wherein the presented instruction is overlaid on the live image.

Example 50 is the system of any one of example(s)s 41 to 49, wherein the first sensor data includes image data.

Example 51 is the system of any one of example(s)s 41 to 50, wherein associating the wearable diagnostic device with the testing session further includes i) receiving a unique identifier associated with the wearable diagnostic device over the communication link; ii) detecting a unique identifier associated with the wearable diagnostic device based at least in part on the first sensor data; iii) receiving user input indicative of a unique identifier associated with the wearable diagnostic device; or iv) any combination of i-iii.

Example 52 is the system of any one of example(s)s 41 to 51, wherein associating the wearable diagnostic device with the testing session further includes: presenting an instruction to perform an action with the wearable diagnostic device, wherein the wearable device transmits a signal in response to performance of the action; receiving the signal from the wearable device via the communication link; detecting performance of the instructed action in response to receiving the signal.

Example 53 is the system of example(s) 52, wherein the action includes pressing a button on the wearable device.

Example 54 is the system of any one of example(s)s 41 to 53, wherein associating the wearable diagnostic device with the testing session further includes determining an approximate distance to the wearable diagnostic device based at least in part on i) the first sensor data; ii) the second sensor data; iii) additional sensor data from a distance sensor; iv) a parameter of the communication link; or v) any combination of i-iv.

Example 55 is the system of any one of example(s)s 41 to 54, wherein analyzing the second sensor data to identify the interference instance further includes: determining an approximate distance to the wearable diagnostic device; determining an approximate distance to the test subject based at least in part on the first sensor data; and determining that the approximate distance to the wearable diagnostic device and the approximate distance to the test subject differ by a threshold amount; and identifying the interference instance in response to determining that the approximate distance to the wearable diagnostic device and the approximate distance to the test subject differ by the threshold amount.

Example 56 is the system of any one of example(s)s 41 to 55, wherein analyzing the second sensor data to identify the interference instance includes identifying a dropout in the second sensor data at the second time.

Example 57 is the system of example(s) 56, wherein analyzing the second sensor data to identify the interference instance further includes identifying no dropout in the communication link at the second time.

Example 58 is the system of example(s) 56 or 57, wherein analyzing the second sensor data to identify the interference instance further includes: determining one or more pre-dropout physiological parameters based at least in part on the second sensor data between the first time and the second time; continuing, at a third time, to receive the second sensor data after the second time; determining one or more post-dropout physiological parameters based at least in part on the second sensor data after the third time; and comparing the one or more pre-dropout physiological parameters with the one or more post-dropout physiological parameters to determine that the identified dropout is indicative that the wearable diagnostic device is no longer worn by the test subject.

Example 59 is the system of any one of example(s)s 41 to 58, wherein analyzing the second sensor data to identify the interference instance includes: determining one or more physiological parameters based at least in part on the second sensor data; identifying an out-of-threshold change in the one or more physiological parameters.

Example 60 is the system of example(s) 59, wherein the operations further comprise: accessing one or more historical physiological parameters of the test subject; analyzing the one or more historical physiological parameters of the test subject to establish a threshold value for the out-of-threshold change.

Example 61 is the system of any one of example(s)s 41 to 60, wherein analyzing the second sensor data to identify the interference instance includes: determining one or more physiological parameters based at least in part on the second sensor data; applying the one or more physiological parameters to a trained machine learning algorithm to identify the interference instance, wherein the trained machine learning algorithm is trained based at least in part on one or more historical physiological parameters of the test subject.

Example 62 is the system of example(s) 61, wherein the one or more physiological parameters includes i) blood oxygen saturation; ii) heart rate; iii) heart rate variability; iv) a temperature of the test subject; v) a skin tone of the test subject; vi) a peripheral arterial tone; vii) a blood oxygen saturation curve shape; viii) blood pressure; ix) electroencephalogram data; x) electrooculography data; xi) electromyography data; xii) micromovement data; xiii) respiration rate; xiv) a breathing curve; or xv) any combination of i-xiv.

Example 63 is the system of any one of example(s)s 41 to 62, wherein the chain of custody determination is indicative that the received second sensor data acquired between the first time and the second time is valid.

Example 64 is the system of any one of example(s)s 41 to 63, wherein the operations further comprise re-associating, after the second time, the wearable diagnostic device by determining that the wearable diagnostic device is being worn by the test subject at a third time after the second time, wherein generating the chain of custody determination is indicative that i) the second sensor data between the first time and the second time is valid; and ii) that the second sensor data between the third time and a subsequent time is valid.

Example 65 is the system of example(s) 64, wherein the operations further comprise presenting, in response to identifying the interference instance, an instruction to re-associate the wearable diagnostic device.

Example 66 is the system of any one of example(s)s 41 to 65, wherein receiving identity enrollment information further includes: accessing a database of enrollment information; and authenticating the test subject based at least in part on the identity enrollment information and the database of enrolment information.

Example 67 is the system of any one of example(s)s 41 to 66, wherein the operations further comprise transmitting the first sensor data and the identity enrollment information to a remote computing device, wherein determining that the wearable diagnostic device is being worn by the test subject at the first time includes receiving, in response to transmitting the first sensor data and the identity enrollment information, a confirmation from the remote computing device that the wearable diagnostic device is being worn by the test subject.

Example 68 is the system of any one of example(s)s 41 to 67, wherein the wearable diagnostic device is a home sleep test device.

Example 69 is the system of any one of example(s)s 41 to 68, wherein the wearable diagnostic device is wearable on a body extremity of the test subject.

Example 70 is the system of any one of example(s)s 41 to 69, wherein the wearable diagnostic device includes a photoplethysmography sensor, and wherein the second sensor data includes photoplethysmography data.

Example 71 is the system of any one of example(s)s 41 to 70, wherein the operations further comprise receiving third sensor data from an additional wearable diagnostic device, wherein analyzing the second sensor data to identify the interference instance includes comparing the second sensor data with the third sensor data.

Example 72 is the system of any one of example(s)s 41 to 71, wherein determining that the wearable diagnostic device is being worn by the test subject includes: determining one or more physiological parameters from the first sensor data; determining one or more physiological parameters from the second sensor data; comparing the one or more physiological parameters from the first sensor data with the one or more physiological parameters from the second sensor data.

Example 73 is the system of example(s) 72, wherein the first sensor data includes image data, wherein the one or more physiological parameters from the first sensor data is derived from the image data, and wherein the one or more physiological parameters from the first sensor data and the one or more physiological parameters from the second sensor data are representative of i) a heart rate; ii) a breathing shape; iii) a respiration rate; iv) a movement pattern; v) or any combination of i-iv.

Example 74 is the system of any one of example(s)s 41 to 73, wherein the operations further comprise: determining one or more physiological parameters from the second sensor data; and storing the one or more physiological parameters in association with the testing session.

Example 75 is the system of example(s) 74, wherein analyzing the second sensor data to identify the interference instance includes identifying a confidence value, wherein the confidence value is indicative of a level of confidence that the wearable diagnostic device is no longer worn by the test subject, and wherein the chain of custody determination i) is indicative that the second sensor data between the first time and the second time is valid; and ii) includes the confidence interval in association with the second sensor data between the second time and a subsequent time.

Example 76 is the system of example(s) 41 to 75, wherein the operations further include: establishing a communication link between a respiratory therapy system and at least one of the user device and the wearable diagnostic device; associating the respiratory therapy device with the testing session, wherein associating the respiratory therapy device with the testing session includes determining that the respiratory therapy device is being used by the test subject based at least in part on the first sensor data; and identifying a respiratory therapy interference instance indicative that the respiratory therapy device is no longer used by the test subject, wherein generating the chain of custody determination is further based at least in part on the respiratory therapy interference instance.

Example 77 is a method comprising: receiving sensor data from a digit-wearable device worn on one or more digits of a test subject; determining one or more physiological parameters from at least a first portion of the sensor data acquired during a test session; associating the determined one or more physiological parameters with the testing session; authenticating the digit-wearable device, wherein authenticating the digit-wearable device includes: determining identification data based at least in part on at least a second portion of the sensor data, wherein the identification data includes one or more identifiable characteristics of the one or more digits; accessing authentication data, wherein the authentication data includes one or more authentication characteristics; comparing the identification data with the authentication data to determine a match, wherein the digit-wearable device is authenticated when a match is determined; generating a chain of custody determination based at least in part on the authentication of the digit-wearable device; and associating the chain of custody determination with the testing session.

Example 78 is the method of example(s) 77, wherein the one or more identifiable characteristics includes at least a portion of a digitprint.

Example 79 is the method of example(s) 77 or example 78, wherein the first portion of the sensor data includes the second portion of the sensor data.

Example 80 is the method of any one of example(s)s 77 to 79, wherein the digit-wearable device includes a first sensor positioned over a first digit and a second sensor positioned over a second digit, wherein the first portion of the sensor data is acquired by the first sensor, and wherein the second portion of the sensor data is acquired by the second sensor.

Example 81 is the method of any one of example(s)s 77 to 79, wherein the first portion of the sensor data is acquired by a first sensor and the second portion of the sensor data is acquired by the first sensor.

Example 82 is the method of any one of example(s)s 77 to 81, wherein accessing the authentication data includes accessing a database of authentication characteristics associated with a plurality of individuals.

Example 83 is the method of any one of example(s)s 77 to 81, further comprising: initially authenticating the digit-wearable device, wherein initially authenticating the digit-wearable device occurs before authenticating the digit-wearable device, and wherein initially authenticating the digit-wearable device includes: determining initial identification data based at least in part on at least a third portion of the sensor data, wherein the initial identification data includes the one or more identifiable characteristics of the one or more digits; and storing the initial identification data as the authentication data such that authenticating the digit-wearable device includes comparing the identification data with the initial identification data; wherein the chain of custody determination is indicative of a validity of the determined one or more physiological parameters associated with a time period between initially authenticating the digit-wearable device and authenticating the digit-wearable device.

Example 84 is the method of any one of examples 77 to 81, further comprising: receiving additional sensor data from a user device, wherein the additional sensor data is acquired of the one or more digits of the test subject; determining initial identification data based at least in part on the additional sensor data, wherein the initial identification data includes the one or more identifiable characteristics of the one or more digits; and storing the initial identification data as the authentication data such that authenticating the digit-wearable device includes comparing the identification data with the initial identification data.

Example 85 is the method of any one of example(s)s 77 to 84, where the first portion of the sensor data is acquired by i) an ultrasonic sensor; ii) an optical sensor; iii) a capacitive sensor; iv) a thermal sensor; v) a radiofrequency sensor; vi) a sonar sensor; vii) a tactile sensor; or viii) any combination of i-vii.

Example 86 is the method of any one of example(s)s 77 to 85, wherein the determined identification data includes a change over time of the one or more identifiable characteristics.

87 The method of any one of example(s)s 77 to 86, further comprising: re-authenticating the digit-wearable device after authenticating the digit-wearable device; and updating the chain of custody determination based at least in part on the re-authentication of the digit-wearable device.

Example 88 is the method of example(s) 87, wherein re-authentication of the digit-wearable device and updating of the chain of custody determination occur periodically based on a preset schedule.

Example 89 is the method of example(s) 87 or example 88, further comprising identifying an out-of-threshold deviation in the one or more physiological parameters, wherein re-authentication of the digit-wearable device and updating of the chain of custody determination occur in response to identifying the out-of-threshold deviation in the one or more physiological parameters.

Example 90 is the method of any one of example(s)s 87 to 89, further comprising identifying a dropout in the received sensor data, wherein re-authentication of the digit-wearable device and updating of the chain of custody determination occur in response to identifying the dropout in the received sensor data.

Example 91 is the method of any one of example(s)s 87 to 90, wherein the sensor data includes accelerometer data, the method further comprising detecting an acceleration over a threshold value based at least in part on the accelerometer data, wherein re-authentication of the digit-wearable device and updating of the chain of custody determination occur in response to detecting the acceleration over the threshold value.

Example 92 is the method of any one of example(s)s 87 to 91, further comprising generating an inference that the digit-wearable device has been removed based at least in part on the received sensor data, wherein re-authentication of the digit-wearable device and updating of the chain of custody determination occur in response to generating the inference.

Example 93 is the method of any one of example(s)s 87 to 92, wherein re-authenticating the digit-wearable device includes determining that the digit-wearable device is no longer worn by the test subject, the method further comprising presenting, in response to determining that the digit-wearable device is no longer worn by the test subject, an instruction to reposition the digit-wearable device on the one or more digits of the test subject.

Example 94 is the method of any one of example(s)s 77 to 93, wherein the one or more identifiable characteristics of the one or more digits includes an artificial code coupled to a digit, wherein the artificial code is coupled to the digit such that the artificial code is destroyed when removed from the digit.

Example 95 is the method of example(s) 94, wherein at least a portion of the artificial code is applied to the digit via ink.

Example 96 is the method of example(s) 94 or example 95, wherein at least a portion of the artificial code is printed on an anti-tamper adhesive coupled to the digit.

Example 97 is the method of any one of example(s) 94 to 96, wherein accessing the authentication data includes accessing an authentication database containing a plurality of artificial codes associated with a plurality of individuals, wherein each of the plurality of artificial codes is associated with a respective one of the plurality of individuals after being coupled to a respective digit of the respective one of the plurality of individuals, and wherein the accessed authentication data includes an expected artificial code associated with an intended test subject such that authenticating the digit-wearable device includes comparing the artificial code of the test subject with the expected artificial code of the intended test subject to determine if the test subject is the intended test subject.

Example 98 is the method of any one of example(s)s 77 to 97, further comprising generating one or more test results associated with the testing session based at least in part on the determined one or more physiological parameters.

Example 99 is the method of any one of example(s)s 77 to 98, wherein the one or more identifiable characteristics of the one or more digits includes i) an identifiable topological feature of the one or more digits; ii) a skin tone of the one or more digits; iii) a tissue elasticity associated with the one or more digits; or iv) any combination of i-iii.

Example 100 is the method of any one of example(s)s 77 to 99, wherein the digit-wearable device is a home sleep test device.

Example 101 is the method of any one of example(s)s 77 to 100, wherein the digit-wearable diagnostic device includes a photoplethysmography sensor, and wherein the sensor data includes photoplethysmography data.

Example 102 is the method of any one of example(s)s 77 to 101, wherein comparing the identification data with the authentication data includes identifying a confidence value, wherein the confidence value is indicative of a level of confidence that the identification data matches the authentication data, and wherein generating the chain of custody determination is based at least in part on the confidence value.

Example 103 is the method of any one of example(s)s 77 to 102, wherein authenticating the digit-wearable device further includes determining that the one or more digits of the test subject on which the digit-wearable device is worn is living tissue.

Example 104 is the method of any one of example(s) 77 to 103, further comprising: associating a respiratory therapy device with the testing session, wherein associating the respiratory therapy device with the testing session includes determining that the respiratory therapy device is being used by the test subject based at least in part on the sensor data; and identifying a respiratory therapy interference instance indicative that the respiratory therapy device is no longer used by the test subject, wherein generating the chain of custody determination is further based at least in part on the respiratory therapy interference instance.

Example 105 is a system comprising: a control system comprising one or more processors; and a memory having stored thereon machine readable instructions; wherein the control system is coupled to the memory, and the method of any one of example(s)s 77 to 103 is implemented when the machine executable instructions in the memory are executed by at least one of the one or more processors of the control system.

Example 106 is a system for monitoring a diagnostic chain of custody, the system comprising a control system configured to implement the method of any one of example(s)s 77 to 104.

Example 107 is a computer program product comprising instructions which, when executed by a computer, cause the computer to carry out the method of any one of example(s)s 77 to 104.

Example 108 is the computer program product of example (s) 107, wherein the computer program product is a non-transitory computer readable medium.

Example 109 is a system comprising: a digit-wearable device having one or more sensors for receiving sensor data, the digit-wearable device worn on one or more digits of a test subject; and a control system having one or more processors and a memory having stored thereon machine readable instructions which, when executed by the one or more processors cause the one or more processors to perform operations including: determining one or more physiological parameters from at least a first portion of the sensor data acquired during a test session; associating the determined one or more physiological parameters with the testing session; authenticating the digit-wearable device, wherein authenticating the digit-wearable device includes: determining identification data based at least in part on at least a second portion of the sensor data, wherein the identification data includes one or more identifiable characteristics of the one or more digits; accessing authentication data, wherein the authentication data includes one or more authentication characteristics; comparing the identification data with the authentication data to determine a match, wherein the digit-wearable device is authenticated when a match is determined; generating a chain of custody determination based at least in part on the authentication of the digit-wearable device; and associating the chain of custody determination with the testing session.

Example 110 is the system of example(s) 109, wherein the one or more identifiable characteristics includes at least a portion of a digitprint.

Example 111 is the system of example(s) 109 or example 110, wherein the first portion of the sensor data includes the second portion of the sensor data.

Example 112 is the system of any one of example(s)s 109 to 111, wherein the digit-wearable device includes a first sensor positioned over a first digit and a second sensor positioned over a second digit, wherein the first portion of the sensor data is acquired by the first sensor, and wherein the second portion of the sensor data is acquired by the second sensor.

Example 113 is the system of any one of example(s)s 109 to 111, wherein the first portion of the sensor data is acquired by a first sensor and the second portion of the sensor data is acquired by the first sensor.

Example 114 is the system of any one of example(s)s 109 to 113, wherein accessing the authentication data includes accessing a database of authentication characteristics associated with a plurality of individuals.

Example 115 is the system of any one of example(s)s 109 to 113, wherein the operations further comprise: initially authenticating the digit-wearable device, wherein initially authenticating the digit-wearable device occurs before authenticating the digit-wearable device, and wherein initially authenticating the digit-wearable device includes: determining initial identification data based at least in part on at least a third portion of the sensor data, wherein the initial identification data includes the one or more identifiable characteristics of the one or more digits; and storing the initial identification data as the authentication data such that authenticating the digit-wearable device includes comparing the identification data with the initial identification data; wherein the chain of custody determination is indicative of a validity of the determined one or more physiological parameters associated with a time period between initially authenticating the digit-wearable device and authenticating the digit-wearable device.

Example 116 is the system of any one of examples 109 to 113, wherein the operations further comprise: receiving additional sensor data from a user device, wherein the additional sensor data is acquired of the one or more digits of the test subject; determining initial identification data based at least in part on the additional sensor data, wherein the initial identification data includes the one or more identifiable characteristics of the one or more digits; and storing the initial identification data as the authentication data such that authenticating the digit-wearable device includes comparing the identification data with the initial identification data.

Example 117 is the system of any one of example(s) 109 to 116, where the first portion of the sensor data is acquired by i) an ultrasonic sensor; ii) an optical sensor; iii) a capacitive sensor; iv) a thermal sensor; v) a radiofrequency sensor; vi) a sonar sensor; vii) a tactile sensor; or viii) any combination of i-vii.

Example 118 is the system of any one of example(s) 109 to 117, wherein the determined identification data includes a change over time of the one or more identifiable characteristics.

119 The system of any one of example(s) 109 to 118, wherein the operations further comprise: re-authenticating the digit-wearable device after authenticating the digit-wearable device; and updating the chain of custody determination based at least in part on the re-authentication of the digit-wearable device.

Example 120 is the system of example(s) 119, wherein re-authentication of the digit-wearable device and updating of the chain of custody determination occur periodically based on a preset schedule.

Example 121 is the system of example(s) 119 or example 120, wherein the operations further comprise identifying an out-of-threshold deviation in the one or more physiological parameters, wherein re-authentication of the digit-wearable device and updating of the chain of custody determination occur in response to identifying the out-of-threshold deviation in the one or more physiological parameters.

Example 122 is the system of any one of example(s) 119 to 121, wherein the operations further comprise identifying a dropout in the received sensor data, wherein re-authentication of the digit-wearable device and updating of the chain of custody determination occur in response to identifying the dropout in the received sensor data.

Example 123 is the system of any one of example(s) 119 to 122, wherein the sensor data includes accelerometer data, the method wherein the operations further comprise detecting an acceleration over a threshold value based at least in part on the accelerometer data, wherein re-authentication of the digit-wearable device and updating of the chain of custody determination occur in response to detecting the acceleration over the threshold value.

Example 124 is the system of any one of example(s)s 119 to 123, wherein the operations further comprise generating an inference that the digit-wearable device has been removed based at least in part on the received sensor data, wherein re-authentication of the digit-wearable device and updating of the chain of custody determination occur in response to generating the inference.

Example 125 is the system of any one of example(s)s 119 to 124, wherein re-authenticating the digit-wearable device includes determining that the digit-wearable device is no longer worn by the test subject, the method wherein the operations further comprise presenting, in response to determining that the digit-wearable device is no longer worn by the test subject, an instruction to reposition the digit-wearable device on the one or more digits of the test subject.

Example 126 is the system of any one of example(s)s 109 to 125, wherein the one or more identifiable characteristics of the one or more digits includes an artificial code coupled to a digit, wherein the artificial code is coupled to the digit such that the artificial code is destroyed when removed from the digit.

Example 127 is the system of example(s) 126, wherein at least a portion of the artificial code is applied to the digit via ink.

Example 128 is the system of example(s) 126 or example 127, wherein at least a portion of the artificial code is printed on an anti-tamper adhesive coupled to the digit.

Example 129 is the system of any one of example(s)s 126 to 128, wherein accessing the authentication data includes accessing an authentication database containing a plurality of artificial codes associated with a plurality of individuals, wherein each of the plurality of artificial codes is associated with a respective one of the plurality of individuals after being coupled to a respective digit of the respective one of the plurality of individuals, and wherein the accessed authentication data includes an expected artificial code associated with an intended test subject such that authenticating the digit-wearable device includes comparing the artificial code of the test subject with the expected artificial code of the intended test subject to determine if the test subject is the intended test subject.

Example 130 is the system of any one of example(s)s 109 to 129, wherein the operations further comprise generating one or more test results associated with the testing session based at least in part on the determined one or more physiological parameters.

Example 131 is the system of any one of example(s)s 109 to 130, wherein the one or more identifiable characteristics of the one or more digits includes i) an identifiable topological feature of the one or more digits; ii) a skin tone of the one or more digits; iii) a tissue elasticity associated with the one or more digits; or iv) any combination of i-iii.

Example 132 is the system of any one of example(s)s 109 to 131, wherein the digit-wearable device is a home sleep test device.

Example 133 is the system of any one of example(s)s 109 to 132, wherein the digit-wearable diagnostic device includes a photoplethysmography sensor, and wherein the sensor data includes photoplethysmography data.

Example 134 is the system of any one of example(s)s 109 to 133, wherein comparing the identification data with the authentication data includes identifying a confidence value, wherein the confidence value is indicative of a level of confidence that the identification data matches the authentication data, and wherein generating the chain of custody determination is based at least in part on the confidence value.

Example 135 is the system of any one of example(s)s 109 to 134, wherein authenticating the digit-wearable device further includes determining that the one or more digits of the test subject on which the digit-wearable device is worn is living tissue.

Example 136 is the system of any one of example(s) 109 to 135, wherein the operations further include: associating a respiratory therapy device with the testing session, wherein associating the respiratory therapy device with the testing session includes determining that the respiratory therapy device is being used by the test subject based at least in part on the sensor data; and identifying a respiratory therapy interference instance indicative that the respiratory therapy device is no longer used by the test subject, wherein generating the chain of custody determination is further based at least in part on the respiratory therapy interference instance.

Example 137 is a method comprising: providing a tag applied to an intended test subject, the tag having an anti-tamper authentication feature, wherein the anti-tamper authentication feature is altered when the tag is removed from the test subject, and wherein the anti-tamper authentication feature, when altered, is rendered unsuitable for authentication; providing a diagnostic wearable device applied to a test subject, wherein the diagnostic wearable device interacts with the anti-tamper authentication feature of the tag; authenticating the tag with the diagnostic wearable device based at least in part on the diagnostic wearable device's interaction with the anti-tamper authentication feature, wherein successful authentication is indicative that the test subject is the intended test subject, and wherein unsuccessful authentication occurs when the anti-tamper authentication feature is altered; collecting sensor data from the test subject via the diagnostic wearable device; and associating the collected sensor data with the intended test subject based at least in part on the authentication of the tag with the diagnostic wearable device.

Example 138 is the method of example(s) 137, wherein the anti-tamper authentication feature includes a mechanical feature, and wherein successfully authenticating the tag with the diagnostic wearable device includes the diagnostic wearable device detecting the mechanical feature of the tag in an unaltered state.

Example 139 is the method of example(s) 137 or example 138, wherein the anti-tamper authentication feature includes an optically readable pattern, and wherein successfully authenticating the tag with the diagnostic wearable device includes the diagnostic wearable device detecting the optically readable pattern in an unaltered state.

Example 140 is the method of any one of example(s)s 137 to 139, wherein the anti-tamper authentication feature includes an electrical circuit, and wherein successfully authenticating the tag with the diagnostic wearable device includes the diagnostic wearable device detecting the electrical circuit in an unaltered state.

Example 140 is the method of any one of example(s) 137 to 139, wherein the anti-tamper authentication feature includes a radiofrequency transmitter configured to emit a radiofrequency signal, and wherein successfully authenticating the tag with the diagnostic wearable device includes the diagnostic wearable device detecting the radiofrequency signal in an unaltered state.

Example 141 is the method of example(s) 140, wherein the radiofrequency transmitter is configured to emit a radiofrequency signal in response to receiving a radiofrequency request signal from the diagnostic wearable device.

Example 142 is the method of example(s) 140 or example 141, wherein successfully authenticating the tag with the diagnostic wearable device includes detecting a strength of the radiofrequency signal above a threshold value.

Example 143 is the method of any one of example(s)s 137 to 142, wherein the anti-tamper authentication feature includes an authentication key, and wherein successfully authenticating the tag with the diagnostic wearable device includes the diagnostic wearable device receiving the authentication key.

Example 144 is the method of example(s) 143, further comprising receiving tag enrollment information, wherein the tag enrollment information includes an enrollment authentication key; and wherein successfully authenticating the tag with the diagnostic wearable device includes matching the authentication key with the enrollment authentication key.

Example 145 is the method of example(s) 143 or example 144, wherein associating the collected sensor data with the intended test subject includes associating the collected sensor data with the authentication key.

Example 146 is the method of example(s) 145, wherein associating the collected sensor data with the authentication key includes encrypting the collected sensor data with the authentication key.

Example 147 is the method of any one of example(s)s 137 to 146, wherein associating the collected sensor data with the intended test subject occurs in response to successfully authenticating the tag.

Example 148 is the method of any one of example(s)s 137 to 147, wherein collecting the sensor data occurs only in response to successfully authenticating the tag.

Example 149 is the method of any one of example(s)s 137 to 148, further comprising removing the diagnostic wearable device from the test subject, wherein removal of the diagnostic wearable device induces alteration of the anti-tamper authentication feature of the tag.

Example 150 is the method of any one of example(s)s 137 to 149, wherein at least a portion of the anti-tamper authentication feature is applied to skin of the intended test subject via ink.

Example 151 is the method of example(s) 150, wherein the ink is invisible or substantially invisible under visible light.

Example 152 is the method of example(s) 150 or example 151, wherein the at least a portion of the anti-tamper authentication feature applied via ink includes a unique identifier.

Example 153 is the method of any one of example(s)s 137 to 152, wherein at least a portion of the anti-tamper authentication feature includes a substrate adhesively coupled to skin of the intended test subject, wherein removal, or partial removal, of the substrate from the skin of the intended test subject alters the anti-tamper authentication feature.

Example 154 is the method of example(s) 153, wherein the diagnostic wearable device includes an optical sensor, and wherein the diagnostic wearable device is couplable to skin of the test subject using the substrate of the anti-tamper authentication feature.

Example 155 is the method of example(s) 154, wherein the diagnostic wearable device is a photoplethysmography sensor, wherein the substrate of the anti-tamper authentication feature includes an adhesive part having a first portion containing an optically readable pattern and a second portion, wherein the first portion of the adhesive part is couplable to the skin of the test subject, and wherein the second portion of the adhesive part secures the photoplethysmography sensor over the first portion of the adhesive part such that the photoplethysmography sensor can read the optically readable pattern and obtain photoplethysmography data from the test subject.

Example 156 is the method of any one of example(s)s 137 to 155, wherein providing the tag applied to the intended test subject includes: receiving, by a user device, additional sensor data; verifying the identity of the intended test subject based at least in part on the additional sensor data; and detecting presence of the tag applied to the intended test subject based at least in part on the additional sensor data.

Example 157 is the method of example(s) 156, wherein the additional sensor data includes image data, wherein verifying the identity of the intended test subject includes using the image data to compare a face of the intended test subject with an image on a credential, and wherein detecting presence of the tag applied to the intended test subject includes using the image data to determine that the tag is applied to a body part of the intended test subject.

Example 158 is the method of example(s) 157, wherein verifying the identity of the intended test subject further includes extracting the image on the credential from the image data.

Example 159 is the method of any one of example(s)s 137 to 158, further comprising receiving confirmation information associated with the tag applied to the intended test subject, wherein the confirmation information is indicative that a trusted individual performed or witnessed application of the tag to the intended test subject, wherein authenticating the tag with the diagnostic wearable device is further based at least in part on the confirmation information.

Example 160 is the method of any one of example(s)s 137 to 159, wherein the anti-tamper authentication feature is configured to automatically become altered after a preset duration of time has elapsed since being applied to the intended test subject.

Example 161 is the method of any one of example(s)s 137 to 160, wherein the tag, when applied to the intended test subject, facilitates placement of the diagnostic wearable device on the test subject.

Example 162 is a method comprising: providing a tag applied to an intended test subject, the tag having an anti-tamper authentication feature, wherein the anti-tamper authentication feature is altered when the tag is removed from the test subject, and wherein the anti-tamper authentication feature, when altered, is rendered unsuitable for authentication; providing a diagnostic wearable device applied to a test subject; receiving, by a user device, first data from the anti-tamper authentication feature; receiving, by the user device, second data from the diagnostic wearable device; authenticating the tag with the diagnostic wearable device based at least in part on the first data and the second data, wherein successful authentication is indicative that the test subject is the intended test subject, and wherein unsuccessful authentication occurs when the anti-tamper authentication feature is altered; storing sensor data collected from the test subject via the diagnostic wearable device, wherein the sensor data is included in the second data or in additional data received by the user device; and associating the sensor data with the intended test subject based at least in part on the authentication of the tag with the diagnostic wearable device.

Example 163 is the method of example(s) 162, wherein the anti-tamper authentication feature includes a mechanical feature, and wherein at least one of receiving the first data and receiving the second data occurs in response to the diagnostic wearable device coupling with the mechanical feature of the tag when the anti-tamper authentication feature is in an unaltered state.

Example 164 is the method of example(s) 162 or example 163, wherein the anti-tamper authentication feature includes an optically readable pattern, and wherein at least a portion of the first data is encoded in the optically readable pattern.

Example 165 is the method of example(s) 164, wherein receiving the first data from the anti-tamper authentication feature includes: detecting, by the diagnostic wearable device, the first data from the optically readable pattern; and receiving, by the user device, the first data from the anti-tamper authentication feature via the diagnostic wearable device.

Example 166 is the method of any one of example(s)s 162 to 165, wherein the anti-tamper authentication feature includes an electrical circuit, and wherein at least a portion of the first data is encoded in the electrical circuit.

Example 167 is the method of example(s) 166, wherein receiving the first data from the anti-tamper authentication feature includes: detecting, by the diagnostic wearable device, the first data from the electrical circuit; and receiving, by the user device, the first data from the anti-tamper authentication feature via the diagnostic wearable device.

Example 168 is the method of any one of example(s)s 162 to 167, wherein the anti-tamper authentication feature includes a radiofrequency transmitter configured to emit a radiofrequency signal, and wherein at least a portion of the first data is encoded in the radiofrequency signal.

Example 169 is the method of example(s) 168, wherein receiving the first data from the anti-tamper authentication feature includes: detecting, by the diagnostic wearable device, the first data from the radiofrequency signal; and receiving, by the user device, the first data from the anti-tamper authentication feature via the diagnostic wearable device.

Example 170 is the method of example(s) 168 or 169, wherein the radiofrequency transmitter is configured to emit a radiofrequency signal in response to receiving a radiofrequency request signal from at least one of the diagnostic wearable device and the user device.

Example 171 is the method of any one of example(s)s 168 to 170, wherein successfully authenticating the tag with the diagnostic wearable device includes: detecting, by the user device, a strength of the radiofrequency signal; detecting, by the user device, an additional strength of an additional radiofrequency signal from the diagnostic wearable device; and comparing the strength of the radiofrequency signal with the additional strength of the additional radiofrequency signal.

Example 172 is the method of any one of example(s)s 162 to 171, wherein the anti-tamper authentication feature includes an authentication key, and wherein successfully authenticating the tag with the diagnostic wearable device includes receiving the authentication key by the user device.

Example 173 is the method of example(s) 172, further comprising receiving, by the user device, tag enrollment information, wherein the tag enrollment information includes an enrollment authentication key; and wherein successfully authenticating the tag with the diagnostic wearable device includes matching the authentication key with the enrollment authentication key.

Example 174 is the method of example(s) 172 or example 173, wherein associating the received sensor data with the intended test subject includes associating the received sensor data with the authentication key.

Example 175 is the method of example(s) 174, wherein associating the received sensor data with the authentication key includes encrypting the received sensor data with the authentication key.

Example 176 is the method of any one of example(s)s 162 to 175, wherein associating the received sensor data with the intended test subject occurs in response to successfully authenticating the tag.

Example 177 is the method of any one of example(s)s 162 to 176, further comprising removing the diagnostic wearable device from the test subject, wherein removal of the diagnostic wearable device induces alteration of the anti-tamper authentication feature of the tag.

Example 178 is the method of any one of example(s)s 162 to 177, wherein at least a portion of the anti-tamper authentication feature is applied to skin of the intended test subject via ink.

Example 179 is the method of example(s) 178, wherein the ink is invisible or substantially invisible under visible light.

Example 180 is the method of example(s) 178 or example 179, wherein the at least a portion of the anti-tamper authentication feature applied via ink includes a unique identifier.

Example 181 is the method of any one of example(s)s 162 to 180, wherein at least a portion of the anti-tamper authentication feature includes a substrate adhesively coupled to skin of the intended test subject, wherein removal, or partial removal, of the substrate from the skin of the intended test subject alters the anti-tamper authentication feature.

Example 182 is the method of example(s) 181, wherein the diagnostic wearable device includes an optical sensor, and wherein the diagnostic wearable device is couplable to skin of the test subject using the substrate of the anti-tamper authentication feature.

Example 183 is the method of example(s) 182, wherein the diagnostic wearable device is a photoplethysmography sensor, wherein the substrate of the anti-tamper authentication feature includes an adhesive part having a first portion containing an optically readable pattern and a second portion, wherein the first portion of the adhesive part is couplable to the skin of the test subject, and wherein the second portion of the adhesive part secures the photoplethysmography sensor over the first portion of the adhesive part such that the photoplethysmography sensor can read the optically readable pattern and obtain photoplethysmography data from the test subject.

Example 184 is the method of any one of example(s)s 162 to 183, wherein providing the tag applied to the intended test subject includes: receiving, by the user device, additional sensor data; verifying the identity of the intended test subject based at least in part on the additional sensor data; and detecting presence of the tag applied to the intended test subject based at least in part on the additional sensor data.

Example 185 is the method of example(s) 184, wherein the additional sensor data includes image data, wherein verifying the identity of the intended test subject includes using the image data to compare a face of the intended test subject with an image on a credential, and wherein detecting presence of the tag applied to the intended test subject includes using the image data to determine that the tag is applied to a body part of the intended test subject.

Example 186 is the method of example(s) 185, wherein verifying the identity of the intended test subject further includes extracting the image on the credential from the image data.

Example 187 is the method of any one of example(s) 162 to 186, further comprising receiving, by the user device, confirmation information associated with the tag applied to the intended test subject, wherein the confirmation information is indicative that a trusted individual performed or witnessed application of the tag to the intended test subject, wherein authenticating the tag with the diagnostic wearable device is further based at least in part on the confirmation information.

Example 188 is the method of any one of example(s) 162 to 187, wherein the anti-tamper authentication feature is configured to automatically become altered after a preset duration of time has elapsed since being applied to the intended test subject.

Example 189 is the method of any one of example(s) 162 to 188, wherein the tag, when applied to the intended test subject, facilitates placement of the diagnostic wearable device on the test subject.

Example 190 is the method of any one of example(s) 137 to 189, further comprising: associating a respiratory therapy device with the test subject, wherein associating the respiratory therapy device with the test subject includes determining that the respiratory therapy device is being used by the test subject based at least in part on the successful authentication of the tag.

Example 191 is a system comprising: a control system comprising one or more processors; and a memory having stored thereon machine readable instructions; wherein the control system is coupled to the memory, and the method of any one of example(s)s 137 to 190 is implemented when the machine executable instructions in the memory are executed by at least one of the one or more processors of the control system.

Example 192 is a system for monitoring a diagnostic chain of custody, the system comprising a control system configured to implement the method of any one of example(s)s 137 to 190.

Example 193 is a computer program product comprising instructions which, when executed by a computer, cause the computer to carry out the method of any one of example(s)s 137 to 190.

Example 194 is the computer program product of example(s) 193 wherein the computer program product is a non-transitory computer readable medium.

Example 195 is a system, comprising: a tag applied to an intended test subject, the tag having an anti-tamper authentication feature, wherein the anti-tamper authentication feature is altered when the tag is removed from the test subject, and wherein the anti-tamper authentication feature, when altered, is rendered unsuitable for authentication; a diagnostic wearable device applied to a test subject, wherein the diagnostic wearable device interacts with the anti-tamper authentication feature of the tag; and a control system having one or more processors and a memory having stored thereon machine readable instructions which, when executed by the one or more processors cause the one or more processors to perform operations including: authenticating the tag with the diagnostic wearable device based at least in part on the diagnostic wearable device's interaction with the anti-tamper authentication feature, wherein successful authentication is indicative that the test subject is the intended test subject, and wherein unsuccessful authentication occurs when the anti-tamper authentication feature is altered; collecting sensor data from the test subject via the diagnostic wearable device; and associating the collected sensor data with the intended test subject based at least in part on the authentication of the tag with the diagnostic wearable device.

Example 196 is the system of example(s) 195, wherein the anti-tamper authentication feature includes a mechanical feature, and wherein successfully authenticating the tag with the diagnostic wearable device includes the diagnostic wearable device detecting the mechanical feature of the tag in an unaltered state.

Example 197 is the system of example(s) 195 or example 196, wherein the anti-tamper authentication feature includes an optically readable pattern, and wherein successfully authenticating the tag with the diagnostic wearable device includes the diagnostic wearable device detecting the optically readable pattern in an unaltered state.

Example 198 is the system of any one of example(s)s 195 to 197, wherein the anti-tamper authentication feature includes an electrical circuit, and wherein successfully authenticating the tag with the diagnostic wearable device includes the diagnostic wearable device detecting the electrical circuit in an unaltered state.

Example 198 is the system of any one of example(s)s 195 to 197, wherein the anti-tamper authentication feature includes a radiofrequency transmitter configured to emit a radiofrequency signal, and wherein successfully authenticating the tag with the diagnostic wearable device includes the diagnostic wearable device detecting the radiofrequency signal in an unaltered state.

Example 199 is the system of example(s) 198, wherein the radiofrequency transmitter is configured to emit a radiofrequency signal in response to receiving a radiofrequency request signal from the diagnostic wearable device.

Example 200 is the system of example(s) 198 or example 199, wherein successfully authenticating the tag with the diagnostic wearable device includes detecting a strength of the radiofrequency signal above a threshold value.

Example 201 is the system of any one of example(s)s 195 to 200, wherein the anti-tamper authentication feature includes an authentication key, and wherein successfully authenticating the tag with the diagnostic wearable device includes the diagnostic wearable device receiving the authentication key.

Example 202 is the system of example(s) 201, wherein the operations further comprise receiving tag enrollment information, wherein the tag enrollment information includes an enrollment authentication key; and wherein successfully authenticating the tag with the diagnostic wearable device includes matching the authentication key with the enrollment authentication key.

Example 203 is the system of example(s) 201 or example 202, wherein associating the collected sensor data with the intended test subject includes associating the collected sensor data with the authentication key.

Example 204 is the system of example(s) 203, wherein associating the collected sensor data with the authentication key includes encrypting the collected sensor data with the authentication key.

Example 205 is the system of any one of example(s)s 195 to 204, wherein associating the collected sensor data with the intended test subject occurs in response to successfully authenticating the tag.

Example 206 is the system of any one of example(s)s 195 to 205, wherein collecting the sensor data occurs only in response to successfully authenticating the tag.

Example 207 is the system of any one of example(s)s 195 to 206, wherein the operations further comprise removing the diagnostic wearable device from the test subject, wherein removal of the diagnostic wearable device induces alteration of the anti-tamper authentication feature of the tag.

Example 208 is the system of any one of example(s)s 195 to 207, wherein at least a portion of the anti-tamper authentication feature is applied to skin of the intended test subject via ink.

Example 209 is the system of example(s) 208, wherein the ink is invisible or substantially invisible under visible light.

Example 210 is the system of example(s) 208 or example 209, wherein the at least a portion of the anti-tamper authentication feature applied via ink includes a unique identifier.

Example 211 is the system of any one of example(s)s 195 to 210, wherein at least a portion of the anti-tamper authentication feature includes a substrate adhesively coupled to skin of the intended test subject, wherein removal, or partial removal, of the substrate from the skin of the intended test subject alters the anti-tamper authentication feature.

Example 212 is the system of example(s) 211, wherein the diagnostic wearable device includes an optical sensor, and wherein the diagnostic wearable device is couplable to skin of the test subject using the substrate of the anti-tamper authentication feature.

Example 213 is the system of example(s) 212, wherein the diagnostic wearable device is a photoplethysmography sensor, wherein the substrate of the anti-tamper authentication feature includes an adhesive part having a first portion containing an optically readable pattern and a second portion, wherein the first portion of the adhesive part is couplable to the skin of the test subject, and wherein the second portion of the adhesive part secures the photoplethysmography sensor over the first portion of the adhesive part such that the photoplethysmography sensor can read the optically readable pattern and obtain photoplethysmography data from the test subject.

Example 214 is the system of any one of example(s)s 195 to 213, wherein providing the tag applied to the intended test subject includes: receiving, by a user device, additional sensor data; verifying the identity of the intended test subject based at least in part on the additional sensor data; and detecting presence of the tag applied to the intended test subject based at least in part on the additional sensor data.

Example 215 is the system of example(s) 214, wherein the additional sensor data includes image data, wherein verifying the identity of the intended test subject includes using the image data to compare a face of the intended test subject with an image on a credential, and wherein detecting presence of the tag applied to the intended test subject includes using the image data to determine that the tag is applied to a body part of the intended test subject.

Example 216 is the system of example(s) 215, wherein verifying the identity of the intended test subject further includes extracting the image on the credential from the image data.

Example 217 is the system of any one of example(s)s 195 to 216, wherein the operations further comprise receiving confirmation information associated with the tag applied to the intended test subject, wherein the confirmation information is indicative that a trusted individual performed or witnessed application of the tag to the intended test subject, wherein authenticating the tag with the diagnostic wearable device is further based at least in part on the confirmation information.

Example 218 is the system of any one of example(s)s 195 to 217, wherein the anti-tamper authentication feature is configured to automatically become altered after a preset duration of time has elapsed since being applied to the intended test subject.

Example 219 is the system of any one of example(s)s 195 to 218, wherein the tag, when applied to the intended test subject, facilitates placement of the diagnostic wearable device on the test subject.

Example 220 is a system, comprising: a tag applied to an intended test subject, the tag having an anti-tamper authentication feature, wherein the anti-tamper authentication feature is altered when the tag is removed from the test subject, and wherein the anti-tamper authentication feature, when altered, is rendered unsuitable for authentication; a diagnostic wearable device applied to a test subject; a user device; and a control system having one or more processors and a memory having stored thereon machine readable instructions which, when executed by the one or more processors cause the one or more processors to perform operations including: receiving, by the user device, first data from the anti-tamper authentication feature; receiving, by the user device, second data from the diagnostic wearable device; authenticating the tag with the diagnostic wearable device based at least in part on the first data and the second data, wherein successful authentication is indicative that the test subject is the intended test subject, and wherein unsuccessful authentication occurs when the anti-tamper authentication feature is altered; storing sensor data collected from the test subject via the diagnostic wearable device, wherein the sensor data is included in the second data or in additional data received by the user device; and associating the sensor data with the intended test subject based at least in part on the authentication of the tag with the diagnostic wearable device.

Example 221 is the system of example(s) 220, wherein the anti-tamper authentication feature includes a mechanical feature, and wherein at least one of receiving the first data and receiving the second data occurs in response to the diagnostic wearable device coupling with the mechanical feature of the tag when the anti-tamper authentication feature is in an unaltered state.

Example 222 is the system of example(s) 220 or example 221, wherein the anti-tamper authentication feature includes an optically readable pattern, and wherein at least a portion of the first data is encoded in the optically readable pattern.

Example 223 is the system of example(s) 222, wherein receiving the first data from the anti-tamper authentication feature includes: detecting, by the diagnostic wearable device, the first data from the optically readable pattern; and receiving, by the user device, the first data from the anti-tamper authentication feature via the diagnostic wearable device.

Example 224 is the system of any one of example(s)s 220 to 223, wherein the anti-tamper authentication feature includes an electrical circuit, and wherein at least a portion of the first data is encoded in the electrical circuit.

Example 225 is the system of example(s) 224, wherein receiving the first data from the anti-tamper authentication feature includes: detecting, by the diagnostic wearable device, the first data from the electrical circuit; and receiving, by the user device, the first data from the anti-tamper authentication feature via the diagnostic wearable device.

Example 226 is the system of any one of example(s)s 220 to 225, wherein the anti-tamper authentication feature includes a radiofrequency transmitter configured to emit a radiofrequency signal, and wherein at least a portion of the first data is encoded in the radiofrequency signal.

Example 227 is the system of example(s) 226, wherein receiving the first data from the anti-tamper authentication feature includes: detecting, by the diagnostic wearable device, the first data from the radiofrequency signal; and receiving, by the user device, the first data from the anti-tamper authentication feature via the diagnostic wearable device.

Example 228 is the system of example(s) 226 or 227, wherein the radiofrequency transmitter is configured to emit a radiofrequency signal in response to receiving a radiofrequency request signal from at least one of the diagnostic wearable device and the user device.

Example 229 is the system of any one of example(s)s 226 to 228, wherein successfully authenticating the tag with the diagnostic wearable device includes: detecting, by the user device, a strength of the radiofrequency signal; detecting, by the user device, an additional strength of an additional radiofrequency signal from the diagnostic wearable device; and comparing the strength of the radiofrequency signal with the additional strength of the additional radiofrequency signal.

Example 230 is the system of any one of example(s)s 220 to 229, wherein the anti-tamper authentication feature includes an authentication key, and wherein successfully authenticating the tag with the diagnostic wearable device includes receiving the authentication key by the user device.

Example 231 is the system of example(s) 230, wherein the operations further comprise receiving, by the user device, tag enrollment information, wherein the tag enrollment information includes an enrollment authentication key; and wherein successfully authenticating the tag with the diagnostic wearable device includes matching the authentication key with the enrollment authentication key.

Example 232 is the system of example(s) 230 or example 231, wherein associating the received sensor data with the intended test subject includes associating the received sensor data with the authentication key.

Example 233 is the system of example(s) 232, wherein associating the received sensor data with the authentication key includes encrypting the received sensor data with the authentication key.

Example 234 is the system of any one of example(s)s 220 to 233, wherein associating the received sensor data with the intended test subject occurs in response to successfully authenticating the tag.

Example 235 is the system of any one of example(s)s 220 to 234, wherein the operations further comprise removing the diagnostic wearable device from the test subject, wherein removal of the diagnostic wearable device induces alteration of the anti-tamper authentication feature of the tag.

Example 236 is the system of any one of example(s)s 220 to 235, wherein at least a portion of the anti-tamper authentication feature is applied to skin of the intended test subject via ink.

Example 237 is the system of example(s) 236, wherein the ink is invisible or substantially invisible under visible light.

Example 238 is the system of example(s) 236 or example 237, wherein the at least a portion of the anti-tamper authentication feature applied via ink includes a unique identifier.

Example 239 is the system of any one of example(s)s 220 to 238, wherein at least a portion of the anti-tamper authentication feature includes a substrate adhesively coupled to skin of the intended test subject, wherein removal, or partial removal, of the substrate from the skin of the intended test subject alters the anti-tamper authentication feature.

Example 240 is the system of example(s) 239, wherein the diagnostic wearable device includes an optical sensor, and wherein the diagnostic wearable device is couplable to skin of the test subject using the substrate of the anti-tamper authentication feature.

Example 241 is the system of example(s) 240, wherein the diagnostic wearable device is a photoplethysmography sensor, wherein the substrate of the anti-tamper authentication feature includes an adhesive part having a first portion containing an optically readable pattern and a second portion, wherein the first portion of the adhesive part is couplable to the skin of the test subject, and wherein the second portion of the adhesive part secures the photoplethysmography sensor over the first portion of the adhesive part such that the photoplethysmography sensor can read the optically readable pattern and obtain photoplethysmography data from the test subject.

Example 242 is the system of any one of example(s)s 220 to 241, wherein providing the tag applied to the intended test subject includes: receiving, by the user device, additional sensor data; verifying the identity of the intended test subject based at least in part on the additional sensor data; and detecting presence of the tag applied to the intended test subject based at least in part on the additional sensor data.

Example 243 is the system of example(s) 242, wherein the additional sensor data includes image data, wherein verifying the identity of the intended test subject includes using the image data to compare a face of the intended test subject with an image on a credential, and wherein detecting presence of the tag applied to the intended test subject includes using the image data to determine that the tag is applied to a body part of the intended test subject.

Example 244 is the system of example(s) 243, wherein verifying the identity of the intended test subject further includes extracting the image on the credential from the image data.

Example 245 is the system of any one of example(s)s 220 to 244, wherein the operations further comprise receiving, by the user device, confirmation information associated with the tag applied to the intended test subject, wherein the confirmation information is indicative that a trusted individual performed or witnessed application of the tag to the intended test subject, wherein authenticating the tag with the diagnostic wearable device is further based at least in part on the confirmation information.

Example 246 is the system of any one of example(s)s 220 to 245, wherein the anti-tamper authentication feature is configured to automatically become altered after a preset duration of time has elapsed since being applied to the intended test subject.

Example 247 is the system of any one of example(s)s 220 to 246, wherein the tag, when applied to the intended test subject, facilitates placement of the diagnostic wearable device on the test subject.

Example 248 is the system of any one of example(s) 195 to 247, wherein the operations further include: associating a respiratory therapy device with the test subject, wherein associating the respiratory therapy device with the test subject includes determining that the respiratory therapy device is being used by the test subject based at least in part on the successful authentication of the tag.

What is claimed is:

1. A method comprising:

receiving sensor data from a digit-wearable device worn on one or more digits of a test subject;

determining one or more physiological parameters from at least a first portion of the sensor data acquired during a test session;

associating the determined one or more physiological parameters with the testing session;

authenticating the digit-wearable device to determine that the test subject is an intended individual for the test session, wherein authenticating the digit-wearable device includes:

determining identification data based at least in part on at least a second portion of the sensor data, wherein the identification data includes one or more identifiable characteristics of the one or more digits of the test subject;

accessing authentication data, wherein the authentication data includes one or more authentication characteristics of the test subject;

comparing the identification data with the authentication data to determine a match, wherein the digit-wearable device is authenticated when a match is determined;

generating a chain of custody determination of the validity of the sensor data based at least in part on the authentication of the digit-wearable device; and associating the chain of custody determination with the test testing session; and generating one or more test results associated with the testing session based at least in part on the determined one or more physiological parameters.

2. The method of claim 1, wherein the one or more identifiable characteristics includes at least a portion of a digitprint.

3. The method of claim 1, wherein the digit-wearable device includes a first sensor positioned over a first digit and a second sensor positioned over a second digit, wherein the first portion of the sensor data is acquired by the first sensor, and wherein the second portion of the sensor data is acquired by the second sensor.

4. The method of claim 1, wherein accessing the authentication data includes accessing a database of authentication characteristics associated with a plurality of individuals.

5. The method of claim 1, further comprising:

initially authenticating the digit-wearable device, wherein initially authenticating the digit-wearable device occurs before authenticating the digit-wearable device, and wherein initially authenticating the digit-wearable device includes:

determining initial identification data based at least in part on at least a third portion of the sensor data, wherein the initial identification data includes the one or more identifiable characteristics of the one or more digits; and storing the initial identification data as the authentication data such that authenticating the digit-wearable device includes comparing the identification data with the initial identification data;

wherein the chain of custody determination is indicative of a validity of the determined one or more physiological parameters associated with a time period between initially authenticating the digit-wearable device and authenticating the digit-wearable device.

6. The method of claim 1, further comprising:

receiving additional sensor data from a user device, wherein the additional sensor data is acquired of the one or more digits of the test subject;

determining initial identification data based at least in part on the additional sensor data, wherein the initial identification data includes the one or more identifiable characteristics of the one or more digits; and storing the initial identification data as the authentication data such that authenticating the digit-wearable device includes comparing the identification data with the initial identification data.

7. The method of claim 1, where the first portion of the sensor data is acquired by i) an ultrasonic sensor; ii) an optical sensor; iii) a capacitive sensor; iv) a thermal sensor; v) a radiofrequency sensor; vi) a sonar sensor; vii) a tactile sensor; or viii) any combination of i-vii.

8. The method of claim 1, further comprising:

re-authenticating the digit-wearable device after authenticating the digit-wearable device; and updating the chain of custody determination based at least in part on the re-authentication of the digit-wearable device.

9. The method of claim 8, wherein re-authentication of the digit-wearable device and updating of the chain of custody determination occur periodically based on a preset schedule.

10. The method of claim 8, further comprising identifying an out-of-threshold deviation in the one or more physiological parameters, wherein re-authentication of the digit-wearable device and updating of the chain of custody determination occur in response to identifying the out-of-threshold deviation in the one or more physiological parameters.

11. The method of claim 8, further comprising identifying a dropout in the received sensor data, wherein re-authentication of the digit-wearable device and updating of the chain of custody determination occur in response to identifying the dropout in the received sensor data.

12. The method of claim 8, wherein the sensor data includes accelerometer data, the method further comprising detecting an acceleration over a threshold value based at least in part on the accelerometer data, wherein re-authentication of the digit-wearable device and updating of the chain of custody determination occur in response to detecting the acceleration over the threshold value.

13. The method of claim 8, further comprising generating an inference that the digit-wearable device has been removed based at least in part on the received sensor data, wherein re-authentication of the digit-wearable device and updating of the chain of custody determination occur in response to generating the inference.

14. The method of claim 8, wherein re-authenticating the digit-wearable device includes determining that the digit-wearable device is no longer worn by the test subject, the method further comprising presenting, in response to determining that the digit-wearable device is no longer worn by the test subject, an instruction to reposition the digit-wearable device on the one or more digits of the test subject.

15. The method of claim 1, wherein the one or more identifiable characteristics of the one or more digits includes an artificial code coupled to a digit, wherein the artificial code is coupled to the digit such that the artificial code is destroyed when removed from the digit.

16. The method of claim 15, wherein accessing the authentication data includes accessing an authentication database containing a plurality of artificial codes associated with a plurality of individuals, wherein each of the plurality of artificial codes is associated with a respective one of the plurality of individuals after being coupled to a respective digit of the respective one of the plurality of individuals, and wherein the accessed authentication data includes an expected artificial code associated with an intended test subject such that authenticating the digit-wearable device includes comparing the artificial code of the test subject with the expected artificial code of the intended test subject to determine if the test subject is the intended test subject.

17. The method of claim 1, wherein the digit-wearable device is a home sleep test device.

18. The method of claim 1, wherein comparing the identification data with the authentication data includes identifying a confidence value, wherein the confidence value is indicative of a level of confidence that the identification data matches the authentication data, and wherein generating the chain of custody determination is based at least in part on the confidence value.

19. The method of claim 1, further comprising:

associating a respiratory therapy device with the testing session, wherein associating the respiratory therapy device with the testing session includes determining that the respiratory therapy device is being used by the test subject based at least in part on the sensor data; and identifying a respiratory therapy interference instance indicative that the respiratory therapy device is no longer used by the test subject, wherein generating the chain of custody determination is further based at least in part on the respiratory therapy interference instance.

20. A system comprising:

a digit-wearable device having one or more sensors for receiving sensor data, the digit-wearable device worn on one or more digits of a test subject; and a control system having one or more processors and a memory having stored thereon machine readable instructions which, when executed by the one or more processors cause the one or more processors to perform operations including:

determining one or more physiological parameters from at least a first portion of the sensor data acquired during a test session;

associating the determined one or more physiological parameters with the testing session;

authenticating the digit-wearable device, wherein authenticating the digit-wearable device includes:

determining identification data based at least in part on at least a second portion of the sensor data, wherein the identification data includes one or more identifiable characteristics of the one or more digits;

accessing authentication data, wherein the authentication data includes one or more authentication characteristics;

comparing the identification data with the authentication data to determine a match, wherein the digit-wearable device is authenticated when a match is determined;

generating a chain of custody determination based at least m part on the authentication of the digit-wearable device; and associating the chain of custody determination with the testing session; and generating one or more test results associated with the testing session based at least in part on the determined one or more physiological parameters.

\* \* \* \* \*